United States Patent
He et al.

(10) Patent No.: US 11,786,507 B2
(45) Date of Patent: Oct. 17, 2023

(54) METHODS OF TREATING HIV-ASSOCIATED NEUROLOGICAL DISORDERS (HAND)

(71) Applicant: Rosalind Franklin University of Medicine and Science, Chicago, IL (US)

(72) Inventors: Johnny He, North Chicago, IL (US); Xiaojie Zhao, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 17/547,472

(22) Filed: Dec. 10, 2021

(65) Prior Publication Data

US 2022/0184036 A1 Jun. 16, 2022

Related U.S. Application Data

(60) Provisional application No. 63/124,372, filed on Dec. 11, 2020.

(51) Int. Cl.
| | | |
|---|---|---|
| *A61K 31/04* | (2006.01) | |
| *A61K 31/506* | (2006.01) | |
| *A61K 45/06* | (2006.01) | |
| *A61P 25/00* | (2006.01) | |
| *A61K 31/41* | (2006.01) | |

(52) U.S. Cl.
CPC ............ *A61K 31/41* (2013.01); *A61K 31/506* (2013.01); *A61K 45/06* (2013.01); *A61P 25/00* (2018.01)

(58) Field of Classification Search
CPC ...... A61K 31/41; A61K 31/506; A61K 45/06; A61K 31/42; A61P 25/00
USPC ....................................................... 514/359
See application file for complete search history.

(56) References Cited

U.S. PATENT DOCUMENTS

2010/0234349 A1* 9/2010 Olsen et al. ......... A61K 31/554
514/211.13

OTHER PUBLICATIONS

Callahan PM, Hutchings EJ, Kille NJ, Chapman JM, Terry AV Jr. Positive allosteric modulator of α7 nicotinic-acetylcholine receptors, PNU-120596 augments the effects of donepezil on learning and memory in aged rodents and non-human primates. Neuropharmacology. Apr. 2013;67:201-12. (Year: 2013).*
Xu P, Wang Y, Qin Z, Qiu L, Zhang M, Huang Y, Zheng JC. Combined Medication of Antiretroviral Drugs Tenofovir Disoproxil Fumarate, Emtricitabine, and Raltegravir Reduces Neural Progenitor Cell Proliferation In Vivo and In Vitro. J Neuroimmune Pharmacol. Dec. 2017;12(4):682-692. (Year: 2017).*
Capó-Vélez CM, Delgado-Vélez M, Báez-Pagán CA, Lasalde-Dominicci JA. Nicotinic Acetylcholine Receptors in HIV: Possible Roles During HAND and Inflammation. Cell Mol Neurobiol. Oct. 2018;38(7):1335-1348. doi: 10.1007/s10571-018-0603-8. Epub Jul. 14, 2018. PMID: 30008143; PMCID: PMC6133022. (Year: 2018).*
Alzarea S, Rahman S (2019). "Alpha-7 Nicotinic Receptor Allosteric Modulator PNU120596 Prevents Lipopolysaccharide-Induced Anxiety, Cognitive Deficit and Depression-Like Behaviors in Mice", Behav. Brain Res., Jul. 2, 2019, vol. 366, pp. 19-28.
Asomugha, C.O., et al., "ACh Receptors Link Two Signaling Pathways to Neuroprotection Against Glutamate-Induced Excitotoxicity in Isolated RGCs", J. Neurochem., Jan. 2010, vol. 112(1), pp. 214-226.
Barone, F.C., et al., "SB 239063, a Second-Generation p38 Mitogen-Activated Protein Kinase Inhibitor, Reduces Brain Injury and Neurological Deficits in Cerebral Focal Ischemia", J. Pharmacol. Exp. Ther., 2001, vol. 296(2), pp. 312-321.
Bertrand, D., et al., "Therapeutic Potential of alpha7 Nicotinic Acetylcholine Receptors", Pharmacol. Rev., Oct. 2015, vol. 67(4), pp. 1025-1073.
Bouzat, C., et al., "Molecular Function of alpha7 Nicotinic Receptors as Drug Targets", J. Physiol., 2018, vol. 596(10), pp. 1847-1861.
Brenman, J.E., et al., "Interaction of Nitric Oxide Synthase with the Postsynaptic Density Protein PSD-95 and alpha1-Syntrophin Mediated by PDZ Domains", Cell, Mar. 8, 1996, vol. 84(5), pp. 757-767.
Brinton, R.D., "Minireview: Translational Animal Models of Human Menopause: Challenges and Emerging Opportunities", Endocrinology, Aug. 2012, vol. 153(8), pp. 3571-3578.
Bruchas, M.R., et al., "Stress-Induced p38 Mitogen-Activated Protein Kinase Activation Mediates Kappa-Opioid-Dependent Dysphoria", J. Neurosci., Oct. 24, 2007, vol. 27(43), pp. 11614-11623.
Buckingham, S.D., et al., "Nicotinic Acetylcholine Receptor Signalling: Roles in Alzheimer's Disease and Amyloid Neuroprotection", Pharmacol. Rev., 2009, vol. 61(1), pp. 39-61.
Bustos, F.J., et al., "Epigenetic Editing of the Dig4/PSD95 Gene Improves Cognition in Aged and Alzheimer's Disease Mice", Brain, 2017, vol. 140(12), pp. 3252-3268.
Calabrese, F., et al., "Synaptic Alterations Associated with Depression and Schizophrenia: Potential as a Therapeutic Target", Expert Opin. Ther. Targets, 2016, vol. 20, pp. 1195-1207, (Abstract only).

(Continued)

*Primary Examiner* — Yevgeny Valenrod
(74) *Attorney, Agent, or Firm* — McDonnell Boehnen Hulbert & Berghoff LLP

(57) ABSTRACT

In the present disclosure, doxycycline-inducible astrocyte-specific HIV Tat transgenic mice (iTat), a surrogate HAND model, were treated with PNU-125096, a positive allosteric modulator of α7 nicotinic acetylcholine receptor (α7 nAChR) and effects on Tat-induced behavioral impairments and neuropathologies were observed. This disclosure shows that PNU-125096 treatment significantly improved locomotor, learning and memory deficits of iTat mice while inhibited glial activation and increased PSD-95 expression in the cortex and hippocampus of iTat mice. α7 nAChR knockout eliminated the protective effects of PNU-125096 on iTat mice. In addition, inhibition of p38 phosphorylation by SB239063, a p38 MAPK-specific inhibitor, exacerbated Tat neurotoxicity in iTat mice. These findings demonstrated for the first time that α7 nAChR activation led to protection against HAND and suggest that α7 nAChR and PNU-125096 hold significant promise for development of therapeutics for HAND.

10 Claims, 42 Drawing Sheets

Specification includes a Sequence Listing.

(56) References Cited

OTHER PUBLICATIONS

Callahan, P.M., et al., "Positive Allosteric Modulator of alpha7 Nicotinic-Acetylcholine Receptors, PNU-120596 Augments the Effects of Donepezil on Learning and Memory in Aged Rodents and Non-Human Primates", Neuropharmacology, Apr. 2013, vol. 67C, pp. 201-212.

Cao, J., et al., "The PSD95-nNOS Interface: a Target for Inhibition of Excitotoxic p38 Stress-Activated Protein Kinase Activation and Cell Death", J. Cell Biol., Jan. 3, 2005, vol. 168(1), pp. 117-126.

Capo-Velez, C.M., et al., "The alpha7-Nicotinic Receptor Contributes to gp120-Induced Neurotoxicity: Implications in HIV-Associated Neurocognitive Disorders", Sci. Rep., Jan. 29, 2018, vol. 8(1), article 1829, pp. 1-11.

Chan, W.K, et al., "Frontal Cortical alpha7 and alpha4beta2 Nicotinic Acetylcholine Receptors in Working and Reference Memory", Neuropharmacology, Jun. 2007, vol. 52(8), pp. 1641-1649, (Abstract only).

Chen, Y., et al., "Hsp90 Chaperone Inhibitor 17-AAG Attenuates Abeta-Induced Synaptic Toxicity and Memory Impairment", J. Neurosci., Feb. 12, 2014, vol. 34(7), pp. 2464-2470.

Cui, H., et al., "PDZ Protein Interactions Underlying NMDA Receptor-Mediated Excitotoxicity and Neuroprotection by PSD-95 Inhibitors", J. Neurosci., Sep. 12, 2007, vol. 27(37), pp. 9901-9915.

Dajas-Bailador, F.A., et al., "Nicotine Activates the Extracellular Signal-Regulated Kinase 1/2 Via the Alpha7 Nicotinic Acetylcholine Receptor and Protein Kinase A, in SH-SY5Y Cells and Hippocampal Neurones", J. Neurochem., 2002, vol. 80(3), pp. 520-530.

Dash, P. K., et al., "Activation of alpha 7 Cholinergic Nicotinic Receptors Reduce Blood-Brain Barrier Permeability following Experimental Traumatic Brain Injury", J. Neurosci., Mar. 2, 2016, vol. 36(9), pp. 2809-2818.

Dineley, K.T., et al., "Beta-Amyloid Activates the Mitogen-Activated Protein Kinase Cascade Via Hippocampal alpha7 Nicotinic Acetylcholine Receptors: In Vitro and In Vivo Mechanisms Related to Alzheimer's Disease", J. Neurosci., Jun. 15, 2001, vol. 21(12), pp. 4125-4133.

Dineley, K.T., et al., "Nicotinic ACh Receptors as Therapeutic Targets in CNS Disorders", Trends Pharmacol. Sci., Feb. 2015, vol. 36(2), pp. 96-108.

Egea, J., et al., "Anti-Inflammatory Role of Microglial alpha7 nAChRs and its Role in Neuroprotection", Biochem. Pharmacol., Oct. 15, 2015, vol. 97(4), pp. 463-472, (Abstract only).

El Kouhen, R., et al., "Pharmacology of alpha7 Nicotinic Acetylcholine Receptor Mediated Extracellular Signal-Regulated Kinase Signalling in PC12 Cells", Br. J. Pharmacol., 2009, vol. 156(4), pp. 638-648.

Eugenin, E.A., et al., "HIV-Tat Induces Formation of an LRP-PSD-95-NMDAR-nNOS Complex that Promotes Apoptosis in Neurons and Astrocytes", Proc. Natl. Acad. Sci., Feb. 27, 2007, vol. 104(9), pp. 3438-3443.

Fernandes, C., et al., "Performance Deficit of alpha7 Nicotinic Receptor Knockout Mice in a Delayed Matching-to-Place Task Suggests a Mild Impairment of Working/Episodic-like Memory", Genes Brain Behav., 2006, vol. 5(6), pp. 433-440.

Fernandez, E., et al., "Arc Requires PSD95 for Assembly into Postsynaptic Complexes Involved with Neural Dysfunction and Intelligence", Cell Rep., Oct. 17, 2017, vol. 21(3), pp. 679-691.

Foucault-Fruchard, L. and Antier, D., "Therapeutic Potential of alpha7 Nicotinic Receptor Agonists to Regulate Neuroinflammation in Neurodegenerative Diseases", Neural Regen. Res., Sep. 2017, vol. 12(9), pp. 1418-1421.

Gajanayaka, N., et al., "HIV and HIV-Tat Inhibit LPS-Induced IL-27 Production in Human Macrophages by Distinct Intracellular Signaling Pathways", J. Leukoc. Biol., Sep. 2017, vol. 102(3), pp. 925-939.

Gong, Y. and Lippa, C.F., "Disruption of the Postsynaptic Density in Alzheimer's Disease and Other Neurodegenerative Dementias", Am. J. Alzheimers Dis. Other. Demen., Nov. 2010, vol. 25(7), pp. 547-555.

Han, K. and Kim, E., "Synaptic Adhesion Molecules and PSD-95", Prog. Neurobiol., Mar. 2008, vol. 84(3), pp. 263-283, (Abstract only).

Hoskin, J.L., et al., "Nicotinic Acetylcholine Receptor Agonists for the Treatment of Alzheimer's Dementia: An Update", Nicotine Tob. Res., 2019, vol. 21(3), pp. 370-376.

Jones, C.K., et al., "Muscarinic and Nicotinic Acetylcholine Receptor Agonists and Allosteric Modulators for the Treatment of Schizophrenia", Neuropsychopharmacology, Jan. 2012, vol. 37(1), pp. 16-42.

Khan, Z. and Lafon, M., "PDZ Domain-Mediated Protein Interactions: Therapeutic Targets in Neurological Disorders", Curr. Med. Chem., 2014, vol. 21(23), pp. 2632-2641 (Abstract only).

Kim, N., et al., "Tat Engagement of p38 MAP Kinase and IRF7 Pathways Leads to Activation of Interferon-Stimulated Genes in Antigen-Presenting Cells", Blood, May 16, 2013, vol. 121(20), pp. 4090-4100.

Kim, H., et al., "The Proximal Tubular alpha7 Nicotinic Acetylcholine Receptor Attenuates Ischemic Acute Kidney Injury through Akt/PKC Signaling-Mediated HO-1 Induction", Exp. Mol. Med., 2018, vol. 50(40), pp. 1-17.

King, J.R., et al., "A G Protein-Coupled alpha7 Nicotinic Receptor Regulates Signaling and TNF-alpha Release in Microglia", FEBS Open Bio, 2017, vol. 7(9), pp. 1350-1361.

King, J.R., et al., "Identification and Characterization of a G Protein-Binding Cluster in alpha7 Nicotinic Acetylcholine Receptors", J. Biol. Chem., Aug. 14, 2015, vol. 290(33), pp. 20060-20070.

King, J.R. and Kabbani, N., "Alpha 7 Nicotinic Receptor Coupling to Heterotrimeric G Proteins Modulates RhoA Activation, Cytoskeletal Motility, and Structural Growth", J. Neurochem., 2016, vol. 138(4), pp. 532-545.

Koukouli, F., et al., "Nicotine Reverses Hypofrontality in Animal Models of addiction and Schizophrenia", Nat. Med., Mar. 2017, vol. 23(3), pp. 347-354.

Larsen, H.M., et al., "Alpha7 Nicotinic Acetylcholine Receptors and Neural Network Synaptic Transmission in Human Induced Pluripotent Stem Cell-Derived Neurons", Stem Cell Res., 2019, vol. 41, article 101642, pp. 1-10.

Li, L.P., et al., "PSD95 and nNOS Interaction as a Novel Molecular Target to Modulate Conditioned Fear: Relevance to PTSD", Transl. Psychiatry, 2018, vol. 8(1), article 155, pp. 1-13.

Liu, Q., et al., "Alpha7 Nicotinic Acetylcholine Receptor-Mediated Anti-Inflammatory Effect in a Chronic Migraine Rat Model Via the Attenuation of Glial Cell Activation", J. Pain Res., 2018, vol. 11, pp. 1129-1140.

Liu, L., et al., "Alpha7 Nicotinic Acetylcholine Receptor is Required for Amyloid Pathology in Brain Endothelial Cells Induced by Glycoprotein 120, Methamphetamine and Nicotine", Sci. Rep., Jan. 11, 2017, vol. 7, article 40467, pp. 1-12.

Mannangatti, P., et al., "A Role for p38 Mitogen-Activated Protein Kinase-Mediated Threonine 30-Dependent Norepinephrine Transporter Regulation in Cocaine Sensitization and Conditioned Place Preference", J. Biol. Chem., Apr. 24, 2015, vol. 290(17), pp. 10814-10827.

Manetti, D., et al., "Designing Selective Modulators for the Nicotinic Receptor Subtypes: Challenges and Opportunities", Future Med. Chem., 2018, vol. 10(4), pp. 433-459.

Maphis, N., et al., "Selective Suppression of the Alpha Isoform of p38 MAPK Rescues Late-Stage Tau Pathology", Alzheimers Res. Ther., Dec. 15, 2016, vol. 8(1), article 54, pp. 1-15.

McDaid, J., et al., "Ethanol-Induced Motor Impairment Mediated by Inhibition of alpha7 Nicotinic Receptors", J. Neurosci., 2016, vol. 36(29), pp. 7768-7778.

McLean, S.L., et al., "PNU-120596, a Positive Allosteric Modulator of alpha7 Nicotinic Acetylcholine Receptors, Reverses a Sub-Chronic Phencyclidine-Induced Cognitive Deficit in the Attentional Set-Shifting Task in Female Rats", J. Psychopharmacol., 2012, vol. 26(9), pp. 1265-1270.

Medders, K.E. and Kaul, M., "Mitogen-Activated Protein Kinase p38 in HIV Infection and Associated Brain Injury", J. Neuroimmune Pharmacol., Jun. 2011, vol. 6(2), pp. 202-215.

(56) References Cited

OTHER PUBLICATIONS

Mineur, Y.S., et al., "Hippocampal alpha7 Nicotinic ACh Receptors Contribute to Modulation of Depression-Like Behaviour in C57BL/6J Mice", Br. J. Pharmacol., Jun. 2018, vol. 175(11), pp. 1903-1914.
Natarajaseenivasan, K., et al., "Astrocytic Metabolic Switch is a Novel Etiology for Cocaine and HIV-1 Tat-Mediated Neurotoxicity", Cell Death Dis., 2018, vol. 9(4), article 415, pp. 1-12.
Nikiforuk, A., et al., "Positive Allosteric Modulation of alpha 7 Nicotinic Acetylcholine Receptors Enhances Recognition Memory and Cognitive Flexibility in Rats", Eur. Neuropsychopharmacol., Aug. 2015, vol. 25(8), pp. 1300-1313, (Abstract only).
Pandya, A.A. and Yakel, J.L., "Activation of the alpha7 Nicotinic ACh Receptor Induces Anxiogenic Effects in Rats which is Blocked by a 5-Ht(1)a Receptor Antagonist", Neuropharmacology, Jul. 2013, vol. 70, pp. 35-42.
Potasiewicz, A., et al., "Stimulation of Nicotinic Acetylcholine alpha7 Receptors Rescue Schizophrenia-Like Cognitive Impairments in Rats", J. Psychopharmacol., 2017, vol. 31, pp. 260-271, (Abstract only).
Rahman, S., et al., "Nicotinic Receptor Modulation to Treat Alcohol and Drug Dependence", Front Neurosci., Jan. 15, 2015, vol. 8, article 426, pp. 1-11.
Robson, M.J., et al., "p38alpha MAPK Signaling Drives Pharmacologically Reversible Brain and Gastrointestinal Phenotypes in the Sert Ala56 Mouse", Proc. Natl. Acad. Sci., 2018, vol. 115(43), pp. E10245-E10254.
Selkoe, D.J., "Alzheimer's Disease is a Synaptic Failure", Science, Oct. 25, 2002, vol. 298(5594), pp. 789-791.
Singh, I.N., et al., "Differential Involvement of p38 and JNK MAP Kinases in HIV-1 Tat and gp120-Induced Apoptosis and Neurite Degeneration in Striatal Neurons", Neuroscience, 2005, vol. 135(3), pp. 781-790.
Sultana, R., et al., "Decreased Levels of PSD95 and Two Associated Proteins and Increased Levels of BCI2 and Caspase 3 in Hippocampus from Subjects with Amnestic Mild Cognitive Impairment: Insights into their Potential Roles for Loss of Synapses and Memory, Accumulation of Abeta, and Neurodegeneration in a Prodromal Stage of Alzheimer's Disease", J. Neurosci. Res., Feb. 15, 2010, vol. 88(3), pp. 469-477.
Sun, F., et al., "Boosting Endogenous Resistance of Brain to Ischemia", Mol. Neurobiol., Apr. 2017, vol. 54(3), pp. 2045-2059.
Tregellas, J.R., and Wylie, K.P., "Alpha7 Nicotinic Receptors as Therapeutic Targets in Schizophrenia", Nicotine Tob. Res., 2019, vol. 21(3), pp. 349-356.
Tripathi, P., et al., "Ibuprofen Protects from Cypermethrin-Induced Changes in the Striatal Dendritic Length and Spine Density", Mol. Neurobiol., Mar. 2017, vol. 55(3), pp. 2333-2339.
Uteshev, V.V., "Allosteric Modulation of Nicotinic Acetylcholine Receptors: The Concept and Therapeutic Trends", Curr. Pharm. Des., 2016, vol. 22(14), pp. 1986-1997, (Abstract only).
Uteshev, V.V., "The Therapeutic Promise of Positive Allosteric Modulation of Nicotinic Receptors", Eur. J. Pharmacol., Mar. 15, 2014, vol. 727, pp. 181-185.
Xiao, C., et al., "Neural Circuits and Nicotinic Acetylcholine Receptors Mediate the Cholinergic Regulation of Midbrain Dopaminergic Neurons and Nicotine Dependence", Acta Pharmacol. Sin., Sep. 25, 2019, vol. 41(1), pp. 1-9.
Xiang, T., et al., "Nicotine Enhances Invasion and Metastasis of Human Colorectal Cancer Cells through the Nicotinic Acetylcholine Receptor Downstream p38 MAPK Signaling Pathway", Oncol. Rep., Jan. 2016, vol. 35(1), pp. 205-210.
Xu, S., et al., "Activation of Alpha7-nAChRs Protects SH-SY5Y Cells from 1-methyl-4-phenylpyridinium-Induced Apoptotic Cell Death Via ERK/p53 Signaling Pathway", J. Cell. Physiol., 2019, vol. 234, pp. 18480-18491, (Abstract only).
Wen, A.Y., et al., "The Role of the Transcription Factor Creb in Immune Function", J. Immunol., Dec. 1, 2010, vol. 185(11), pp. 6413-6419.

Yang, J-S., et al., "Rational Engineering of Enzyme Allosteric Regulation Through Sequence Evolution Analysis", PLoS Comput. Biol., Jul. 2012, vol. 8(7), e1002612, pp. 1-10.
Yang, T., et al., "The Current Agonists and Positive Allosteric Modulators of alpha7 nAChR for CNS Indications in Clinical Trials", Acta. Pharm. Sin. B, 2017, vol. 7(6), pp. 611-622.
Ye, Q., et al., Ferrostatin-1 Mitigates Cognitive Impairment of epileptic rats by inhibiting P38 MAPK activation. Epilepsy Behav., 2020, vol. 103, Part A, article 106670, pp. 1-3, (Abstract only).
Zhao, L., et al., "Protection Against the Neurotoxic Effects of beta-Amyloid Peptide on Cultured Neuronal Cells by Lovastatin Involves Elevated Expression of alpha7 Nicotinic Acetylcholine Receptors and Activating Phosphorylation of Protein Kinases", Am. J. Pathol., Apr. 2018, vol. 188(4), pp. 1081-1093.
Zhang, B., et al., "Alpha7 Nicotinic Acetylcholine Receptor is Required for Blood-Brain Barrier Injury-Related CNS Disorders Caused by Cryptococcus neoformans and HIV-1 Associated Comorbidity Factors", BMC Infect. Dis., Aug. 19, 2015, vol. 15, article 352, pp. 1-11.
Zhao, X., et al., "Activation of $\alpha7$ Nicotinic Acetylcholine Receptor Ameliorated HIV-Associated Neurology and Neuropathology", Brain, Jul. 1, 2021, pp. 1-129.
Zhao, X., et al., "Activation of $\alpha7$ Nicotinic Acetylcholine Receptor Ameliorates HIV-Associated Neurology and Neuropathology", Brain, Nov. 2021, vol. 144 (11), pp. 3355-3370.
Williams, D.K., et al., Positive Allosteric Modulators as an Approach to Nicotinic Acetylcholine Receptor-Targeted Therapeutics: Advantages and Limitations, Biochemical Pharmacology, May 7, 2011, vol. 82(8), pp. 915-930.
Brack-Werner, R., "Astrocytes: HIV Cellular Reservoirs and Important Participants in Neuropathogenesis", AIDS, Jan. 14, 1999, vol. 13(1), pp. 1-22.
Gibbs, K.L., et al., "Inhibiting p38 MAPK Alpha Rescues Axonal Retrograde Transport Defects in a Mouse Model of ALS", Cell Death and Disease, 2018, vol. 9, article 596, pp. 1-16.
Coulthard, L.R., et al., "p38MAPK: Stress Responses from Molecular Mechanisms to Therapeutics", Trends Mol. Med., Aug. 2009, vol. 15(8), pp. 369-379.
Akhtar-Khaleel, W.Z., et al., "Association of Midlife Smoking Status with Change in Processing Speed and Mental Flexibility Among HIV-Seropositive and HIV-Seronegative Older Men: the Multicenter Aids Cohort Study", J. Neurovirol., Apr. 2017, vol. 23(2), pp. 239-249.
Albuquerque, E.X., et al., "Mammalian Nicotinic Acetylcholine Receptors: From Structure to Function", Physiol. Rev., Jan. 2009, vol. 89(1), pp. 73-120.
Ande, A., et al. "Effect of Mild-to-Moderate Smoking on Viral Load, Cytokines, Oxidative Stress, and Cytochrome P450 Enzymes in Hiv-Infected Individuals", PLoS One, Apr. 16, 2015, vol. 10(4), article e0122402, pp. 1-16.
Cao J., et al., "RNA Deep Sequencing Analysis Reveals that Nicotine Restores Impaired Gene Expression by Viral Proteins in the Brains of HIV-1 Transgenic Rats", PLoS One, Jul. 16, 2013, vol. 8(7), article e68517, pp. 1-10.
Chang, L., et al., "Chronic Tobacco-Smoking on Psychopathological Symptoms, Impulsivity and Cognitive Deficits in HIV-Infected Individuals". J Neuroimmune Pharmacol., Sep. 2017, vol. 12(3), pp. 389-401.
Egger, M., et al. "Prognosis of HIV-1-Infected Patients Starting Highly Active Antiretroviral Therapy: a Collaborative Analysis of Prospective Studies", Lancet, Jul. 13, 2002, vol. 360(9327), pp. 119-129.
Fan, Y., et al., "Activation of Egr-1 Expression in Astrocytes by HIV-1 Tat: New Insights into Astrocyte-Mediated Tat Neurotoxicity", J. Neuroimmune Pharmacol., Mar. 2011, vol. 6(1), pp. 121-129.
Gamarel, K.E., et al., "Tobacco Use and Sustained Viral Suppression in Youth Living with HIV", AIDS Behav., Jun. 2018, vol. 22(6), pp. 2018-2025.
Giancola, M.L., et al., "Neuroactive Antiretroviral Drugs Do Not Influence Neurocognitive Performance in Less Advanced HIV-

(56) References Cited

OTHER PUBLICATIONS

Infected Patients Responding to Highly Active Antiretroviral Therapy", J. Acquir. Immune Defic. Syndr., Mar. 2006, vol. 41(3), pp. 332-337.

Han, H., et al., "Modulatory Effects of Nicotine on neuroHIV/neuroAIDS", J. Neuroimmune Pharmacol., Dec. 2018, vol. 13(4), pp. 467-478.

Harrison, J.D., et al., "The Nature and Consequences of Cognitive Deficits Among Tobacco Smokers with HIV: A Comparison to Tobacco Smokers without HIV", J. Neurovirol., Aug. 2017, vol. 23(4), pp. 550-557.

Heaton, R.K., et al., "The Impact of HIV-Associated Neuropsychological Impairment on Everyday Functioning", J. Int. Neuropsychol. Soc., May 2004, vol. 10(3), pp. 317-331.

Hudson, L., et al., "Detection of the Human Immunodeficiency Virus Regulatory Protein Tat in CNS Tissues", J. Neurovirol., Apr. 2000, vol. 6(2), pp. 145-155.

Kesby, J.P., et al., "The Effects of HIV-1 Regulatory TAT Protein Expression on Brain Reward Function, Response to Psychostimulants and Delay-Dependent Memory in Mice", Neuropharmacology, Oct. 2016, vol. 109, pp. 205-215.

Maschke, M., et al., "Incidence and Prevalence of Neurological Disorders Associated with HIV Since the Introduction of Highly Active Antiretroviral Therapy (HAART)", J. Neurol. Neurosurg. Psychiatry, Sep. 2000, vol. 69(3), pp. 376-380.

Barreto, G.E., et al., "Beneficial Effects of Nicotine, Cotinine and its Metabolites as Potential Agents for Parkinson's Disease", Frontiers in Aging Neuroscience, Jan. 9, 2015, vol. 6, article 340, pp. 1-13.

Levitzky, Y.S., et al., "Relation of Smoking Status to a Panel of Inflammatory Markers: the Framingham Offspring", Atherosclerosis, Nov. 2008, vol. 201(1), pp. 217-224.

Bradford, S.T., et al., "Nicotine Aggravates the Brain Postischemic Inflammatory Response", Am. J. Physiol. Heart Circ. Physiol., Jan. 14, 2011, vol. 300(4), pp. H1518-H1529.

Bryant, V.E., et al., "The Effects of Cigarette Smoking on Learning and Memory Performance Among People Living with HIV/AIDS", Aids Care, Oct. 2013, vol. 25(10), pp. 1308-1316.

Caniglia, E.C., et al., "Antiretroviral Penetration into the CNS and Incidence of Aids-Defining Neurologic Conditions", Neurology, Jul. 8, 2014, vol. 83(2), pp. 134-141.

Carey, A.N., et al., "Expression of HIV-Tat protein is Associated with Learning and Memory Deficits in the Mouse", Behav. Brain Res., Apr. 1, 2012, vol. 229(1), pp. 48-56.

Clements, J.E., et al., "The Central Nervous System is a Viral Reservoir in Simian Immunodeficiency Virus-Infected Macaques on Combined Antiretroviral Therapy: a Model for Human Immunodeficiency Virus Patients on Highly Active Antiretroviral Therapy", J. Neurovirol., Apr. 2005, vol. 11(2), pp. 180-189.

Dawes, S., et al., "Variable Patterns of Neuropsychological Performance in HIV-1 Infection". J. Clin. Exp. Neuropsychol., Aug. 2008, vol. 30(6), pp. 613-626.

Ellis, R., et al., "HIV and Antiretroviral Therapy in the Brain: Neuronal Injury and Repair", Nat. Rev. Neurosci., Jan. 2007, vol. 8(1), pp. 33-44.

Fan, Y., et al., "HIV Tat Impairs Neurogenesis through Functioning as a Notch Ligand and Activation of Notch Signaling Pathway", J. Neurosci., Nov. 2, 2016, vol. 36(44), pp. 11362-11373.

Fan, Y., and He, J.J., "HIV-1 Tat Promotes Lysosomal Exocytosis in Astrocytes and Contributes to Astrocyte-Mediated Tat Neurotoxicity", J. Biol. Chem., Oct. 21, 2016, vol. 291(43), pp. 22830-22840.

Fan, Y., and He, J.J., "HIV-1 Tat Induces Unfolded Protein Response and Endoplasmic Reticulum Stress in Astrocytes and Causes Neurotoxicity through Glial Fibrillary Acidic Protein (GFAP) Activation and Aggregation", J. Biol. Chem., Oct. 21, 2016, vol. 291(43), pp. 22819-22829.

Ferrando, S.J., et al., "Longitudinal Improvement in Psychomotor Processing Speed is Associated with Potent Combination Antiretroviral Therapy in HIV-1 Infection", J. Neuropsychiatry Clin. Neurosci., May 1, 2003, vol. 15(2), pp. 208-214.

Fields, J., et al., "HIV-1 Tat Alters Neuronal Autophagy by Modulating Autophagosome Fusion to the Lysosome: Implications for HIV-Associated Neurocognitive Disorders", J. Neurosci., Feb. 4, 2015, vol. 35(5), pp. 1921-1938.

Fu, X., et al., "HIV-1 Tat Activates Indoleamine 2,3 Dioxygenase in Murine Organotypic Hippocampal Slice Cultures in a P38 Mitogen-Activated Protein Kinase-Dependent Manner", J. Neuroinflammation, Aug. 2011, vol. 8, article 88, pp. 1-12.

Hahn, Y.K., et al., "Effects of Chronic HIV-1 Tat Exposure in the CNS: Heightened Vulnerability of Males Versus Females to Changes in Cell Numbers Synaptic Integrity, and Behavior", Brain Struct. Funct., Mar. 2015, vol. 220(2), pp. 605-623.

Heaton, R.K., et al., "HIV-Associated Neurocognitive Disorders Persist in the Era of Potent Antiretroviral Therapy: Charter Study", Neurology, Dec. 7, 2010, vol. 75(23), pp. 2087-2096.

Helleberg, M., et al., "Smoking and Life Expectancy Among HIV-Infected Individuals on Antiretroviral Therapy in Europe and North America", AIDS, Jan. 14, 2015, vol. 29(2), pp. 221-229.

Hoskin, J.L., et al., "Nicotinic Acetylcholine Receptor Agonists for the Treatment of Alzheimer's Dementia: An Update", Nicotine & Tobacco Research, 2019, pp. 370-376.

Johnson, T.P., et al., "Induction of IL-17 and Nonclassical T-Cell Activation by HIV-Tat Protein", Proc. Natl. Acad. Sci., Aug. 13, 2013, vol. 110(33), pp. 13588-13593.

Kim, B.O., et al., "Neuropathologies in Transgenic Mice Expressing Human Immunodeficiency Virus Type 1 Tat Protein Under the Regulation of the Astrocyte-Specific Glial Fibrillary Acidic Protein Promoter and Doxycycline", Am. J. Pathol., May 2003, vol. 162(5), pp. 1693-1707.

Langford, T.D., et al., "Changing Patterns in the Neuropathogenesis of HIV During the HAART Era", Brain Pathol., Apr. 2003, vol. 13(2), pp. 195-210.

Letendre, S., et al., "Validation of the CNS Penetration-Effectiveness Rank for Quantifying Antiretroviral Penetration into the Central Nervous System", Arch. Neurol., Jan. 2008, vol. 65(1), pp. 65-70.

Li, M.D., et al., "Transcriptome Sequencing of Gene Expression in the Brain of the HIV-1 Transgenic Rat", PLOS One, Mar. 2013, vol. 8(3), article e59582, pp. 1-16.

Liu, Y., et al., "Uptake of HIV-1 Tat Protein Mediated by Low-Density Lipoprotein Receptor-Related Protein Disrupts the Neuronal Metabolic Balance of the Receptor Ligands", Nat. Med., Dec. 2000, vol. 6(12), pp. 1380-1387.

Madani, A., et al., "Immune-Regulating Effects of Exercise on Cigarette Smoke-Induced Inflammation", Journal of Inflammation Research, Apr. 24, 2018, vol. 11, pp. 155-167.

Masliah, E., et al., "Changes in Pathological Findings at Autopsy in AIDS Cases for the Last 15 Years", AIDS, Jan. 7, 2000, vol. 14(1), pp. 69-74.

May, M., et al., "Prognosis of HIV-1-Infected Patients Up to 5 Years After Initiation of HAART: Collaborative Analysis of Prospective Studies", AIDS, May 31, 2007, vol. 21(9), pp. 1185-1197.

Mdodo, R., et al., "Cigarette Smoking Prevalence Among Adults with HIV Compared with the General Adult Population in the United States: Cross-Sectional Surveys", Ann. Intern. Med., Mar. 3, 2015, vol. 162(5), pp. 335-344.

Monforte, A., et al., "Insights into the Reasons for Discontinuation of the First Highly Active Antiretroviral Therapy (HAART) Regimen in a Cohort of Antiretroviral Naive Patients", I.CO.N.A. Study Group, Italian Cohort of Antiretroviral-Naive Patients, AIDS, Mar. 31, 2000, vol. 14(5), pp. 499-507.

Moreno-Gonzalez, I., et al., "Smoking Exacerbates Amyloid Pathology in a Mouse Model of Alzheimer's Disease", Nat. Commun., Feb. 19, 2013, vol. 4, article 1495, pp. 1-10.

Munoz, A., et al., "The Incubation Period of AIDS", AIDS, 1997, vol. 11, (suppl A), pp. S69-S76.

Nesil, T., et al., "Nicotine Attenuates the Effect of HIV-1 Proteins on the Neural Circuits of Working and Contextual Memories", Mol. Brain, Jul. 24, 2015, vol. 8, article 43, pp. 1-17.

Newhouse, P., et al., "Nicotine Treatment of Mild Cognitive Impairement: A 6-Month Double-Blind Pilot Clinical Trial", Neurology, Jan. 10, 2012, vol. 78(2), pp. 91-101.

(56) References Cited

OTHER PUBLICATIONS

Nicholatos, J.W., et al., "Nicotine Promotes Neuron Survival and Partially Protects from Parkinson's Disease by Suppressing SIRT6", Acta Neuropathologica. Communications, Nov. 8, 2018, vol. 6(1), article 120, pp. 1-18.

Sacktor N., et al., "HIV-Associated Cognitive Impairment Before and After the Advent of Combination Therapy", J. Neurovirol., Apr. 2002, vol. 8(2), pp. 136-142.

Uteshev, V.V., et al., "The Therapeutic Promise of Positive Allosteric Modulation of Nicotinic Receptors", Eur. J. Pharmacol., Mar. 15, 2014, vol. 727, pp. 181-185.

Bagasra, O., et al., "Cellular Reservoirs of HIV-1 in the Central Nervous System of Infected Individuals: Identification by the Combination of in situ Polymerase Chain Reaction and Immunohistochemistry", Aids, Jun. 1996, vol. 10(6), pp. 573-585, (Abstract only).

Cysique L.A., et al., "Prevalence and Pattern of Neuropsychological Impairment in Human Immunodeficiency Virus-Infected/Acquired Immunodeficiency Syndrome (HIV/AIDS) Patients Across Pre- and Post-Highly Active Antiretroviral Therapy Eras: a Combined Study of Two Cohorts", J. Neurovirol., Dec. 2004, vol. 10(6), pp. 350-357, (Abstract only).

Dajas-Bailador, F.A., et al., "The Alpha7 Nicotinic Acetylcholine Receptor Subtype Mediates Nicotine Protection against NMDA Excitotoxicity in Primary Hippocampal Cultures through a Ca(2+) Dependent Mechanism", Neuropharmacology, Dec. 2000, vol. 39(13), pp. 2799-2807.

Frankel, A.D., et al., "Cellular Uptake of the Tat Protein from Human Immunodeficiency Virus", Cell, Dec. 23, 1988, vol. 55(6), pp. 1189-1193.

Kaneko, S., et al., "Nicotine Protects Cultured Cortical Neurons Against Glutamate-Induced Cytotoxicity Via Alpha7-Neuronal Receptors and Neuronal CNS Receptors", Brain Res., Aug. 8, 1997, vol. 765(1), pp. 135-140.

Li, S.T., et al., "HIV-1 Tat Inhibits Long-Term Potentiation and Attenuates Spatial Learning [corrected]", Ann. Neurol., Mar. 2004, vol. 55(3), pp. 362-371.

May, M.T., et al., "HIV Treatment Response and Prognosis in Europe and North America in the First Decade of Highly Active Antiretroviral Therapy: a Collaborative Analysis", Lancet, Aug. 5, 2006, vol. 368(9534), pp. 451-458.

Monforte, A., et al., "Changing Incidence of Central Nervous System Diseases in the EuroSIDA Cohort", Ann. Neurol., Mar. 2004, vol. 55(3), pp. 320-328.

Shang, X., et al., "Nicotine Significantly Improves Chronic Stress-Induced Impairments of Cognition and Synaptic Plasficity in Mice", Molecular Neurobiology, Aug. 2017, vol. 54(6), pp. 4644-4658.

Strazielle, N., and Ghersi-Egea, J.F., "Factors Affecting Delivery of Antiviral Drugs to the Brain", Rev. Med. Virol., Nov. 16, 2005, vol. 15(2), pp. 105-133.

Waterhouse, U., et al., "Nicotine Self-Administration Reverses Cognitive Deficits in a Rat Model for Schizophrenia", Addiction Biology, Mar. 2018, vol. 23(2), pp. 620-630.

Zhou, B.Y., and He, J.J., "Proliferation Inhibition of Astrocytes, Neurons, and Non-Glial Cells by Intracellularly Expressed Human Immunodeficiency Virus Type 1 (HIV-1) Tat Protein", Neurosci. Lett., Apr. 15, 2004, vol. 359(3), pp. 155-158.

Porter, K., "Survival After Introduction of HAART in People with Known Duration of HIV-1 Infection. The Cascade Collaboration. Concerted Action on SeroConversion to AIDS and Death in Europe", Lancet, Apr. 1, 2000, vol. 355 (9210), pp. 1158-1159.

Monnig, M.A., et al., "Effects of Smoking and Alcohol Use on Neurocognitive Functioning in Heavy Drinking, HIV-Positive Men Who Have Sex with Men", AIDS Care, Mar. 2016, vol. 28(3), pp. 300-305.

Moran, L.M., et al., "Neonatal Intrahippocampal HIV-1 protein Tat(1-86) Injection: Neurobehavioral Alterations in the Absence of Increased Inflammatory Cytokine Activation", Int. J. Dev. Neurosci., Nov. 2014, vol. 38, pp. 195-203.

Nookala, A.R., et al., "Methamphetamine Augment HIV-1 Tat Mediated Memory Deficits by Altering the Expression of Synaptic Proteins and Neurotrophic Factors", Brain Behav. Immun., Jul. 2018, vol. 71, pp. 37-51.

Paris, J.J., et al., "Exposure to HIV-1 Tat in Brain Impairs Sensorimotor Gating and Activates Microglia in Limbic and Extralimbic Brain Regions of Male Mice", Behav. Brain Res., Sep. 15, 2015, vol. 291, pp. 209-218.

Paris, J.J., et al., "Anxiety-Like Behavior of Mice Produced by Conditional Central Expression of the HIV-1 Regulatory Protein, Tat.", Psychopharmacology (Berl), Jun. 2014, vol. 231(11), pp. 2349-2360.

Rahimian, P., and He, J.J., "HIV-1 Tat-Shortened Neurite Outgrowth Through Regulation of MicroRNA-132 and its Target Gene Expression", J. Neuroinflammation, Sep. 15, 2016, vol. 13(1), article 247, pp. 1-17.

Raybuck, J.D., et al. "A GluN2B-Selective NMDAR Antagonist Reverses Synapse Loss and Cognitive Impairment Produced by the HIV-1 Protein Tat", J. Neurosci., Aug. 16, 2017, vol. 37(33), pp. 7837-7847.

Royal III, W., et al., "Cigarette Smoke and Nicotine Effects on Brain Proinflammatory Responses and Behavioral and Motor Function in HIV-1 Transgenic Rats", J. Neurovirol., Apr. 2018, vol. 24(2), pp. 246-253.

Sacktor, N., et al., HIV-Associated Neurologic Disease Incidence Changes: Multicenter AIDS Cohort Study, 1990-1998, Neurology, Jan. 23, 2001, vol. 56(2), pp. 257-260.

Slotkin, T.A., et al., "Is There a Critical Period for the Developmental Neurotoxicity of Low-Level Tobacco Smoke Exposure?", Toxicological Sciences, 2017, vol. 155(1), pp. 75-84.

Stevens, T.R., et al., "Neuroprotection by Nicotine in Mouse Primary Cortical Cultures Involves Activation of Calcineurin and L-Type Calcium Channel Inactivation", J. Neurosci., Nov. 5, 2003, vol. 23(31), pp. 10093-10099.

Talhout, R., et al., "Hazardous Compounds in Tobacco Smoke", International Journal of Environmental Research and Public Health, Feb. 2011, vol. 8(2), pp. 613-628.

Tsima, B., et al., "Is Tobacco Use Associated with Neurocognitive Dysfunction in Individuals with HIV?", J. Int. Assoc. Providers of AIDS Care, Jan.-Dec. 2018, vol. 17, pp. 1-7.

Wallet, C., et al., "Microglial Cells: The Main HIV-1 Reservoir in the Brain", Front. Cell. Infect. Microbiol., Oct. 24, 2019, vol. 9, article 362, pp. 1-18.

Yilmaz, A., et al., "Antiretroviral Drug Treatment of CNS HIV-1 Infection", J. Antimicrob. Chemother., Feb. 2012, vol. 67(2), pp. 299-311.

Zhou, B.Y., et al., "Astrocyte Activation and Dysfunction and Neuron Death by HIV-1 Tat Expression in Astrocytes", Mol. Cell. Neurosci., Nov. 2004, vol. 27(3), pp. 296-305.

Zou, W., et al., "Protection Against Human Immunodeficiency Virus Type 1 Tat Neurotoxicity by Ginkgo Biloba Extract EGb 761 Involving Glial Fibrillary Acidic Protein", Am. J. Pathol., Dec. 2007, vol. 171(6), pp. 1923-1935.

Zou, W., et al., "Involvement of P300 in Constitutive and HIV-1 Tat-Activated Expression of Glial Fibrillary Acidic Protein in Astrocytes", Glia, Oct. 2010, vol. 58(13), pp. 1640-1648.

\* cited by examiner

Experimental groups

| Mice | Sex | PAM/DMSO | Groups |
|---|---|---|---|
| Wt | Male | DMSO | Wt+DMSO |
| | | PAM | Wt+PAM |
| | Female | DMSO | Wt+DMSO |
| | | PAM | Wt+PAM |
| iTat | Male | DMSO | iTat+DMSO |
| | | PAM | iTat+PAM |
| | Female | DMSO | iTat+DMSO |
| | | PAM | iTat+PAM |

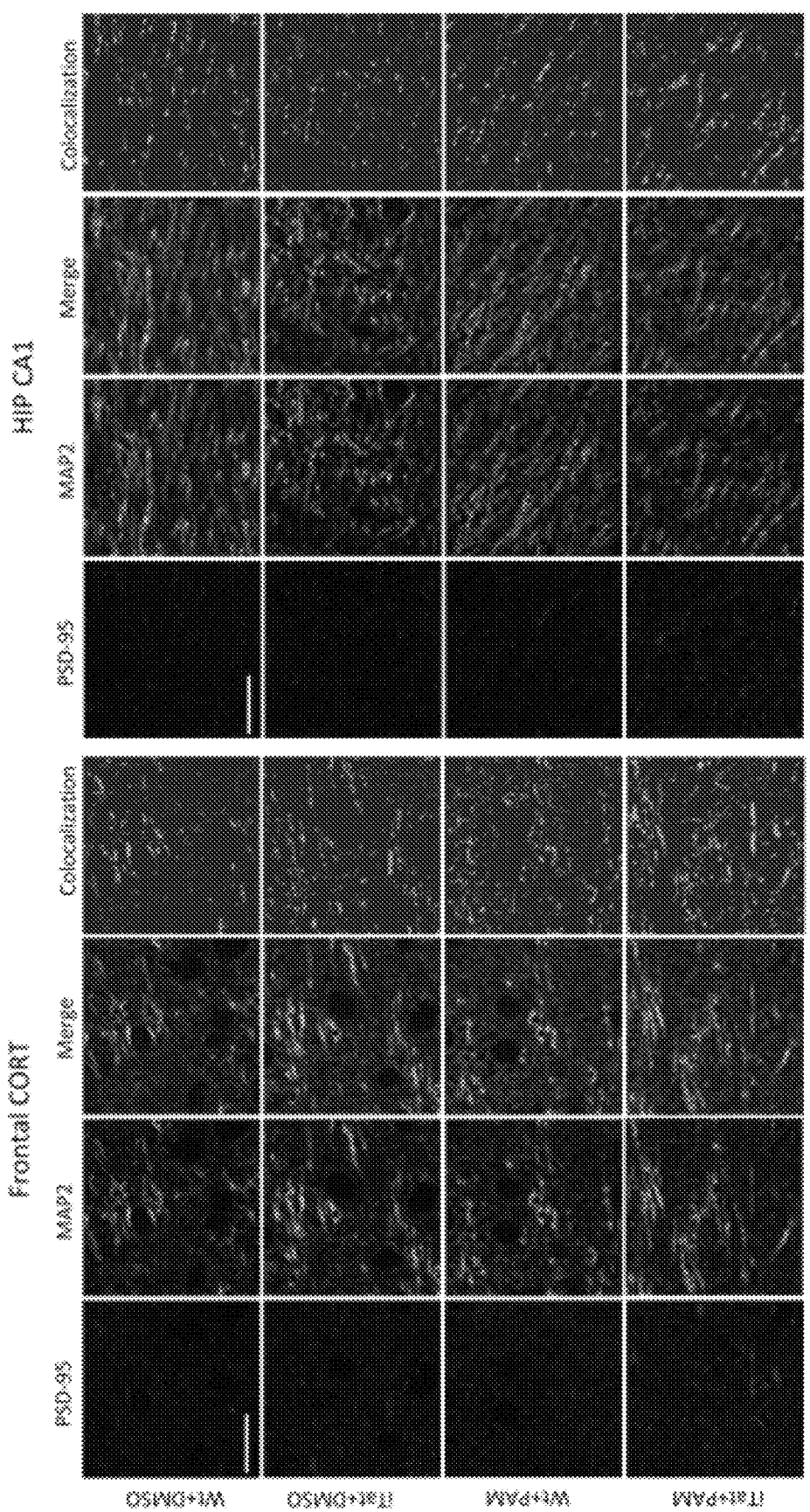

FIG. 2A Experimental groups

FIG. 3A Experimental groups

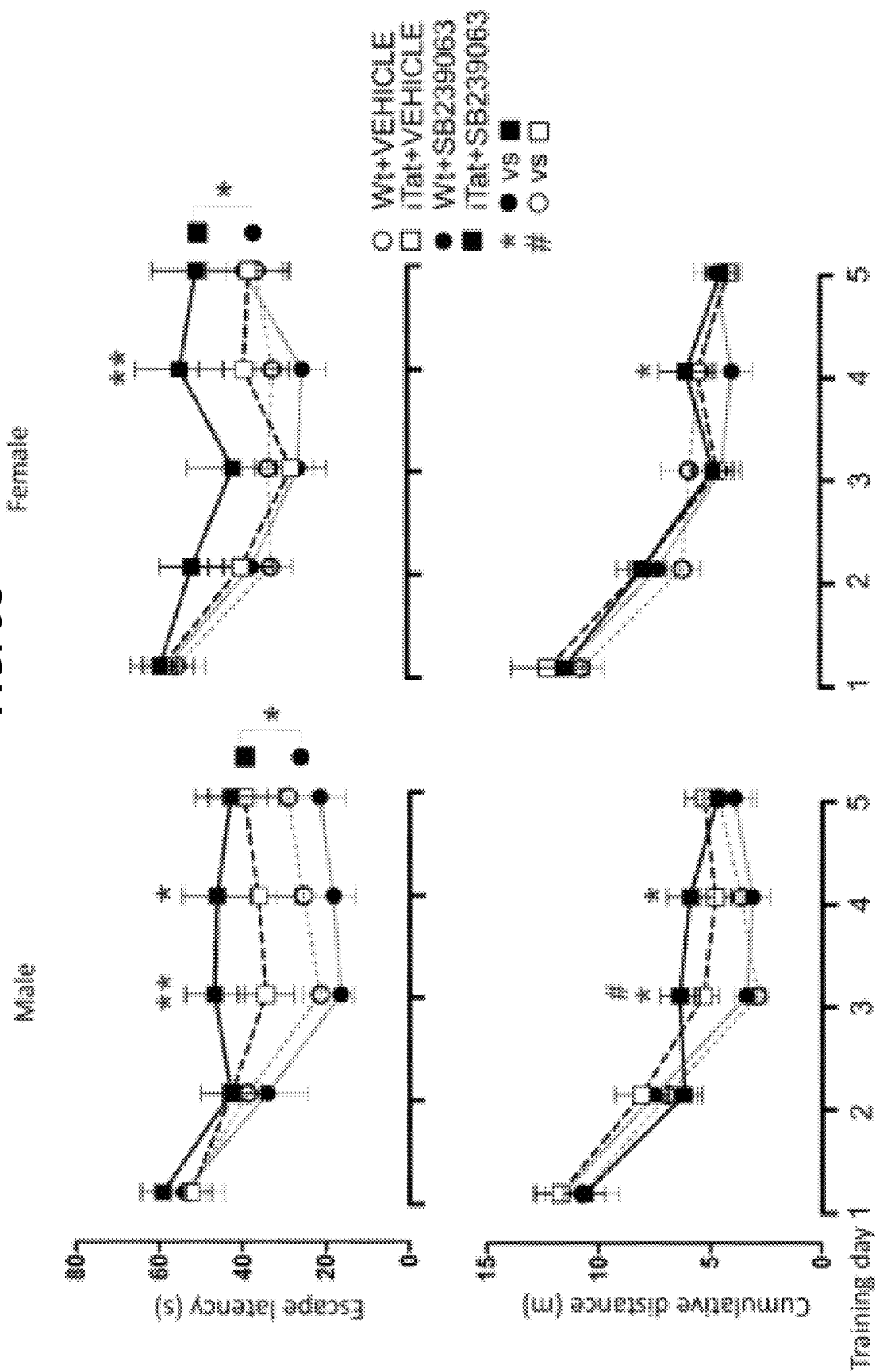

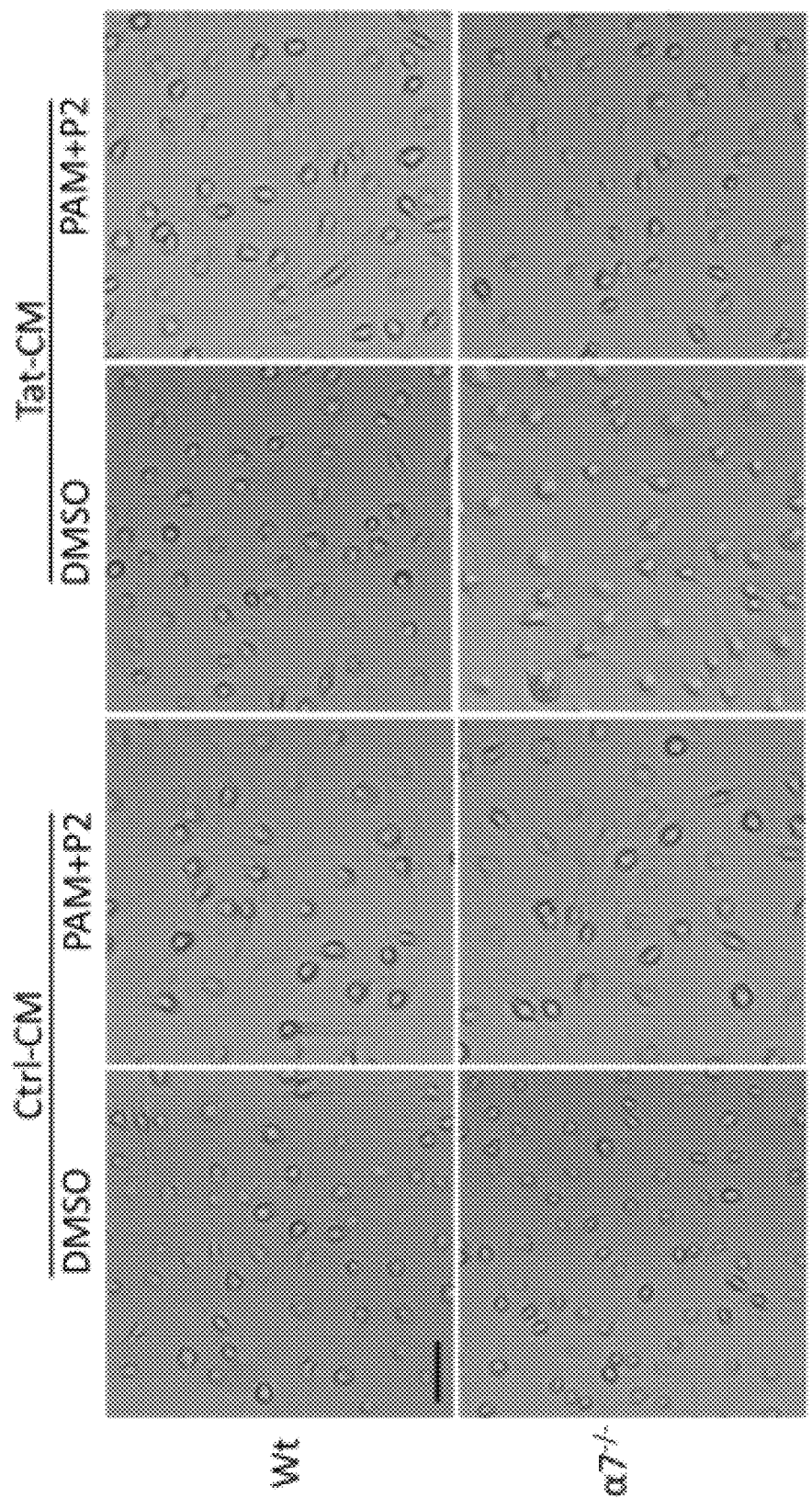

Neuron/astrocyte co-culture

Neuron/astrocyte co-culture

CORT

HIP

METHODS OF TREATING HIV-ASSOCIATED NEUROLOGICAL DISORDERS (HAND)

CROSS REFERENCE TO RELATED APPLICATIONS

This application claims the benefit of U.S. Provisional Application No. 63/124,372, filed Dec. 11, 2020, which is incorporated by reference herein in its entirety.

GOVERNMENT SUPPORT

This disclosure was made with government support under grants R01DA043162 and R01NS094108 awarded by the United States National Institutes of Health. The government has certain rights in the disclosure.

SEQUENCE LISTING

A computer readable form of the Sequence Listing is filed with this application by electronic submission and is incorporated into this application by reference in its entirety. The Sequence Listing is contained in the ASCII text file created on Dec. 9, 2021, having the file name "20-1934-US_Sequence-Listing_ST25.txt" and is 6 kb in size.

BACKGROUND OF THE DISCLOSURE

Field of the Disclosure

This disclosure generally relates to methods of treating HIV-associated neurological disorders (HAND), in particular, to methods of treating HAND comprising administering an effective dose of a positive allosteric modulator (PAM) of α7 nicotinic acetylcholine receptor.

Description of Related Art

Positive allosteric modulator of α7 nicotinic acetylcholine receptor significantly alleviated behavioral impairments, neuroinflammation, and neuronal injury in a model of HIV-associated neurological disorders through p38 MAPK signaling pathway. Combined antiretroviral therapy (cART) has effectively suppressed HIV replication and improved immune function as well as prolonged the lifespan of HIV-infected people.[1-5] However, HIV-associated neurocognitive disorders (HAND) have become more prevalent. The neurological manifestations include slowed locomotor activity, impaired learning and memory, and the neuropathological hallmarks are astrocyte/microglia activation, chronic neuroinflammation, and comprised neuronal integrity.[6-15] None of the antiretrovirals that are used in the current cART regimens have shown significant penetrance into the CNS and have provided effective treatments for HAND.[16-19]

HIV viral protein Tat is a major pathogenic factor for HAND. It is secreted from HIV-infected microglia and astrocytes and taken up by neurons[20-24] and detected in the brain of HIV-infected people who are cART naïve and who are actively treated with cART.[25-27] Tat expression activates glial fibrillary acidic protein (GFAP) expression in astrocytes through a cascade of transcription factors such as STAT3, early growth response 1 and p300 and causes astrocyte dysfunction and decreases neuron survival.[28-32] In addition, Tat expression alters autophagy, endoplasmic reticulum stress, lysosomal exocytosis, neurite growth, and neurogenesis.[33-37] Importantly, Tat expression in the brain of doxycycline-inducible astrocyte-specific HIV Tat transgenic mice (iTat) in the absence of HIV infection leads to locomotor, learning and memory deficits[38-46], and astrocyte/microglia activation, chronic neuroinflammation and loss of neuronal integrity[30,38,41,45], the consistent neurological and neuropathological hallmarks of HAND in the era of cART.

Nicotinic acetylcholine receptors (nAChR) are expressed throughout the peripheral and central nervous system, and they respond/bind to endogenous agonist neurotransmitter acetylcholine or exogenous agonist drug nicotine.[47,48] One of the most abundant nAChR is homomeric α7 nAChR, which is both ionotropic and metabotropic and is predominantly expressed in neurons and glia of cortex and hippocampus.[49,50] The ionotropic feature of α7 nAChR is the fast desensitization rate, characterized by very short agonist-induced onset duration and rapid decay with a long-lasting desensitized state.[50] The metabotropic feature is related to M3-M4 intracellular loop[51], which involves multiple cellular signaling pathways including MAPK, PLC-RhoA, JAK2-STAT3 and PI3K-Akt and modulates synaptogenesis and growth in neural cells and inflammatory response in immune cells.[52-60] α7 nAChR is involved in several neurological disorders such as Alzheimer's disease[49], schizophrenia[61], drug addiction[62,63], depression[64] and pain.[65] It has been proposed as potential therapeutic targets for Alzheimer's disease[49], addiction[66], schizophrenia[66,67], ischemic[68] and traumatic brain injury.[69] α7 nAChR has also been shown to be involved in HIV gp120 or gp41 neurotoxicity.[70-72] However, little is known about its roles in HAND and its potential as a therapeutic target for treating HAND.

SUMMARY

In the present disclosure, the roles of α7 nAChR in HAND were determined. PNU-120596, a prototype-II and highly selective α7 nAChR positive allosteric modulator (PAM)[50,73-75] was used in the surrogate HAND model iTat mice to determine if PAM PNU-120596 treatment would lead to any changes in Tat-induced behavioral impairments and neuropathologies. In addition, α7 nAChR knockout mice were used and determined the direct roles of α7 nAChR in Tat neurotoxicity. Furthermore, it was determined whether and which MAPK signaling pathway(s) were involved in the interplay between Tat neurotoxicity and α7 nAChR activation. Lastly, individual primary mouse cortical cultures and neuron-astrocytes co-cultures were used to assess the relative contribution of neurons, astrocytes and microglia to the interplay among Tat neurotoxicity, α7 nAChR activation and p38 MAPK signaling pathway. Based on the determinations, a method of treatment and compositions were discovered and were found to be surprisingly useful.

In an aspect, the present disclosure provides methods of treating HIV-associated neurological disorders (HAND) in a subject, wherein the method comprises administering an effective dose of a positive allosteric modulator (PAM) of α7 nicotinic acetylcholine receptor. In some embodiments, the positive allosteric modulator (PAM) of α7 nicotinic acetylcholine receptor is selected from the group consisting of: AVL-3288, NS1738, LY2087101, JWX-A0108, Genistein, 5-hydroxyindole, Ivermectin, PNU-120596, A-867744, TQS, JNJ-1930942, RO5126946, 4BP-TQS, and SB-206553. In certain embodiments, the positive allosteric modulator (PAM) of α7 nicotinic acetylcholine receptor is a type-II PAM selected from the group consisting of PNU-120596, A-867744, TQS, JNJ-1930942, RO5126946, 4BP- TQS, and SB-206553. In an embodiment, the positive allosteric modulator (PAM) of α7 nicotinic acetylcholine receptor is PNU-120596.

In some embodiments of the methods disclosed herein, the effective dose of the PAM of α7 nicotinic acetylcholine receptor comprises about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per day. In certain embodiments, the effective dose of the PAM of α7 nicotinic acetylcholine receptor comprises about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 6.0 mg/kg, about 7.0 mg/kg, about 8.0 mg/kg, about 9.0 mg/kg, about 10 mg/kg about 15 mg/kg, about 20 mg/kg, about 25 mg/kg, about 30 mg/kg, about 35 mg/kg, about 40 mg/kg, about 45 mg/kg, or about 50 mg/kg per day. In some embodiments, the effective dose of the PAM of α7 nicotinic acetylcholine receptor results in a serum concentration in the subject of about 0.1 μM, about 0.2 μM, about 0.3 μM, about 0.4 μM, about 0.5 μM, about 0.6 μM, about 0.7 μM, about 0.8 μM, about 0.9 μM, about 1.0 μM, about 2.0 μM, about 3.0 μM, about 4.0 μM, about 5.0 μM, about 6.0 μM, about 7.0 μM, about 8.0 μM, about 9.0 μM, or about 10 μM.

In some embodiments, the method further comprises administering to the subject an effective combined antiretroviral therapy (cART). In certain embodiments, the combined antiretroviral therapy (cART) refers to a treatment that uses a combination of two to three or more drugs to treat HIV infection. In some embodiments, the effective combined antiretroviral therapy comprises one or more of a nucleotide reverse transcriptase inhibitor (NRTI), a non-nucleotide reverse transcriptase inhibitor (NNRTI), a protease inhibitor (PI), and/or an integrase inhibitor. In certain embodiments, the nucleotide reverse transcriptase inhibitor (NRTI) is selected from one or more of abacavir, emtricitabine, lamivudine, tenofovir disoproxil fumarate, or zidovudine. In certain embodiments, the non-nucleotide reverse transcriptase inhibitor (NNRTI) is selected from one or more of doravirine, efavirenz, etravirine, nevirapine, or rilpivirine. In certain embodiments, the protease inhibitor (PI) is selected from one or more of atazanavir, darunavir, fosamprenavir, ritonavir, saquinavir, or tipranavir. In certain embodiments, the integrase inhibitor is selected from one or more of dolutegravir, or raltegravir.

In certain embodiments, the method results in improved mood, psychiatric benefits, improved locomotor functions, improved learning, and/or improved memory deficits in the subject.

In another aspect, this disclosure provides compositions comprising a positive allosteric modulator (PAM) of α7 nicotinic acetylcholine receptor and one or more of a nucleotide reverse transcriptase inhibitor (NRTI), a non-nucleotide reverse transcriptase inhibitor (NNRTI), a protease inhibitor (PI), and/or an integrase inhibitor. In certain embodiments, the positive allosteric modulator (PAM) of α7 nicotinic acetylcholine receptor is selected from the group consisting of the positive allosteric modulator (PAM) of α7 nicotinic acetylcholine receptor is selected from the group consisting of: AVL-3288, NS1738, LY2087101, JWX-A0108, Genistein, 5-hydroxyindole, Ivermectin, PNU-120596, A-867744, TQS, JNJ-1930942, RO5126946, 4BP-TQS, and SB-206553. In certain embodiments, the positive allosteric modulator (PAM) of α7 nicotinic acetylcholine receptor is a type-II PAM selected from the group consisting of PNU-120596, A-867744, TQS, JNJ-1930942, RO5126946, 4BP-TQS, and SB-206553. In an embodiment, the positive allosteric modulator (PAM) of α7 nicotinic acetylcholine receptor is PNU-120596.

In certain embodiments of the compositions as disclosed herein, the nucleotide reverse transcriptase inhibitor (NRTI) is selected from one or more of abacavir, emtricitabine, lamivudine, tenofovir disoproxil fumarate, or zidovudine; the non-nucleotide reverse transcriptase inhibitor (NNRTI) is selected from one or more of doravirine, efavirenz, etravirine, nevirapine, or rilpivirine; the protease inhibitor (PI) is selected from one or more of atazanavir, darunavir, fosamprenavir, ritonavir, saquinavir, or tipranavir; and the integrase inhibitor is selected from one or more of dolutegravir, or raltegravir.

BRIEF DESCRIPTION OF THE DRAWINGS

The following detailed description of the embodiments of the present disclosure can be best understood when read in conjunction with the following drawings.

FIG. 1A-FIG. 1G show the effects of PAM on HIV-1 Tat-induced behavioral impairments and neuropathologies. Wt or iTat mice of 3-4 months old were fed with doxycycline (Dox)-containing food pellets and injected s.c. with PAM PNU-125096 (15 mg/kg/day) or its solvent DMSO control (FIG. 1A), and grouped by sex (n=6-11/group, FIG. 1B). The mice were subject to Open Field Test (OPT, FIG. 1C) and Morris Water Maze (MWM) test (training stage, FIG. 1D), and the behavioral indices were determined by the Anymaze software. During the behavioral tests, Dox-containing food pellet feeding continued ad libitum, PNU-125096 was administrated within five hours following each behavioral test. On day 21, one day after the last behavioral test, all mice were euthanized, cortex (CORT) and hippocampus (HIP) were dissected out to determine expression of synaptophysin (SYP), PSD-95, GFAP and Iba-1, and total and phosphorylated p38, JNK, and ERK by Western blotting (FIG. 1E). Protein expression was quantified by densitometry and normalized to the loading control β-actin and calculated using Wt+DMSO as a reference, which was set at 1 (FIG. 1F) (n=6/group, three males and three females). Immunofluorescent staining was performed for PSD-95 and MAP2 expression (FIG. 1G, scale bars: 20 μm). Sub-regions in Frontal CORT and HIP CA1 were chosen as representative region for CORT and HIP, respectively. $p<0.05$ was considered significant and marked as *, # or $ for comparisons among different groups; $p<0.01$ and $p<0.001$ were both considered highly significant and marked as  and *, respectively.

FIG. 2A-FIG. 2F show the effects of α7 nAChR knockout on PAM neuroprotection against Tat-induced behavioral impairments and neuropathologies. A similar experimental scheme was performed as FIG. 1A except for using α7 nAChR knockout mice ($α7^{-/-}$) and $α7^{-/-}$iTat mice, which were obtained by cross breeding $α7^{-/-}$ mice with iTat mice and that the mice in all groups (FIG. 2A) were receiving Dox-containing food pellets and PAM injections (n=6-11/group). Similar behavioral Open field Test (FIG. 2B), Morris Water Maze training test (training stage, FIG. 2C), and Western Blotting (FIG. 2D & FIG. 2E) were performed (n=6/group, three males and three females). Immunofluorescent staining was also performed for PSD-95 and MAP2 (FIG. 2F, scale bars: 20 μm). GT: genotype. p<0.05 was considered significant and marked as *, # or $ for comparisons among different groups; p<0.01 and p<0.001 were both considered highly significant and marked as  and *, respectively.

FIG. 3A-FIG. 3F show the effects of p38 MAPK inhibitor SB239063 on Tat-induced behavioral impairments and neuropathologies. A similar experimental scheme was performed as FIG. 1A except for using i.p. injection of p38 MAPK inhibitor SB239063 (15 mg/kg/day) in place of s.c. injection of PAM PNU-125096 for mice in all groups (FIG. 3A, n=7-12/group). Similar behavioral Open field Test (FIG. 3B), Morris Water Maze test (training stage, C), Western Blotting (FIG. 3D & FIG. 3E, n=6/group, only males; Results from females were shown in FIG. 10), and immunofluorescent staining was performed for PSD-95 and MAP2 (FIG. 3F, scale bars: 20 μm). p<0.05 was considered significant and marked as *, or # for comparisons among different groups; p<0.01 and p<0.001 were both considered highly significant and marked as  and *, respectively.

FIG. 4A-FIG. 4G show the response of primary neurons, microglia, astrocytes, and neuron-astrocyte co-cultures to Tat and PAM. Primary neurons, microglia, astrocytes were isolated from one-day old pups of Wt and α7$^{-/-}$ mice, treated with the conditioned medium from pcDNA3-transfected cells (Ctrl-CM) or pcDNA3-Tat-transfected cells (Tat-CM) and PNU-125096 (PAM, 1 μM) and an α7 agonist PNU-282987 (P2, 0.5 μM) for 24 hr, and harvested to determine expression of PSD-95, Iba-1, or GFAP, or p-p38, p38 and β-actin by Western blotting (FIG. 4A). Protein expression was quantitated as FIG. 1E (FIG. 4B). Primary neurons were also double immunostained for PSD-95 and MAP2 (FIG. 4C). The positive staining area of PSD-95 puncta was quantitated by image J (FIG. 4D). Primary microglia were visualized for their morphologies by microscopy before harvesting for cell lysates (FIG. 4E) and then skeletonized (FIG. 4F). The line shaped branches, indicative of the ramified stage, and their total length were quantified in (FIG. 4G). The cells with shorter, non-completely formed or no line shaped branches were recognized as more amoeba-like phenotypes which presented more often in only Tat treated Wt group and α7—with Tat treatment groups (FIG. 4A). Multiple independent repeats were used for statistical analysis (n=3/group for Western blotting; n=8/group for immunofluorescent staining, n=6/group for microglia morphology). p<0.05 was considered significant and marked as *; p<0.01 and p<0.001 were both considered highly significant and marked as  and *, respectively. Scale bars: 10 μm (FIG. 4C) and 50 μm (FIG. 4E).

FIG. 13A shows staining of entorhinal bulb, basal forebrain and frontal cortex. FIG. 13B shows staining of brain stem, cerebellum, and hippocampus. Scale bar: 500 μm.

DETAILED DESCRIPTION OF THE DISCLOSURE

Figures 1A, 1B:
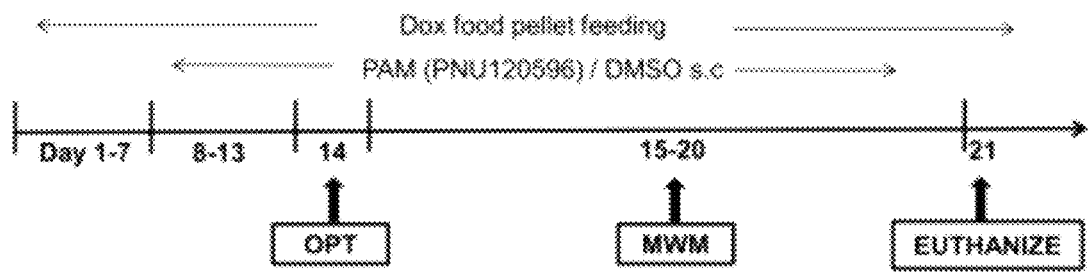
Figure 1C:
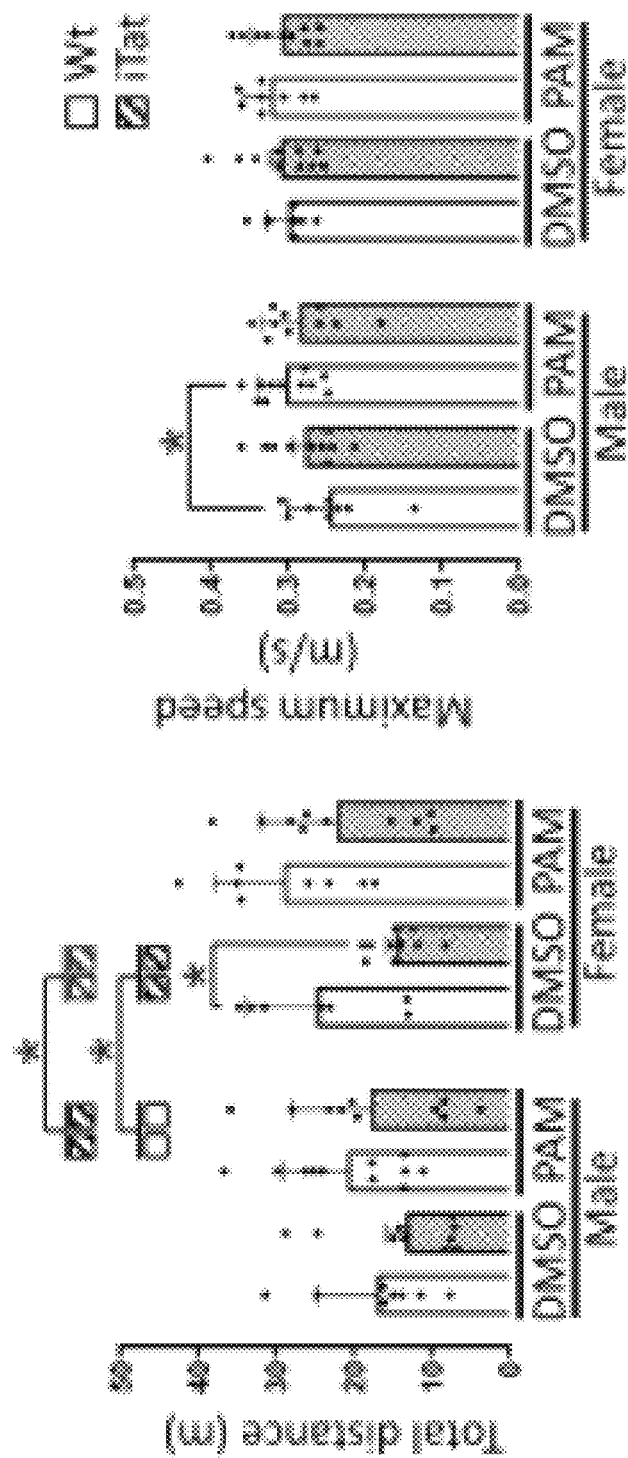

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

Before describing the present disclosure in detail, a number of terms will be defined. Unless otherwise required by context, singular terms shall include pluralities and plural terms shall include the singular. For example, the singular forms "a," "an," and "the" include plural referents unless the context clearly dictates otherwise.

It is noted that terms like "preferably," "commonly," and "typically" are not utilized herein to limit the scope of the claimed disclosure or to imply that certain features are critical, essential, or even important to the structure or function of the claimed disclosure. Rather, these terms are merely intended to highlight alternative or additional features that can or cannot be utilized in a particular embodiment of the present disclosure.

The terms "comprises" and variations thereof do not have a limiting meaning where these terms appear in the description and claims.

For the purposes of describing and defining the present disclosure it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the term "about" is used to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. Ranges and amounts can be expressed as "about" a particular value or range. About can also include the exact amount. Typically, the term "about" includes an amount that would be expected to be within experimental error. The term "about" includes values that are within 10% less to 10% greater of the value provided.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As utilized in accordance with the present disclosure, unless otherwise indicated, all technical and scientific terms shall be understood to have the same meaning as commonly understood by one of ordinary skill in the art.

This disclosure generally relates to methods and compositions for treating HIV-associated neurological disorders (HAND) in a subject. In an aspect, this disclosure relates to methods of treating HAND comprising administering an effective dose of a positive allosteric modulator (PAM) of α7 nicotinic acetylcholine receptor, optionally in conjunction with a combination anti-retroviral therapy. In another aspect, this disclosure relates to compositions comprising a positive allosteric modulator (PAM) of α7 nicotinic acetylcholine receptor and one or more of a nucleotide reverse transcriptase inhibitor (NRTI), a non-nucleotide reverse transcriptase inhibitor (NNRTI), a protease inhibitor (PI), and/or an integrase inhibitor.

As used herein, "HIV-associated neurocognitive disorders" or "HAND" refer to neurological disorders associated with HIV infection and AIDS. HANDs can present as a pattern of progressive deterioration of memory, cognition, behavior, and motor function in HIV-infected individuals during the late stages of the disease. Symptoms of HAND can fall into three broad categories: (1) Cognitive: problems in concentration (for example, difficulty following the thread of a conversation, short attention span, inability to complete routine tasks, and/or trouble finishing a sentence); memory loss (for example, trouble recalling appointments, medication schedules, agreements, and/or previous conversations); and/or a generalized slowdown in mental functions (for example, difficulty understanding and responding to questions, and/or a loss of sense of humor or wit). (2) Motor skills: poor coordination, weakness in legs, difficulty maintaining balance, tendency to drop things, decline in clarity of handwriting, and/or loss of bladder or bowel control. (3) Behavioral: personality changes (for example, increased irritability, apathy toward loved ones or life in general, loss of initiative, and/or withdrawal from social contact); mood swings (for example, depression, excitability, and/or emotional outbursts); impaired judgment (for example, impulsive decision-making, and/or loss of inhibitions); and/or symptoms of psychosis (for example, hallucinations, paranoia, disorientation, and/or sudden rages). HAND sub-classifications can include asymptomatic neurocognitive impairment (ANI), mild neurocognitive disorder (MND), and HIV associated dementia (HAD). In certain embodiments, the HIV-associated neurocognitive disorder may include, but is not limited to, asymptomatic neurocognitive impairment (ANI), minor neurocognitive disorder (MND), HIV-associated dementia (HAD), or a combination thereof. Table 1 below provides a summary of HAND sub-classifications.

TABLE 1

Summary of sub-classifications of HAND.

| | Neurocognitive Status[#] | Functional Status[*] | Prevalence in CART-treated HIV positive individuals |
|---|---|---|---|
| Asymptomatic Neurocognitive Impairment (ANI) | Impairment in ≥2 neurocognitive domains (≥1 SD) | No impairment/ interference in activities of daily living | about 30% |
| Mild Neurocognitive Disorder (MND) | Impairment in ≥2 neurocognitive domains (≥1 SD) | Impairment/ interference in activities of daily living | about 20-30% |
| HIV Associated Dementia (HAD) | Marked (≥2 SD) impairment in ≥2 neurocognitive domains | Marked impairment/ interference in activities of daily living | about 2-8% |

[#]Neurocognitive testing should include evaluating at least five domains including attention-information processing, language, abstraction-executive, complex perceptual motor skills, memory (including learning and recall) simple motor skills or sensory perceptual skills.
Appropriate norms must be available to determine the number of domains in which performance is below 1 standard deviation (SD).
[*]Functional status is typically evaluated by self report but may be corroborated by a collateral source. No agreed upon measures exist for HAND criteria.
Of note, for HAND diagnosis other etiology of dementia must be ruled out and confounding effect of substance use or psychiatric illness must be considered.
Adapted from:
Clifford et al., Lancet Infect Dis. 2013 Nov; 13(11): 976-986; and Saylor et al., Nat Rev Neurol. 2016 Apr; 12(4): 234-248.

Nicotinic acetylcholine receptors, or nAChRs, are receptor polypeptides that respond to the neurotransmitter acetylcholine, and can be found in the central and peripheral nervous system, muscle, and many other tissues of many organisms. The alpha-7 nicotinic receptor, also known as the α7 receptor, is a type of nicotinic acetylcholine receptor implicated in long-term memory, consisting entirely of α7 subunits. One approach to target alpha7 nAChRs is by positive allosteric modulation. Positive allosteric modulators (PAMs), can be classified and distinguished as type I and type II. Type I PAMs mainly enhance agonist-evoked peak currents without delaying desensitization and do not reactivate desensitized receptors, whereas type II PAMs can delay desensitization and reactivate desensitized receptors. In some embodiments, the positive allosteric modulator (PAM) of α7 nicotinic acetylcholine receptor used to treat HAND in a subject is a type-II PAM. In certain embodiments, the type-II PAM is selected from the group consisting of PNU-120596, A-867744, TQS, JNJ-1930942, RO5126946, 4BP-TQS, and SB-206553. In an embodiment, the positive allosteric modulator (PAM) of α7 nicotinic acetylcholine receptor is PNU-120596.

Non-limiting examples of type I α7 nAChR PAMs include, but are not limited to:

AVL-3288 ((E)-N-(4-chlorophenyl)-3-((4-chlorophenyl) amino)-2-(3-methylisoxazol-5-yl) acrylamide), which also named XY4083 or CCMI.
NS1738 (1-(5-chloro-2-hydroxy-phenyl)-3-(2-chloro-5-trifluoromethyl-phenyl)-urea).
LY2087101 ([2-[(4-fluorophenyl)amino]-4-methyl-5-thiazolyl]-3-thienylmethanone).
JWX-A0108 6-(2-chloro-6-methylphenyl)-2-((3-fluoro-4-methyl phenyl)amino)thiazolo[4,5-d]pyrimidin-7(6H)-one.
Genistein ($C_{15}H_{10}O_8$) 5,7-Dihydroxy-3-(4-hydroxyphenyl)-4H-1-benzopyran-4-one.
5-hydroxyindole ($C_8H_7NO$) 1H-indol-5-ol.
Ivermectin ($C_{48}H_{74}O_{14}$) (1R,4S,5'S,6R,6'R,8R,10E,12S,13S,14E,16E,20R,21R,24S)-6'-[(2S)-butan-2-yl]-21,24-dihydroxy-12-[(2R,4S,5S,6S)-5-[(2S,4S,5S,6S)-5-hydroxy-4-methoxy-6-methyloxan-2-yl]oxy-4-methoxy-6-methyloxan-2-yl]oxy-5',11,13,22-tetramethylspiro[3,7,19-trioxatetracyclo[1 5.6.1.14, 8.020,24]pentacosa-10,14,16,22-tetraene-6,2'-oxane]-2-one.

Non-limiting examples of type II α7 nAChR PAMs include, but are not limited to:

PNU-120596 (1-(5-chloro-2,4-dimethoxy-phenyl)-3-(5-methyl-isoxazol-3-yl)-urea).
A-867744 (4-(5-(4-chlorophenyl)-2-methyl-3-propionyl-1H-pyrrol-1-yl)benzenesulfonamide).
TQS (4-naphthalene-1-yl-3a,4,5,9b-tetrahydro-3H-cyclopenta[c]quinoline-8-sulfonic acid amide).
JNJ-1930942 (2-[[4-fluoro-3-(trifluoromethyl)phenyl] amino]-4-(4-pyridinyl)-5-thiazolemethanol).
RO5126946 ((5-chloro-N-[(1S,3R)-2,2-dimethyl-3-(4-sulfamoyl-phenyl)-cyclopropyl]-2-methoxy-benzamide).
4BP-TQS (4-(4-bromophenyl)-3a,4,5,9b-tetrahydro-3H-cyclopenta[c]quinoline-8-sulfonamide), also called GAT-107.
SB-206553 ($C_{17}H_{17}ClN_4O$) 1-methyl-N-pyridin-3-yl-6,7-dihydropyrrolo[2,3-f]indole-5-carboxamide; hydrochloride.

As used herein, the terms "treat," "treatment," or "treating" refer to a method of reducing the effects of a disease or condition or symptom of the disease or condition, or alleviating a symptom of a disease or condition (e.g., a disease or condition involving an HIV-associated neurocognitive disorder in a subject in need thereof). Treating can be an approach for obtaining beneficial or desired results in a subject's condition. The term "subject" as used herein includes human and non-human animal subjects. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. Thus, in the methods disclosed herein, treatment can refer to a 5%, 10%, 20%, 30%, 40%, 50%, 60%, 70%, 80%, 90%, or 100% reduction in the severity of an established disease or condition or symptom of the disease or condition. For example, a method of treating a disease is considered to be a treatment if there is a 5% reduction in one or more symptoms of the disease in a subject as compared to a control. Thus, the reduction can be a 5%, 10%, 20%, 30%, 40%, 50%, 60%, 70%, 80%, 90%, 100% or any percent reduction between 5% and 100% as compared to native or control levels. It is understood that treatment does not necessarily refer to a cure or complete ablation of the disease, condition, or symptoms of the disease or condition. After HAND is diagnosed in a subject, a medical professional or team of medical professionals will recommend one or several treatment options. In determining a treatment plan, factors to consider include the type and severity of HAND, as well as the patient's overall physical health. Patients with HAND typically are managed by a health care team made up of doctors from different specialties.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery can include, but are not limited to, the use of liposomal formulations, intravenous infusion, transdermal patches, etc. By "co-administer" it is meant that a first compound described herein is administered at the same time, just prior to, or just after the administration of a second compound described herein.

As used herein, the term "effective dose" refers to that amount of a composition or compound that results in an observable designated effect. Actual dosage levels of active ingredients in an active composition of the presently disclosed subject matter can be varied so as to administer an amount of the active composition or compound that is effective to achieve the designated response for a particular subject and/or application. The selected dosage level can vary based upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are also contemplated herein. In some embodiments, an effective dose results in improved mood, psychiatric benefits, improved locomotor functions, improved learning, and/or improved memory deficits in the subject.

In some embodiments, an effective dose comprises about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per day. In certain embodiments, an effective dose comprises about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 6.0 mg/kg, about 7.0 mg/kg, about 8.0 mg/kg, about 9.0 mg/kg, about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg per day. In some embodiments, an effective dose results in a serum concentration in the subject of about 0.01 $\mu$M to about 3,000 $\mu$M. For example about 0.1 $\mu$M, about 0.2 $\mu$M, about 0.3 $\mu$M, about 0.4 $\mu$M, about 0.5 $\mu$M, about 0.6 $\mu$M, about 0.7 $\mu$M, about 0.8 $\mu$M, about 0.9 $\mu$M, about 1.0 $\mu$M, about 2.0 $\mu$M, about 3.0 $\mu$M, about 4.0 $\mu$M, about 5.0 $\mu$M, about 6.0 $\mu$M, about 7.0 $\mu$M, about 8.0 $\mu$M, about 9.0 $\mu$M, or about 10 $\mu$M. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art. In some embodiments, the positive allosteric modulator (PAM) of $\alpha$7 nicotinic acetylcholine receptor is administered in an amount from about 0.001 mg/kg body weight to about 100 mg/kg body weight per day. In certain embodiments, daily dosages may be in the range of 0.01 mg/kg body weight to about 50 mg/kg body weight per day. A typical effective dose for adults will be in the range of about 0.1-1000 mg/day of a positive allosteric modulator (PAM) of $\alpha$7 nicotinic acetylcholine receptor, for example, such as about 1-500 mg/day, or about 1-100 mg/day or about 1-50 mg/day.

In certain embodiments, a positive allosteric modulator (PAM) of $\alpha$7 nicotinic acetylcholine receptor can be administered to a subject once per day, twice per day, three times per day, four times per day, or more. In some embodiments, the positive allosteric modulator (PAM) of $\alpha$7 nicotinic acetylcholine receptor is administered as an extended release formulation. The appropriate dose, frequency, and duration can be modified to address the particular needs of a particular subject by taking into account factors including, but not limited to, the age, gender, weight, and health of the subject; the severity, extent, and type of HAND. In some embodiments, the length of treatment can be less than 1 week to 12 months, or more than 12 months. In certain embodiments, treatment duration can be indefinite. In some embodiments, treatment duration can be until disease remission.

In some embodiments, the effective dose of a positive allosteric modulator (PAM) of $\alpha$7 nicotinic acetylcholine receptor is administered in a single dose or in multiple doses. In some embodiments, the effective dose of a positive allosteric modulator (PAM) of α7 nicotinic acetylcholine receptor is administered as an extended release formulation. In certain embodiments, the effective dose of a positive allosteric modulator (PAM) of α7 nicotinic acetylcholine receptor is administered one time per day, two times per day, three times per day, or four times per day. Dosing frequency will depend upon the pharmacokinetic parameters of the positive allosteric modulator (PAM) of α7 nicotinic acetylcholine receptor being used. Typically, a clinician will administer the composition until a dosage is reached that achieves the desired effect. In certain embodiments, the composition is administered about every 24, 12, 8, 6, or 4 hours. In another embodiment, the composition is administered 2 or 3 times during at least one 24 hour period. In some embodiments, the composition is administered once per day, two times per day, three times per day, or four times a day. In certain embodiments, the length of treatment can be less than 1 week to 12 months, or more than 12 months. For example, the length of treatment can be from about 1 week to about 4 weeks, from about 2 weeks to about 6 weeks, from about 4 weeks to about 8 weeks, from about 1 month to about 3 months, from about 2 months to about 4 months, from about 3 months to about 6 months, from about 6 months to about 12 months, or more than 12 months. In some embodiments, treatment duration can be until disease remission, for example, from about 1 month to about 24 months, or more than 24 months. In some embodiments, the subject is treated for about 1 month, about 2 months, about 3 months, about 4 months, about 5 months, about 6 months, about 7 months, about 8 months, about 9 months, about 10 months, about 11 months, about 1 year, about 2 years, or more than 2 years. In certain embodiments, the subject is treated indefinitely.

In some embodiments, the methods of treating HAND comprise administering an effective dose of a positive allosteric modulator (PAM) of α7 nicotinic acetylcholine receptor in conjunction with a combined anti-retroviral therapy. As used herein, combined antiretroviral therapy (cART), or combination therapy, or highly active antiretroviral therapy (HAART) refer to the use of a combination of HIV medicines, and typically includes three antiretroviral drugs from at least two different HIV drug classes. In some embodiments, the combined antiretroviral therapy (cART) refers to a treatment that uses a combination of two to three or more drugs to treat HIV infection. In certain embodiments, an effective combined antiretroviral therapy comprises one or more of a nucleotide reverse transcriptase inhibitor (NRTI), a non-nucleotide reverse transcriptase inhibitor (NNRTI), a protease inhibitor (PI), and/or an integrase inhibitor. In some embodiments, a nucleotide reverse transcriptase inhibitor (NRTI) is selected from one or more of abacavir, emtricitabine, lamivudine, tenofovir disoproxil fumarate, or zidovudine. In certain embodiments, a non-nucleotide reverse transcriptase inhibitor (NNRTI) is selected from one or more of doravirine, efavirenz, etravirine, nevirapine, or rilpivirine. In some embodiments, a protease inhibitor (PI) is selected from one or more of atazanavir, darunavir, fosamprenavir, ritonavir, saquinavir, or tipranavir. In some embodiments, an integrase inhibitor is selected from one or more of dolutegravir, or raltegravir. In some embodiments, a cART can be any combination of the compounds/compositions as shown in Table 2.

TABLE 2

Examples of drugs for cART.

| Drug Class | Generic Name (Other names and acronyms) | Brand Name |
| --- | --- | --- |
| Nucleoside Reverse Transcriptase Inhibitors (NRTIs) NRTIs block reverse transcriptase, an enzyme HIV needs to make copies of itself. | abacavir (abacavir sulfate, ABC) | Ziagen |
| | emtricitabine (FTC) | Emtriva |
| | lamivudine (3TC) | Epivir |
| | tenofovir disoproxil fumarate (tenofovir DF, TDF) | Viread |
| | zidovudine_(azidothymidine, AZT, ZDV) | Retrovir |
| Non-Nucleoside Reverse Transcriptase Inhibitors (NNRTIs) NNRTIs bind to and later alter reverse transcriptase, an enzyme HIV needs to make copies of itself. | doravirine (DOR) | Pifeltro |
| | efavirenz (EFV) | Sustiva |
| | etravirine (ETR) | Intelence |
| | nevirapine (extended-release nevirapine, NVP) | Viramune Viramune XR (extended release) |
| | rilpivirine (rilpivirine hydrochloride, RPV) | Edurant |
| Protease Inhibitors (PIs) PIs block HIV protease, an enzyme HIV needs to make copies of itself. | atazanavir (atazanavir sulfate, ATV) | Reyataz |
| | darunavir (darunavir ethanolate, DRV) | Prezista |
| | fosamprenavir (fosamprenavir calcium, FOS-APV, FPV) | Lexiva |
| | ritonavir (RTV) *Although ritonavir is a PI, it is generally used as a pharmacokinetic enhancer as recommended in the Guidelines for the Use of Antiretroviral Agents in Adults and Adolescents with HIV and the Guidelines for the Use of Antiretroviral Agents in Pediatric HIV Infection. | Norvir |
| | saquinavir (saquinavir mesylate, SQV) | Invirase |
| | tipranavir (TPV) | Aptivus |

TABLE 2-continued

Examples of drugs for cART.

| Drug Class | Generic Name (Other names and acronyms) | Brand Name |
|---|---|---|
| Fusion inhibitors block HIV from entering the CD4 cells of the immune system. | enfuvirtide (T-20) | Fuzeon |
| CCR5 antagonists block CCR5 coreceptors on the surface of certain immune cells that HIV needs to enter the cells. | maraviroc (MVC) | Selzentry |
| Integrase inhibitors block HIV integrase, an enzyme HIV needs to make copies of itself. | dolutegravir (dolutegravir sodium, DTG) raltegravir (raltegravir potassium, RAL) | Tivicay Isentress Isentress HD |
| Attachment inhibitors bind to the gp120 protein on the outer surface of HIV, preventing HIV from entering CD4 cells. | fostemsavir (fostemsavir tromethamine, FTR) | Rukobia |
| Post-attachment inhibitors block CD4 receptors on the surface of certain immune cells that HIV needs to enter the cells. | ibalizumab-uiyk (Hu5A8, IBA, lbalizumab, TMB-355, TNX-355) | Trogarzo |
| Pharmacokinetic enhancers are used in HIV treatment to increase the effectiveness of an HIV medicine included in an HIV regimen. | cobicistat (COBI, c) | Tybost |
| Exemplary Combination HIV Medicines Combination HIV medicines contain two or more HIV medicines from one or more drug classes. | abacavir and lamivudine (abacavir sulfate/lamivudine, ABC/3TC) | Epzicom |
| | abacavir, dolutegravir, and lamivudine (abacavir sulfate/dolutegravir sodium/lamivudine, ABC/DTG/3TC) | Triumeq |
| | abacavir, lamivudine, and zidovudine (abacavir sulfate/lamivudine/zidovudine, ABC/3TC/ZDV) | Trizivir |
| | atazanavir and cobicistat (atazanavir sulfate/cobicistat, ATV/COBI) | Evotaz |
| | bictegravir, emtricitabine, and tenofovir alafenamide (bictegravir sodium/emtricitabine/tenofovir alafenamide fumarate, BIC/FTC/TAF) | Biktarvy |
| | darunavir and cobicistat (darunavir ethanolate/cobicistat, DRV/COBI) | Prezcobix |
| | darunavir, cobicistat, emtricitabine, and tenofovir alafenamide (darunavir ethanolate/cobicistat/emtricitabine/tenofovir AF, darunavir ethanolate/cobicistat/emtricitabine/tenofovir alafenamide, darunavir/cobicistat/emtricitabine/tenofovir AF, darunavir/cobicistat/emtricitabine/tenofovir alafenamide fumarate, DRV/COBI/FTC/TAF) | Symtuza |
| | dolutegravir and lamivudine (dolutegravir sodium/lamivudine, DTG/3TC) | Dovato |
| | dolutegravir and rilpivirine (dolutegravir sodium/rilpivirine hydrochloride, DTG/RPV) | Juluca |
| | doravirine, lamivudine, and tenofovir disoproxil fumarate (doravirine/lamivudine/TDF, doravirine/lamivudine/tenofovir DF, DOR/3TC/TDF) | Delstrigo |
| | efavirenz, emtricitabine, and tenofovir disoproxil fumarate (efavirenz/emtricitabine/tenofovir DF, EFV/FTC/TDF) | Atripla |
| | efavirenz, lamivudine, and tenofovir disoproxil fumarate (EFV/3TC/TDF) | Symfi |
| | efavirenz, lamivudine, and tenofovir disoproxil fumarate (EFV/3TC/TDF) | Symfi Lo |

TABLE 2-continued

Examples of drugs for cART.

| Drug Class | Generic Name (Other names and acronyms) | Brand Name |
|---|---|---|
| | elvitegravir, cobicistat, emtricitabine, and tenofovir alafenamide (elvitegravir/cobicistat/emtricitabine/ tenofovir alafenamide fumarate, EVG/ COBI/FTC/TAF) | Genvoya |
| | elvitegravir, cobicistat, emtricitabine, and tenofovir disoproxil fumarate (QUAD, EVG/COBI/FTC/TDF) | Stribild |
| | emtricitabine, rilpivirine, and tenofovir alafenamide (emtricitabine/rilpivirine/tenofovir AF, emtricitabine/rilpivirine/tenofovir alafenamide fumarate, emtricitabine/ rilpivirine hydrochloride/tenofovir AF, emtricitabine/rilpivirine hydrochloride/ tenofovir alafenamide, emtricitabine/ rilpivirine hydrochloride/tenofovir alafenamide fumarate, FTC/RPV/TAF) | Odefsey |
| | emtricitabine, rilpivirine, and tenofovir disoproxil fumarate (emtricitabine/rilpivirine hydrochloride/ tenofovir disoproxil fumarate, emtricit- abine/ rilpivirine/tenofovir, FTC/RPV/TDF) | Complera |
| | emtricitabine and tenofovir alafenamide (emtricitabine/tenofovir AF, emtricitabine/ tenofovir alafenamide fumarate, FTC/ TAF) | Descovy |
| | emtricitabine and tenofovir disoproxil fumarate (emtricitabine/tenofovir DF, FTC/TDF) | Truvada |
| | lamivudine and tenofovir disoproxil fumarate (Temixys, 3TC/TDF) | Cimduo |
| | lamivudine and zidovudine (3TC/ZDV) | Combivir |
| | lopinavir and ritonavir (ritonavir-boosted lopinavir, LPV/r, LPV/ RTV) | Kaletra |

In some embodiments, the composition is a "pharmaceutical composition" or "therapeutic composition." The terms "pharmaceutical composition" or "therapeutic composition" as used herein refer to a compound or composition capable of inducing a desired therapeutic effect when properly administered to a subject. For example, in a subject with HAND a therapeutic composition would result in improved mood, psychiatric benefits, improved locomotor functions, improved learning, and/or improved memory deficits in the subject.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

In some embodiments, the compositions as disclosed herein can be administered orally, parenterally, transdermally, topically, transmucosally, by inhalation, by suppository, by buccal delivery, by sublingual delivery, by ophthalmic delivery, or by injection (subcutaneous injection, subdermal injection, intramuscular injection, depot administration, or intravenous injection). In certain embodiments, the composition is administered orally. In some embodiments, the oral composition is an extended release composition (i.e., designed to slowly release over an extended period of time). Extended release compositions can comprise of sustained-release (SR), or controlled-release (CR) dosage. Sustained-release maintains drug release over a sustained period, but not at a constant rate. Controlled-release maintains drug release over a sustained period at a nearly constant rate. Sustained-release dosage forms are dosage forms designed to release a drug at a predetermined rate in order to maintain a constant drug concentration for a specific period of time with minimum side effects.

EXAMPLES

Materials and Methods
Mouse and Drug Administration:

Doxycycline (Dox)-inducible and astrocyte-specific HIV-1 Tat-transgenic mice (iTat) were generated as previously described.[38] Wild-type (Wt, C57BL/6) and α7 nAChR knockout mice ($α7^{-/-}$, B6.129S7-Chrna$^{tm1Bal/J}$) were purchased from the Jackson Laboratory (Bar Harbor, ME). All the animal procedures were approved by the Institutional Animal Care and Use Committee. Mice were housed with a 12-hour light and 12-hour dark photoperiod and provided water and food ad libitum. $α7^{-/-}$ iTat mice were generated by cross breeding iTat mice with $α7^{-/-}$ mice. $α7^{-/-}$ genotyping was slightly modified with the JumpStart™ Taq DNA Polymerase-based PCR (JumpStart™ Taq DNA Polymerase, Sigma, catalog #D9307). Briefly, genomic DNA was extracted from the mouse tail and used a template for PCR with a program of 94° C. for 1 min, 35 cycles of 94° C. for 30 sec; 55° C. for 30 sec, and 72° C. for 1 min, and 72° C. for 1 min using primers 5'-TTC CTG GTC CTG CTG TGT TA-3' (SEQ ID NO:25) and 5'-ATC AGA TGT TGC TGG CAT GA-3' (SEQ ID NO:26) for $α7^{+/+}$ Wt mice, and 5'-TTC CTG GTC CTG CTG TGT TA-3' (SEQ ID NO:27) and 5'-CCC TTT ATA GAT TCG CCC TTG-3' (SEQ ID NO:28) for $α7^{-/-}$ knockout mice). Mice of 10-14 weeks old with body weights of 20-35 grams were fed with Dox-containing diet (0.625 g/kg, Envigo, catalog #TD.01306) as stated. PNU-120596 hydrate (Alomone, catalog #P-350) was dissolved in DMSO and s.c. injected (15 mg/kg/day, 40 μl for male mice with an average weight of 30 grams and 30 μl for female mice with an average weight of 22 grams to ensure minimal DMSO-associated toxicity).[76] SB239063 (Tocris, catalog #1962) was dissolved in a mixture of 0.8% DMSO, 32% PEG400 (Sigma-Aldrich, catalog #91893) and 67% saline and i.p. injected (15 mg/kg/day, 200 μl for male mice and 150 μl for female mice).[77]

Behavioral Tests:

Open Field Test (OPT) and Morris Water Maze (MWZ) were performed sequentially using a computerized video tracking system (Anymaze, Stoelting) to determine the spontaneous locomotor activity and spatial learning and memory, respectively. For OPT, each mouse was allowed to move freely around a clear acrylic chamber (40.5×40.5×30.5 cm) for 10 minutes. Travel distance and maximum speed was determined by the AnyMaze software. For MWZ, a circle pool (1.2 m diameter) surrounded with a curtain was divided into four equal quadrants, and four signs with different shape were fixed onto the middle of each quadrant wall above the opaque water (24±1° C.). A hidden platform (1.5 cm below water surface) was put into a certain quadrant. Two stages consisting of 5-day training and probe test were carried out. In the training stage, four trials with a 15-20 minute interval were conducted in the every-day training, and for each trial mice were allowed to freely seek the platform within 90 seconds right after they were randomly put into one quadrant facing to the pool wall. If the mice found the platform within 90 seconds, 10 seconds would be added to allow them staying on the platform for memorizing, however, if failed, they would be directed toward the platform and allowed to stay on it for 15 seconds. Mice that were immobile or floating and unable to find the platform during the training stages were excluded from the experiments. Probe test was carried out on the next day following the 5-day training stage with a 60 seconds trial, and the platform was removed to prevent the mice from climbing onto it during the testing. One day after the behavioral tests, mice were euthanized and the brains were harvested.

Western Blotting:

A RIPA buffer (50 mM Tris.HCl, pH 8.0, 280 mM NaCl, 0.5% NP-40, 1% $C_{24}H_{39}NaO_4$, 0.2 mM EDTA, 2 mM EGTA and 10% glycerol) supplemented with protease inhibitors (Millipore-Sigma, catalog #S8830) and phosphatase inhibitors (Millipore-Sigma, catalog #4906845001) was used to lyse the brain tissues and cultured cells with brief sonication on ice. Protein concentrations of the lysates were determined using a Bio-Rad DC protein assay kit (Bio-Rad, catalog #5000111). Lysates were denatured in the SDS-PAGE loading buffer at 100° C. for 10 min, then electrophoretically separated by 8-15% SDS-PAGE, blotted onto 0.45 μm polyvinylidene fluoride membrane (GE Healthcare Life Sciences, catalog #10600023), and probed using appropriate antibodies against PSD-95 (Abcam, catalog #ab18258, and 1:2000 dilution), SYP (Abcam, catalog #ab8049, and 1:1000 dilution), Iba-1 (Wako, catalog #016-20001, and 1:500 dilution) and GFAP (DAKO, catalog #z330s, and 1:2000 dilution), p-p38 (Santa Cruz, catalog #sc-166182, and 1:1000 dilution), p38 (Santa cruz, catalog #sc-535, and 1:1000 dilution), p-JNK (Santa cruz, catalog #sc-6254, and 1:1000 dilution), JNK (Santa cruz, catalog #sc-571, and 1:1000 dilution), p-ERK (Santa cruz, catalog #sc-7383, and 1:1000 dilution), and ERK (Santa cruz, catalog #sc-514302, and 1:1000 dilution), α7 nAChR (Alomone, catalog #ANC-007, and 1:1000 dilution) and β-actin (Sigma-Aldrich, catalog #A1978, and 1:2000 dilution). A Bio-Rad ChemicDoc imaging system (Bio-Rad) and Image J were used for image capturing and analysis, respectively.

3'-Diaminobenzidine (DAB) Staining:

Mice were anesthetized using avertin (tribromoethanol) and transcardially perfused with first phosphate-buffered saline (PBS) and then 4% paraformaldehyde (PFA). Then, the brains were dissected out, fixed in 4% PFA at 4° C. overnight, dehydrated in 30% sucrose, embedded in OCT, sagittally sectioned (20 μm) using a cryostat, and preserved in a cryoprotectant containing 30% ethylene glycol, 30% glycerol, and 40% PBS. For staining, floating sections were permeabilized in 0.1% triton X-100 in PBS (PBST), blocked by 1% BSA in PBST, probed by Iba-1 antibody (Wako, catalog #019-19741, and 1:800 dilution), inactivated endogenous peroxidases in 1% hydrogen peroxide, probed again by a goat anti-rabbit secondary antibody (Southern Biotech, catalog #4030-05, and 1:200 dilution), and developed using a DAB kit (Abcam, catalog #ab103723). All images were taken using a Nikon Eclipse E800 microscope with a 20× objective and analyzed by the Cellprofiler program. Every section was averaged from three brain regions prefrontal, occipital and parietal cortex, and the average of the three sections was used to represent individual animals.

Preparation of Primary Mouse Cortical Neurons, Microglia, Astrocytes, Neuron-Astrocyte Co-Cultures:

All primary cells were prepared from one-day old $\alpha 7^{-/-}$ pups and their isogenic Wt pups. Primary cortical neurons: One-day old pups were genotyped, the brains with desired genotypes were harvested, removed of meninges, and dissected out cortex. The cortex was minced in a cold HBSS buffer (Sigma-Aldrich, catalog #55021C). HBSS buffer was replaced sequentially by 0.25% trypsin (Sigma-Aldrich, catalog #T4049) and 2 µg/ml deoxyribonuclease I (Sigma-Aldrich, catalog #D5025) (at 37° C. for 20 min) and fetal bovine serum (2 min), and 2% B27 (Thermofisher, catalog #17504044) neurobasal medium (Thermofisher, catalog #21103049) and 1% GlutaMAX (Thermofisher, catalog #35050061). Brief centrifugation (300 g, 1-5 minutes) was used to recover the tissues and cells. The tissues were then triturated using a 10 ml pipette, the disassociated cells were washed, seeded into a 24-well plate (0.25 M/well) which was either coated with or contained coverslips coated with 0.1% ploy-D-lysine (Sigma-Aldrich, catalog #P6407) in borate buffer (pH 8.5), cultured at a 37° C., 5% $CO_2$ incubator for 2 days, and treated with 2.5 µM cytosine β-D-arabinofuranoside (Ara-C, Sigma-Aldrich, catalog #C1768) to remove astrocytes. Medium change by 50% was performed every two days, the neurons were ready for use on day 12 with purity above 90%, estimated by MAP2 staining (Santa cruz, catalog #sc-32791, and 1:500 dilution). Primary cortical neuron-astrocytes cocultures: A similar protocol was used to generate primary cortical neuron-astrocyte co-cultures except for omission of the Ara-C treatment from the protocol. The ratio of neurons to astrocytes in the co-cultures was estimated to be 1.5-2:1, estimated by MAP2 and GFAP staining (1:500 dilution with the same antibodies for Western blotting). Primary cortical microglia and astrocytes: A similar protocol was used to generate primary microglia and astrocytes except for use of full DMEM (Corning, catalog #MT15013CM) in place of B27 neurobasal medium, which was used to allow glia to grow. All cells were seeded into a T-75 flask without coating. Once the cells reached confluence, which usually took 12-14 days for brain extraction of two pups, the flask was shaken around 200 rpm for two hours to dislodge microglia. The culture medium containing the microglia was transferred to a 12-well plate, incubated in a 37° C., 5% $CO_2$ incubator for 30 minutes to allow the microglia to attach to the bottom of the well, and replaced by 20% LADMAC conditioned medium (see below) and 80% full DMEM and cultured for 3-4 days with medium change every other day. The leftover astrocytes attached to the T-75 flasks were trypsinized, seeded into a 12-well plate, and cultured in full DMEM for 3-4 days. The purity of microglia and astrocytes was greater than 99% as determined by staining for Iba-1 (the same antibody as the DAB staining) and GFAP, respectively.

Preparation of Conditioned Media and Use in Primary Cell Cultures: LADMAC Conditioned Medium:

LADMAC (ATCC, catalog #CRL-2420™) were cultured in a T-75 flask with EMEM (ATCC, catalog #30-2003™), 10% FBS, and 1% penicillin and streptomycin for 5-7 days to reach confluence. Then, the culture medium was collected, removed cell debris by brief centrifugation (300 g, 5 min), and filtered (0.22 µm filter, SIMSII, catalog #S30PES022S), and saved as LADMAC conditioned medium. Tat-containing or control DMEM conditioned media: 293T (ATCC, catalog #CRL-3216™) were seeded into a 10 cm dish, cultured in DMEM containing 10% FBS, 1% penicillin and streptomycin for 24 hours, transfected with 20 µg pcDNA3-Tat.Myc by calcium phosphate precipitation, cultured for 24 hours, changed to fresh DMEM medium, and cultured for additional 48 hours. Then, the culture medium was collected, removed cell debris by centrifugation (300 g, 5 minutes), followed by filtering through a 0.22 µm filter, and saved as Tat-containing conditioned medium (Tat-CM). pcDNA3 was also transfected as a control to generate the control condition medium (Ctrl-CM). To treat primary microglia, 70% Tat-containing or control conditioned medium, 20% fresh DMEM, 10% LADMAC conditioned medium were used. To treat primary astrocytes, 70% Tat-containing or control conditioned medium and 30% fresh DMEM were used. Tat-containing or control neurobasal conditioned medium: Tat-containing and control neurobasal conditioned medium was similarly prepared except for use of an increased number of seeding cells, 48 hours culturing after transfection, change to neurobasal medium with 1% GlutaMAX, and 24 hours after the medium change, and saved as Tat-containing neurobasal conditioned medium (Tat-CM) or control neurobasal conditioned medium (Ctrl-CM). To treat primary neurons and primary cortical neuron-astrocyte co-cultures, 98% Tat-containing or control neurobasal conditioned medium and 2% B27 (50×) were used to replace 50% culture medium. To activate α7 nAChR in cell cultures, 1 µM PNU-120596 accompanied with 0.5 µM PNU-282987 (Sigma-Aldrich, catalog #P6499) (PAM+P2) was applied into conditioned medium. Both of them were dissolved in DMSO at high concentration (PNU-120596: 100 mM, PNU-282987: 50 mM) as stocks. A Nikon Eclipse TE2000-S microscope with a 10× objective was used to capture the images of microglia in the bright field, and the images were converted by the Ilastik program to visualize the cell morphology and quantitated by the Cell-profiler program. Three images were randomly captured from each well.

Immunofluorescence Staining:

Brain sections (20 µm) were permeabilized in PBST, blocked in 1% BSA in PBST, and probed using appropriate primary antibodies against PSD-95 (1:500 dilution with the same western blotting antibody) or MAP2 (same to above) and secondary antibodies goat anti-rabbit 555 (Thermofisher, catalog #A21428, and 1:500 dilution) or goat anti-mouse 488 (Thermofisher, catalog #A11001, and 1:500 dilution). For cultured cells, the cells were first fixed with 4% PFA for 10 minutes, and then proceeded using the same procedures as for brain sections. All images from brain sections were taken using Olympus FV10i confocal microscope with a 60× oil objective. The entire cortex and hippocampus region were checked, and frontal cortex and CA1 were chosen as the representative regions to verify PSD-95 expression. All culture cell images were taken using a Nikon Eclipse 800 microscope with a 100× oil objective. Three to six individual neurons were randomly selected and averaged for each coverslip. PSD-95-positive puncta within the trunk of neuron dendrites (first order) was analyzed for primary cortical neurons, while PSD-95-positive puncta of the secondary dendrites (second order) were analyzed for neuron-astrocyte co-cultures. Image J was used to determine the percentage of PSD-95 positive area to the total MAP2-positive area.

Data Analysis:

Three-way repeated measures ANOVA was used in MWZ training stages, and all other experiments used either two-way or three-way ANOVA, whenever applicable. Bonferroni test was used for all post hoc analyses. All statistical analyses were performed using IBM SPSS 20. $p<0.05$ was considered significant and marked as *, # or $ for comparisons among different groups; p<0.01 and p<0.001 were both considered highly significant and marked as  and *, respectively.

Immunofluorescence Staining for SYP:

Primary antibodies against SYP (Abcam, catalog #ab32127, and 1:500 dilution). All leftover procedures were same to PSD-95 staining.

HE Staining:

Mice were anesthetized and sacrificed without perfusion. Their brain was sectioned at 8 μm thickness in cryostat. Nuclei and cytoplasm were stained by hematoxylin and eosin, respectively. The fixation procedure was same to DAB staining.

Real-Time Reverse Transcription PCR (qPCR):

Total RNA was isolated from cells using TRIzol (Thermofisher, Catalog number: 15596026). cDNA was synthesized from 1 μg RNA using a Script II RT kit (Bio-Rad, Catalog number: 1708840) and used as a template for qPCR using a SYBR Green kit (Bio-Rad, Catalog number: 1725270). Bio-Rad CFX Manager Software was used to calculate gross-threshold (CT) values. The $2^{(-\Delta\Delta CT)}$ was calculated to represent the fold change of gene expression and normalized using β-actin as a reference. All the primers was as follows: TNF-α: forward: 5'-CAC CAC GC TCT TCT GTC TAC T-3' (SEQ ID NO:01), reverse: 5'-TTT GCT ACG ACG TGG GCT A-3' (SEQ ID NO:02); IL-16: forward: 5'-GAA ATG CCA CCT TTT GAC AGT GA-3' (SEQ ID NO:03), reverse: 5'-AGT GAT ACT GCC TGC CTG AAG-3' (SEQ ID NO:04); IL-4: forward: 5'-GAG ACT CTT TCG GGC TTT TC-3' (SEQ ID NO:05), reverse: 5'-TGA TGC TCT TTA GGC TTT CCA-3' (SEQ ID NO:06); IL-6: forward: 5'-ACA AGT CCG GAG AGG AGA CT-3' (SEQ ID NO:07), reverse: 5'-TTC TGC AAG TGC ATC ATC GT-3' (SEQ ID NO:08); IL-12: forward: 5'-TAC TAG AGA GAC TTC TTC CAC AAC AAG AG-3' (SEQ ID NO:09), reverse: 5'-TCT GGT ACA TCT TCA AGT CCT CAT AGA-3' (SEQ ID NO:10); IL-18: forward: 5'-GAC AAC ACG CTT TAC TTT ATA CCT GA-3' (SEQ ID NO:11), reverse: 5'-GTG AAG TCG GCC AAA GTT GT-3' (SEQ ID NO:12); Mcp-1: forward: 5'-CAC TCA CCT GCT GCT ACT CAT-3' (SEQ ID NO:13), reverse: 5'-ATT CCT TCT TGG GGT CAG CA-3' (SEQ ID NO:14); GM-CSF: forward: 5'-TGC TTT TGT GCC TGC GTA ATG-3' (SEQ ID NO:15), reverse: 5'-TCC AAG CTG AGT CAG CGT TTT C-3' (SEQ ID NO:16); IL-10: forward: 5'-CCA GAA ATC AAG GAG CAT TT-3' (SEQ ID NO:17), reverse: 5'-CAC ACT GCA GGT GTT TTA GC-3' (SEQ ID NO:18); IFN-γ: forward: 5'-GGA TGC ATT CAT GAG TAT TGC-3' (SEQ ID NO:19), reverse: 5'-CCT TTT CCG CTT CCT GAG G-3' (SEQ ID NO:20); IL-12b: forward: 5'-GAC CAT CAC TGT CAA AGA GTT TCT AGA T-3' (SEQ ID NO:21), reverse: 5'-AGG AAA GTC TTG TTT TTG AAA TTT TTT AA-3' (SEQ ID NO:22); β-actin: forward: 5'-AGA GAA GTG GGG TGG CTT TT-3' (SEQ ID NO:23), reverse: 5'-AAA CTG GAA CGG TGA AGG TG-3' (SEQ ID NO:24).

TABLE 3

Experimental groups for PAM treatment, α7 nAChR knockout with PAM treatment and p38 MAPK inhibitor.

| Mice | Sex | PAM treatment* | α7 genotype** | p38 MAPK inhibitor (SB239063) |
|---|---|---|---|---|
| Wt | Male | Wt + DMSO | α7+/+ Wt | Wt + VEHICLE*** |
| | | Wt + PAM | α7-/- Wt | Wt + SB239063 |
| | Female | Wt + DMSO | α7+/+ Wt | Wt + VEHICLE |
| | | Wt + PAM | α7-/- Wt | Wt + SB239063 |

TABLE 3-continued

Experimental groups for PAM treatment, α7 nAChR knockout with PAM treatment and p38 MAPK inhibitor.

| Mice | Sex | PAM treatment* | α7 genotype** | p38 MAPK inhibitor (SB239063) |
|---|---|---|---|---|
| iTat | Male | iTat + DMSO | α7+/+ iTat | iTat + VEHICLE |
| | | iTat + PAM | α7-/- iTat | iTat + SB239063 |
| | Female | iTat + DMSO | α7+/+ iTat | iTat + VEHICLE |
| | | iTat + PAM | α7-/- iTat | iTat + SB239063 |

*PNU-120596 was dissolved in 100% DMSO and DMSO was used as the control.
**α7+/+: Wt α7 nAChR knockout; α7-/-: α7 nAChR knockout. All animals in this experiment were treated with PAM.
***VEHICLE: p38 MAPK inhibitor SB239063 was dissolved in 100% DMSO, then diluted in PEF400 and saline in a ratio of 0.8:32:67. Thus, VEHICLE was a mix of DMSO, PED400 and saline of 0.8:32:67.

Results

Example 1. PAM Administration Alleviated HIV Tat-Induced Behavioral Deficits and Neuropathologies To determine if α7 nAChR is involved in HAND, iTat mice were fed with Dox-containing food pellets for 7 days, injected s.c. with a well-studied and highly specific positive allosteric modulator (PAM) PNU-120596 of α7 nAChR[73,74] for 5 days, and then subjected to open field test (OPT) for locomotor activity on day 14, and Morris Water Maze test (MWZ) for learning and spatial memory on day 15-20, and euthanized to harvest tissues on day 21 (FIG. 1A). Dox-containing food pellet feeding and PAM injection continued during the next 7 days of behavioral tests. To minimize the effects of injection on behavioral tests, PAM was injected 5 hours after each behavioral test. Wild-type mice and solvent DMSO were included as controls for iTat mice and PAM in the experiments, respectively, mice were further grouped by sex, which gave rise to a total of 8 experimental groups for analyses (FIG. 1B).

For OPT, the total travel distance and the maximum speed were measured. In DMSO treatments, iTat mice showed shorter travel distance than Wt mice for both male and female mice, and the difference between the female iTat mice and female Wt was much more than the difference between male iTat mice and female Wt mice (left panel, FIG. 10). In comparison, PAM treatment led to improvement of the travel distance of iTat mice, some improvement of the travel distance of Wt mice. For maximum speed, there was no difference between iTat mice and Wt mice in the DMSO treatment group, and PAM treatments led to increases of the maximum speed of male Wt mice but not other mice (right panel, FIG. 10).

Figure 1D:
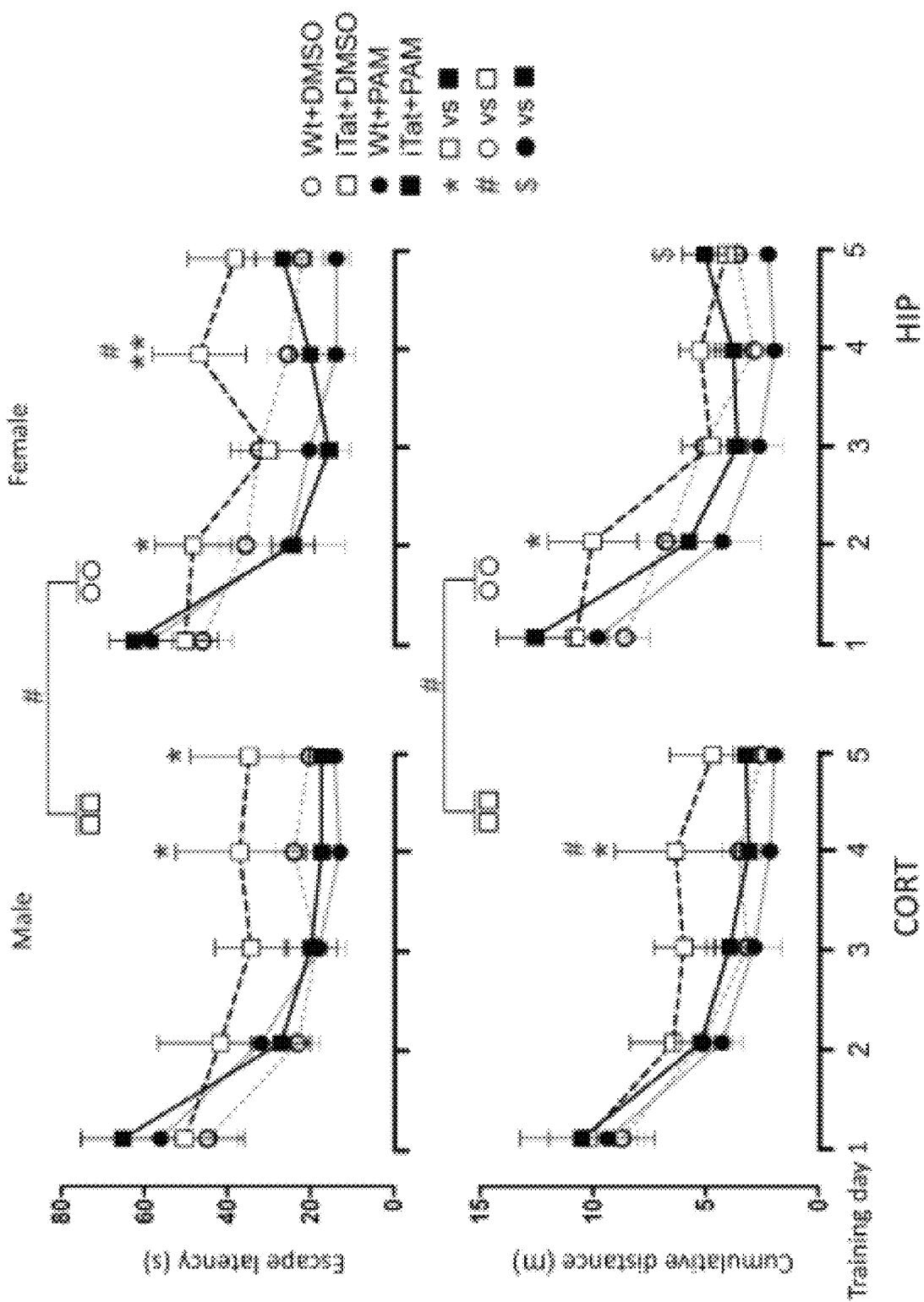

At the MWZ training stage, escape latency time (Escape latency) and cumulative travel distance (Cumulative distance) were measured. Compared to Wt mice treated with DMSO, iTat mice treated with DMSO showed longer escape latency time (upper left panel, FIG. 1D) and longer cumulative travel distance (lower panel, FIG. 1D) on all five days, with differences of cumulative travel distances in male mice and escape latency time for female mice on day 4. PAM treatment led to remarkable improvements in iTat mice, with differences of escape latency time in male iTat mice on day 4 and 5 and female iTat mice on day 2 and 4 (upper panels, FIG. 1D), and differences of cumulative travel times in male iTat mice on day 4 and female iTat mice on day 2 (lower panels, FIG. 1D). However, only some improvements on male Wt mice were found by PAM treatment. In addition, there was an increase in cumulative travel distance in PAM-treated female iTat mice on day 5 when compared with PAM-treated female Wt mice.

Figure 7:
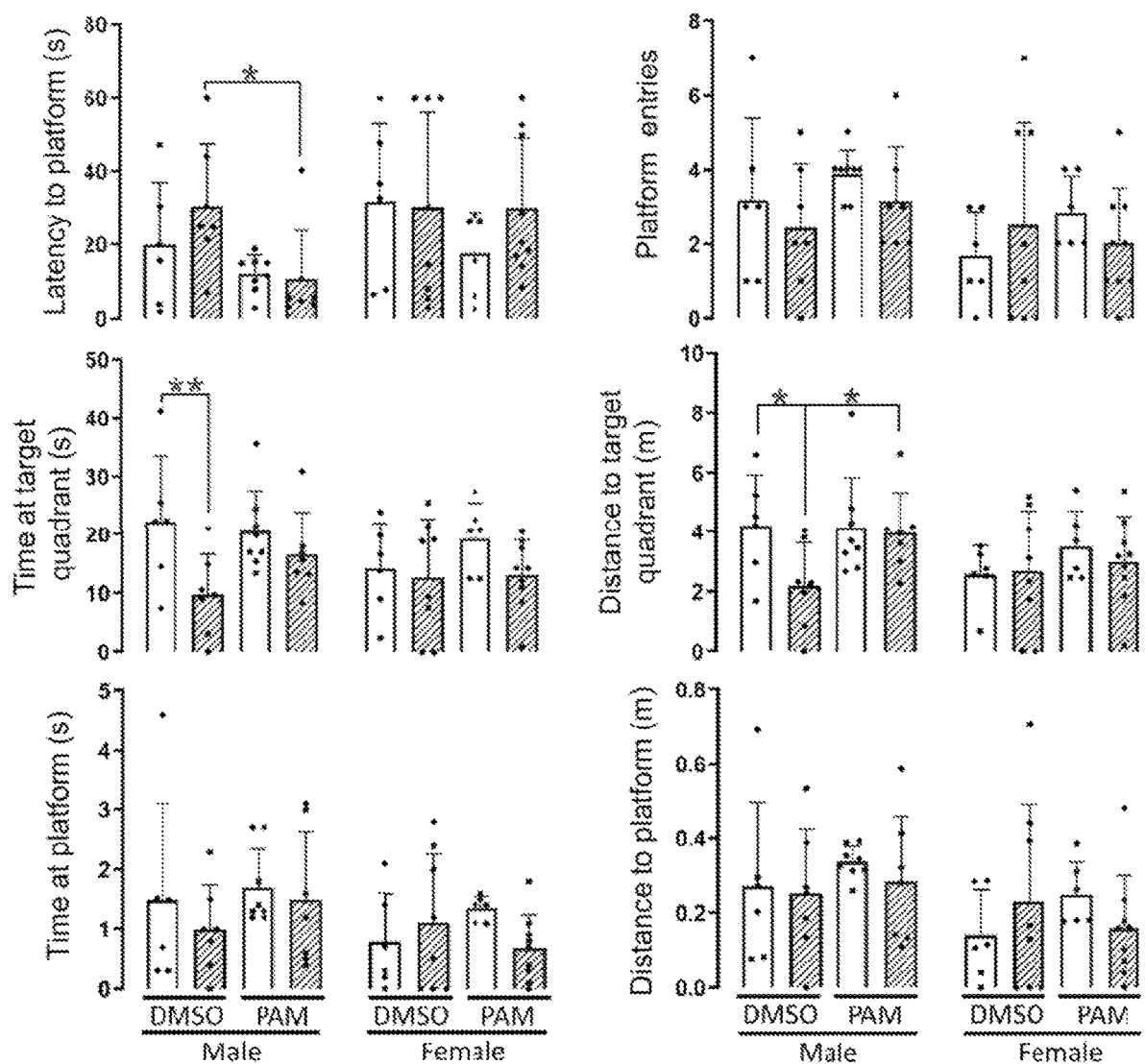
FIG. 7 shows results from the Morris Water Maze probe test of the mice in FIG. 1.

For the MWZ probe test, latency to platform, platform entries, time at target quadrant, distance to target quadrant, time at platform, and distance to platform were measured. Male iTat mice treated with DMSO showed less time at target quadrant and shorter distance to target quadrant, which were reversed by PAM treatment with the differences in distance to target quadrant (middle panels, FIG. 7). Interesting to note is the longer latency to platform in male iTat mice treated with DMSO than male Wt mice-treated with DMSO, and decreases of latency to platform in both male iTat and Wt mice by PAM treatment (left panel, FIG. 7). For other indices including platform entries, time at platform, and distance to platform, there were no differences between iTat and Wt mice, DMSO- and PAM-treated mice, and male and female mice.

Next, the changes of neuron presynaptic synaptic marker synaptophysin (SYP) and postsynaptic marker PSD-95, astrocyte marker GFAP and microglia marker Iba-1 in cortex (CORT) and hippocampus (HIP) were determined. In CORT, iTat mice treated with DMSO showed significantly higher GFAP and Iba-1 than Wt mice treated with DMSO (right panels, FIG. 1E; upper and left panels, FIG. 1F). PAM treatment led to significant increases of PSD-95 in Wt mice and even more in iTat mice but had decreased GFAP in iTat mice and decreased Iba-1 in both Wt and iTat mice. Meanwhile, SYP showed no changes between iTat mice and Wt mice, and between DMSO and PAM treatment (right panels, FIG. 1E; upper and left panels, FIG. 1F). In HIP, PAM treatment increased PSD-95 in both Wt and iTat mice, and iTat mice treated with DMSO showed more Iba-1 than Wt mice treated with DMSO (left panels, FIG. 1E; lower and left panels, FIG. 1F). There were no differences of SYP and GFAP between Wt mice and iTat mice, and between DMSO- and PAM-treated mice. PSD-95 expression and its location in all these tissues were further confirmed by double immunofluorescent staining for PSD-95 and MAP2 (FIG. 1G).

Figure 1E:
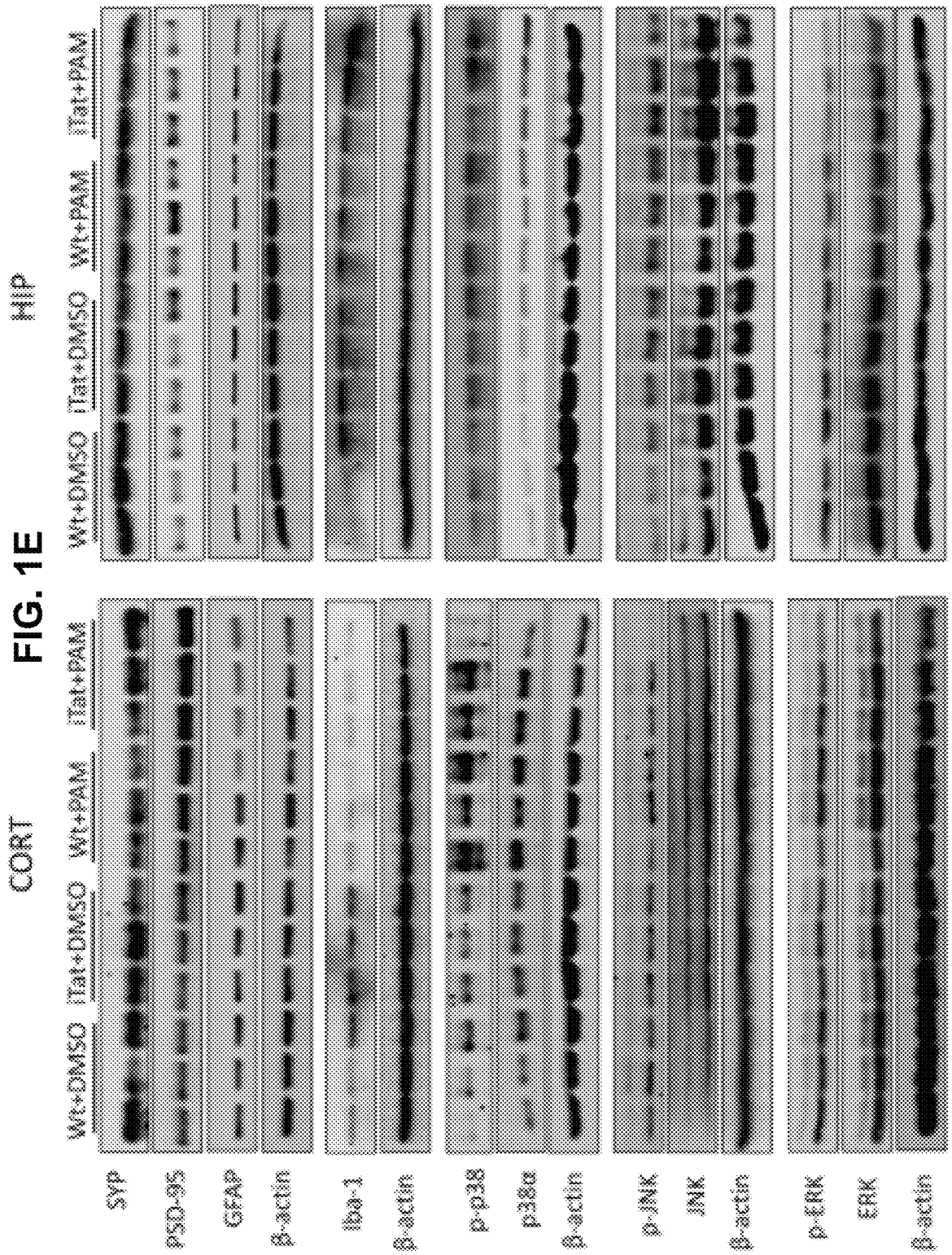
Figure 1F:
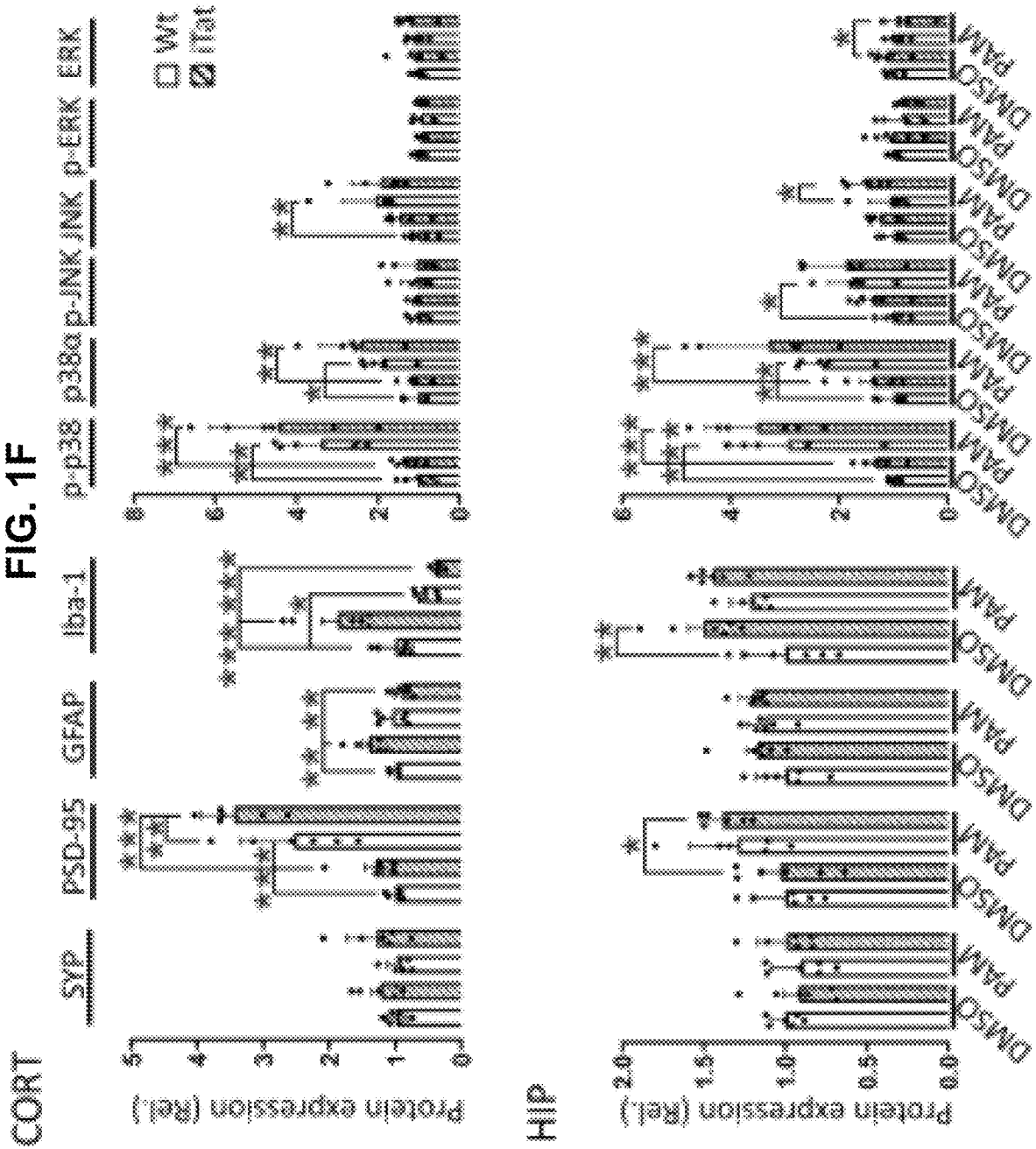

It was next determined which MAPK signaling pathways were responsive to PAM neuroprotective effects against Tat-induced neuropathologies. Both CORT and HIP were analyzed for expression and phosphorylation of p38, JNK, and ERK. PAM treatment led to increases of both p38 and p-p38α in both CORT and HIP, increases of JNK in CORT of Wt mice, increases of JNK in CORT of iTat mice, increases of JNK and p-JNK in HIP of all mice, and decreases of ERK in HIP of iTat mice (FIG. 1E; right panels, FIG. 1F). PAM treatment also led to increases of JNK and p-JNK in both CORT and HIP of Wt mice. There was a difference of JNK between PAM-treated iTat mice and PAM-treated Wt mice. But there were no differences of p-JNK in CORT of all mice and no differences of p-ERK in CORT and HIP of both iTat and Wt mice. Interestingly, iTat mice showed no changes of p38, JNK, ERK, and their phosphorylated counterparts compared to Wt mice, both in the absence and presence of PAM treatment. Furthermore, no differences were noted between female and male mice in all the molecular analyses, thus the data were pooled after normalization using Wt mice treated with DMSO as the reference.

Taken together, this shows that PAM treatment significantly increased locomotor activity, enhanced learning and memory processes, elevated PSD-95 expression, and inhibited GFAP and Iba-1 expression in iTat mice. It also demonstrates that these changes were associated with increased levels of p38 and its phosphorylation, to a lesser extent JNK and its phosphorylation, but not ERK and its phosphorylation. All these changes were more pronounced in CORT of iTat mice than HIP of iTat mice. These findings demonstrated that PAM was neuroprotective against HIV Tat-induced behavioral impairments and neuropathologies and suggest that PAM-mediated activation of α7 nAChR is likely involved.

Example 2. α7 nAChR Knockout Abrogated PAM-Induced Neuroprotective Function Against Tat-Induced Behavioral Impairments and Neuropathologies To ascertain the neuroprotective function of PAM and the roles of α7 nAChR in PAM neuroprotective function against Tat-induced behavioral impairments and neuropathologies, α7 nAChR knockout mice ($α7^{-/-}$) were cross bred with iTat mice, and generated $α7^{-/-}$iTat mice, and used these mice in the subsequent three-way ANOVA design studies (α7 nAChR, iTat, and sex, FIG. 2A), in which all eight groups of mice were fed with Dox-containing food pellets and s.c. injected with PAM in the same way as stated in FIG. 1A and subject to the same behavioral tests and analysis of SYP, PSD-95, GFAP, IBa-1 and MAPK signaling pathways.

Figure 2B:
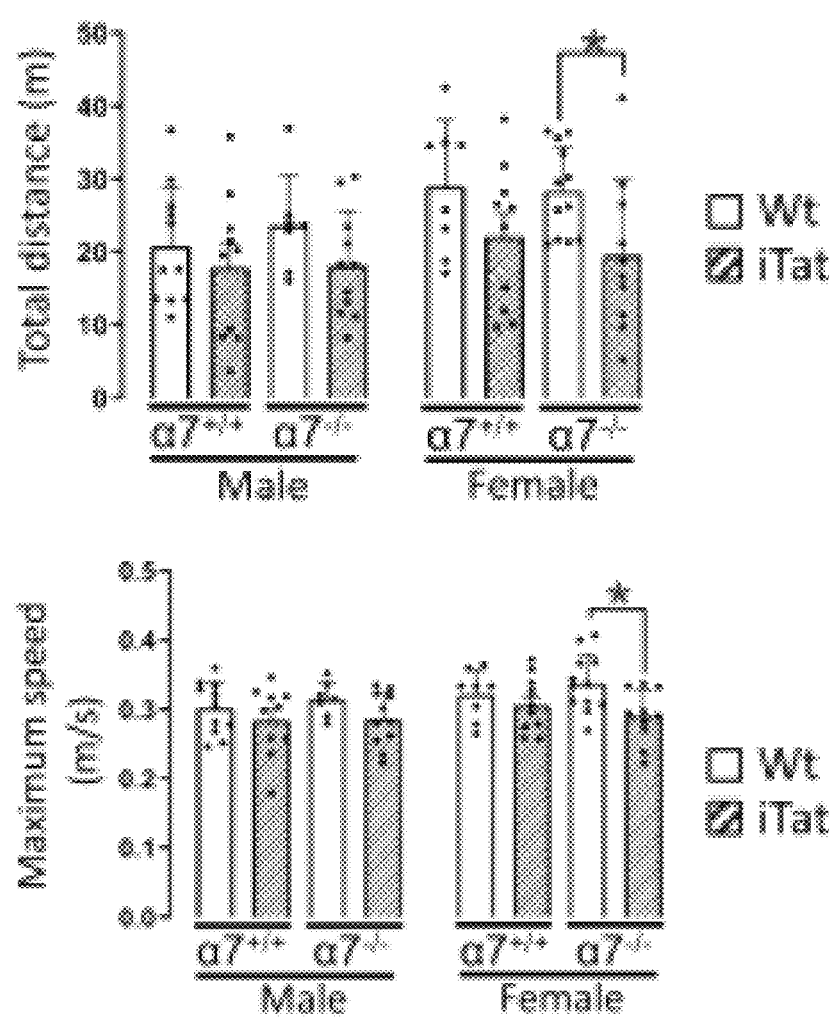
Figure 2C:
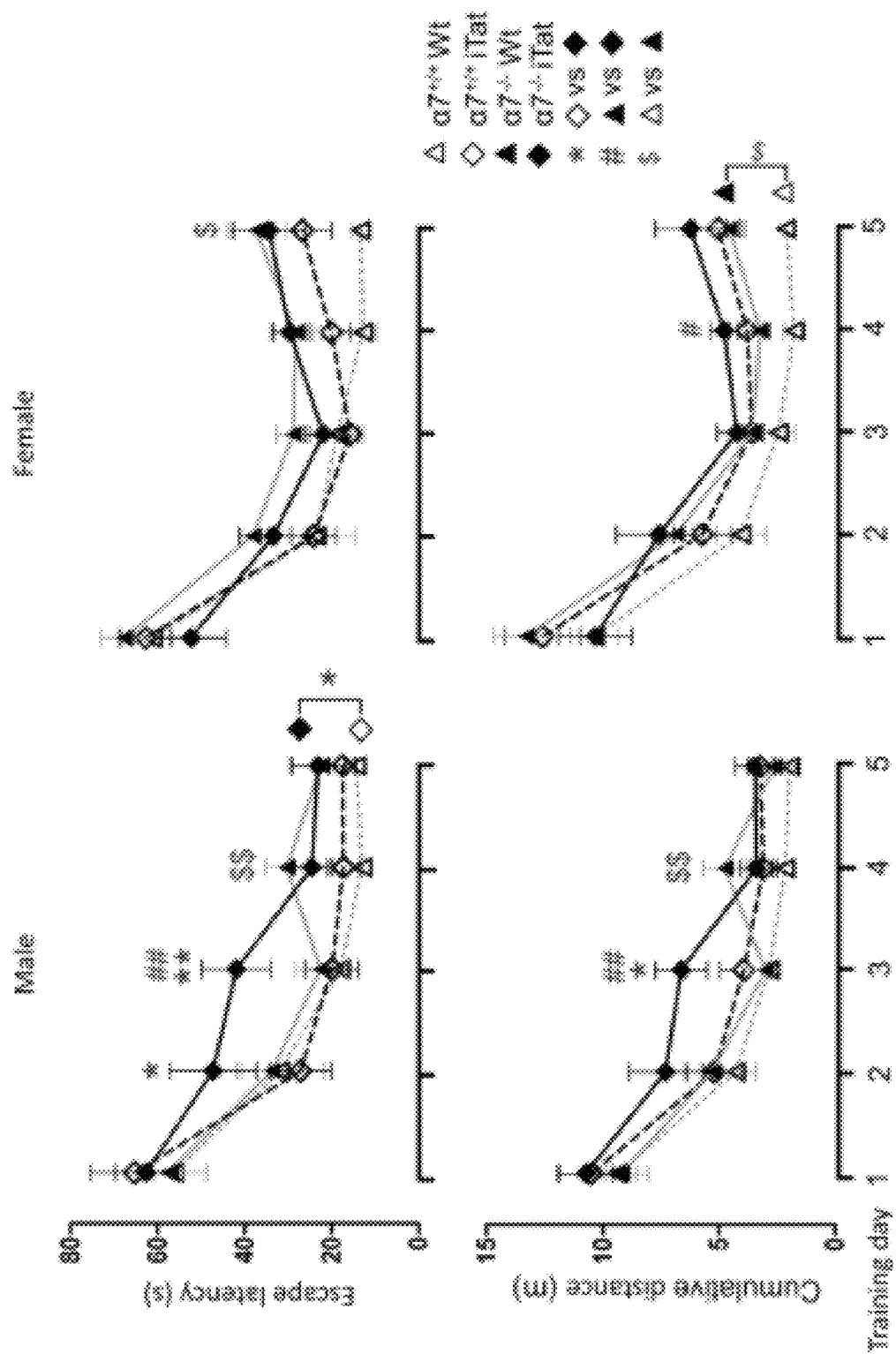
Figure 8:
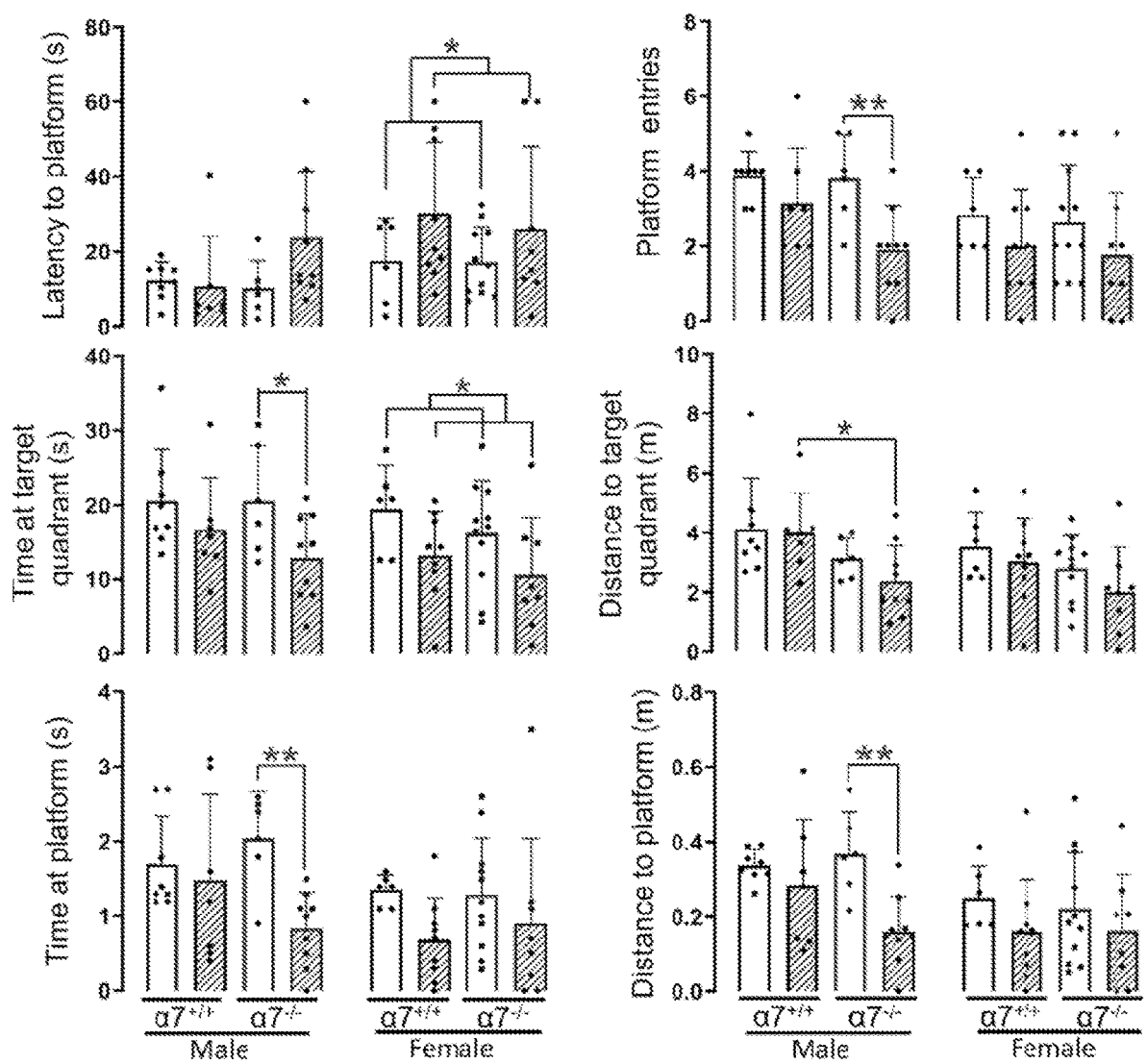
FIG. 8 shows results from Morris Water Maze probe test of the mice in FIG. 2.
Figure 9:
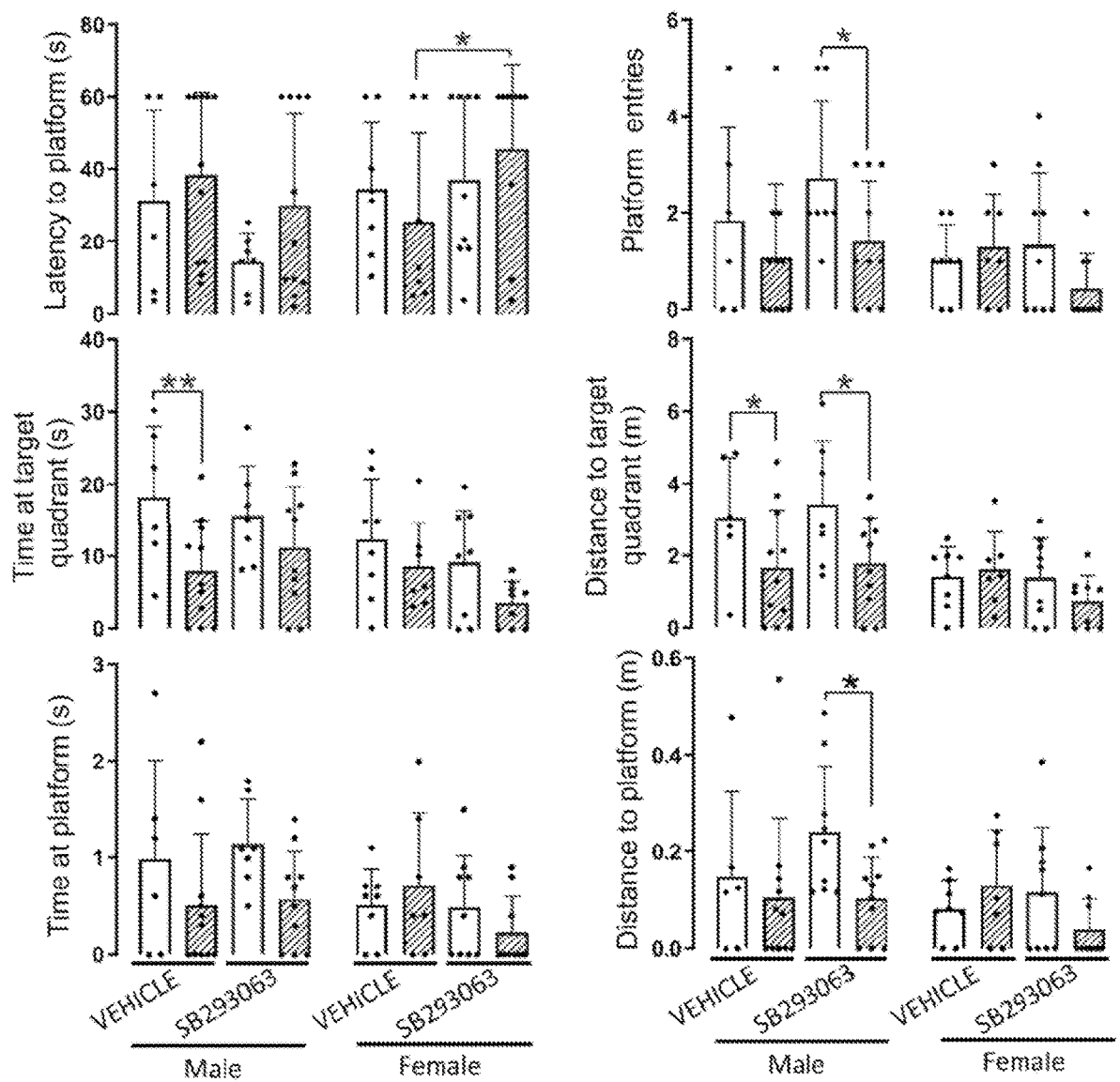
FIG. 9 shows results from Morris Water Maze probe test of the mice in FIG. 3.

In OPT, there were only differences of total travel distance and maximum speed between $α7^{-/-}$Wt female mice and $α7^{-/-}$iTat female mice (FIG. 2B). During the MWZ training stage, $α7^{-/-}$iTat male mice showed longer escape latency than $α7^{+/+}$iTat male mice on all five days with differences on day 2 and 3 (upper left panel, FIG. 2C). $α7^{-/-}$iTat male mice also had longer cumulative travel distance than $α7^{+/+}$iTat male mice on day 3 (lower left panel, FIG. 2C). All female mice showed no differences of escape latency and cumulative distance (right panels, FIG. 2C). In addition, compared with $α7^{-/-}$WT mice, $α7^{-/-}$iTat mice showed longer escape latency and longer cumulative distance on day 3 (male mice) and on day 4 (female mice), suggesting that Tat expression caused more severe learning impairment in $α7^{-/-}$ mice. Furthermore, $α7^{-/-}$Wt had longer escape latency and longer cumulative distance than $α7^{+/+}$Wt on day 4 (male mice), and only longer escape latency on day 5 (female mice) and longer cumulative distance on all five days (female mice), indicating that α7 nAChR knockout itself also had negative effects on the learning of the mice, particularly on female mice. In the probe test, $α7^{-/-}$iTat male mice had fewer platform entries, shorter time at target quadrant, time at platform, and distance to platform than $α7^{-/-}$Wt male mice (FIG. 8). $α7^{-/-}$iTat male mice also showed shorter distance to target quadrant than $α7^{+/+}$iTat male mice. In female mice, iTat mice showed longer latency to platform and shorter time at target quadrant than Wt mice. No other differences were noted among different groups of mice.

Figure 2D:
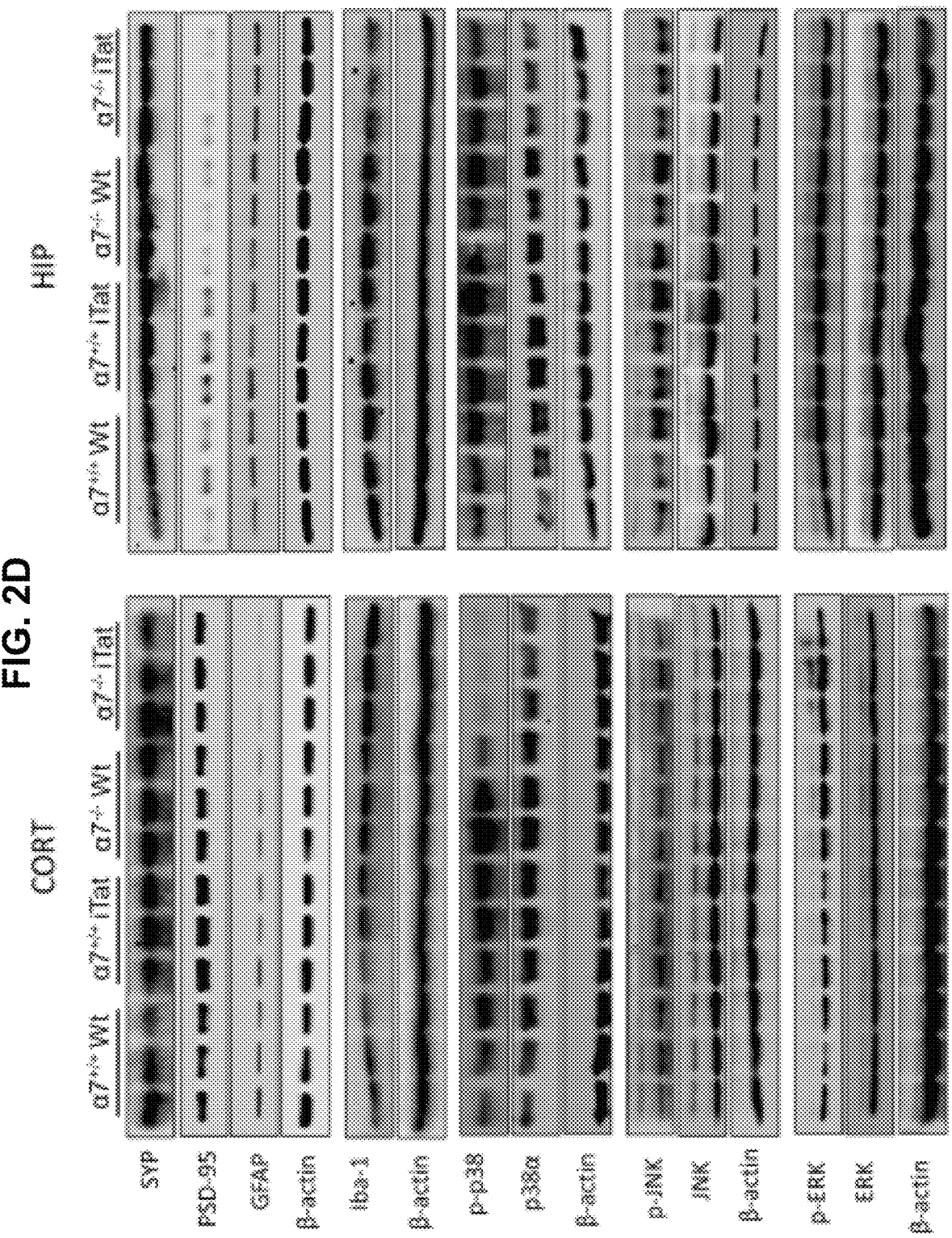
Figure 2E:
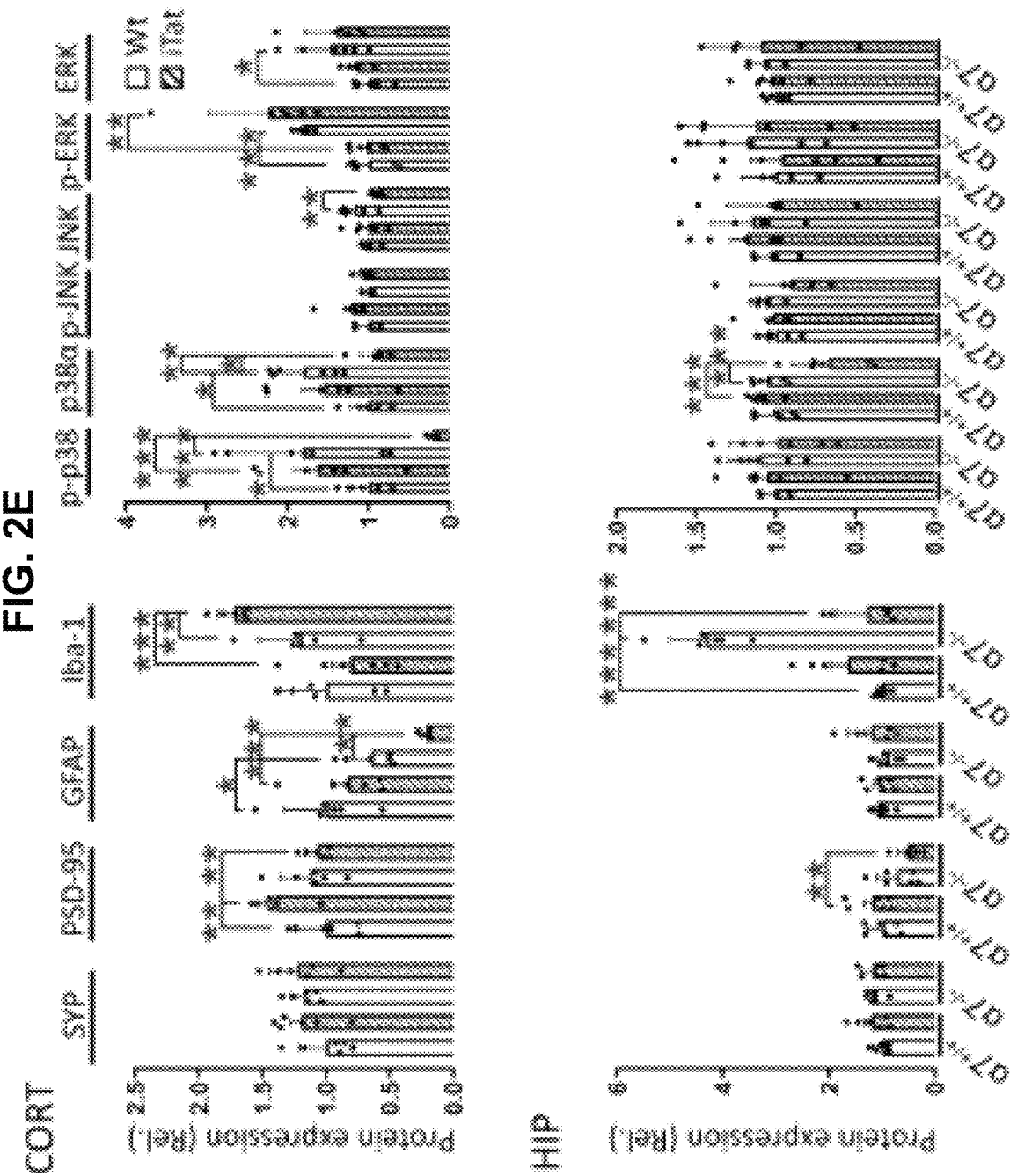
Figure 2F:
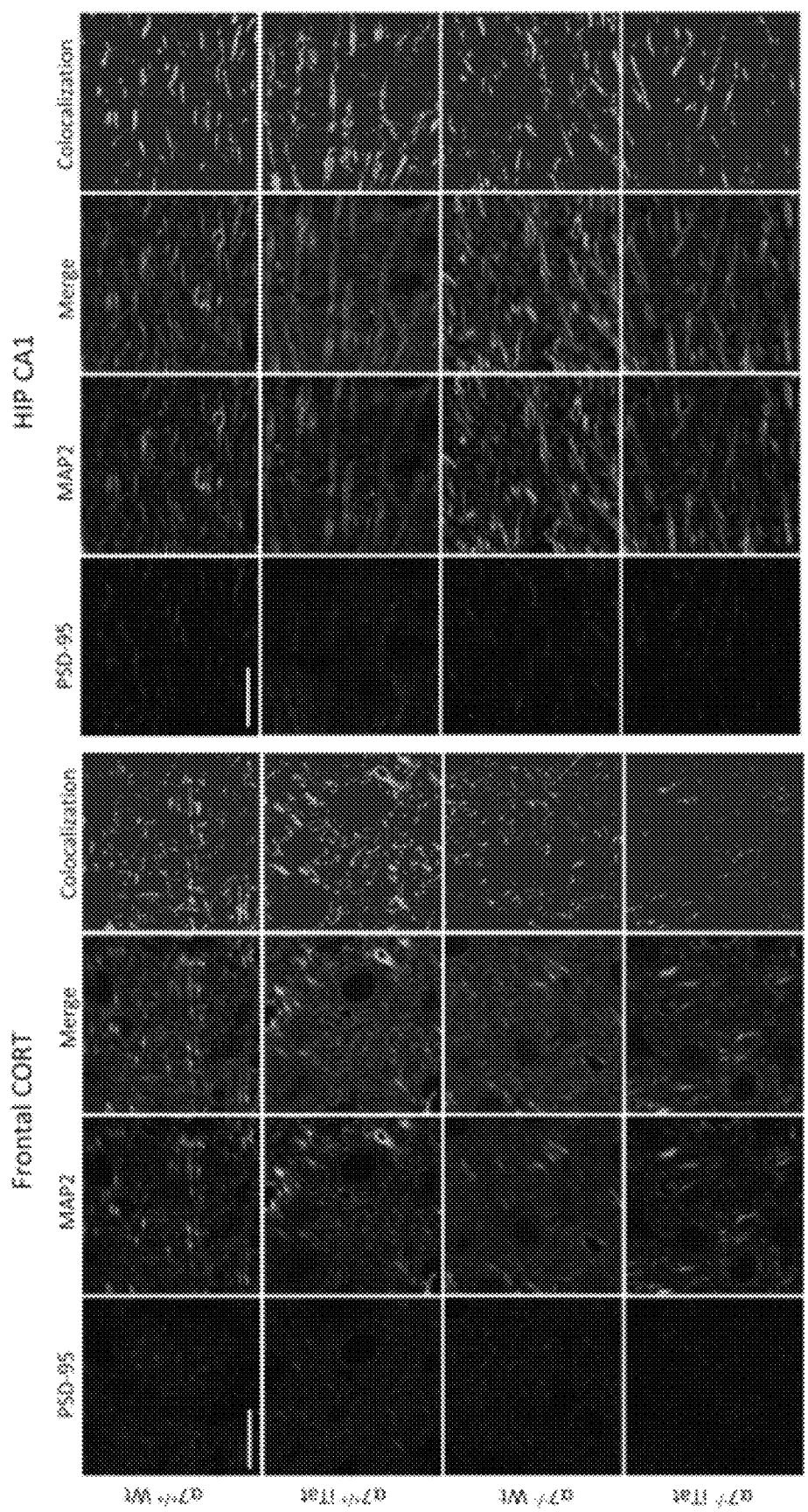

Protein expression in CORT and HIP of these mice were also determined. In CORT, $α7^{+/+}$iTat mice had higher PSD-95 than $α7^{+/+}$Wt mice, while no differences of PSD-95 were detected between $α7^{-/-}$iTat mice and $α7^{-/-}$Wt mice (left panels, FIG. 2D; upper left panels, FIG. 2E). $α7^{-/-}$Wt mice had lower GFAP than $α7^{+/+}$Wt mice, and $α7^{-/-}$iTat mice had lower GFAP than $α7^{+/+}$iTat mice and $α7^{-/-}$Wt mice. $α7^{-/-}$iTat mice had higher Iba-1 than $α7^{-/-}$Wt mice and $α7^{+/+}$iTat mice. In HIP, $α7^{-/-}$iTat mice showed lower PSD-95 than $α7^{+/+}$iTat mice (right panels, FIG. 2D; lower left panels, FIG. 2E). $α7^{-/-}$Wt mice had higher Iba-1 than $α7^{+/+}$Wt mice and $α7^{-/-}$iTat mice. PSD-95 expression and its location were further confirmed by double immunofluorescent staining for PSD-95 and MAP2 (FIG. 2F). With regard to MAPK signaling pathways, in CORT, $α7^{-/-}$iTat mice showed lower p38 and p-p38α than $α7^{-/-}$Wt and $α7^{+/+}$iTat mice, while α7⁻/⁻Wt mice showed higher p38 and p-p38α than α7⁺/⁺Wt mice (left panels, FIG. 2D; upper and right panels, FIG. 2E), further suggesting possible interplays among α7 nAChR, HIV Tat neurotoxicity and p38 MAPK signaling pathway. In HIP, p38 and p-p38α showed similar trends but are lower only for p-p38α in α7⁻/⁻iTat mice (right panels, FIG. 2D; lower and right panels, FIG. 2E). Only α7⁻/⁻iTat showed lower JNK than α7⁻/⁻Wt in CORT. α7⁻/⁻Wt had higher ERK and p-ERK than α7⁺/⁺Wt in CORT, while α7⁻/⁻iTat had higher p-ERK than α7⁺/⁺iTat in CORT. No other differences were noted with JNK, p-JNK, ERK, and p-ERK in HIP Taken together, these results show that α7 nAChR knockout abolished the neuroprotective effects of PAM against locomotor and learning and memory deficits of iTat mice. This also demonstrates that α7 nAChR knockout specifically led to significant decreases of PSD-95 and p38α in both CORT and HIP, p-p38α in CORT and significant increases of Iba-1 in CORT of iTat mice. These findings confirm that α7 nAChR was directly involved in PAM neuroprotective function against Tat-induced behavioral impairments and neuropathologies.

Example 3. p38 Inhibition Aggravated Tat-Induced Behavioral Impairments and Neuropathologies The inverse correlation between Tat-induced behavioral impairments and neuropathologies and p38 expression and phosphorylation by PAM treatment (FIG. 1) and α7 nAChR knockout (FIG. 2) raised the possibility that p38 MAPK signaling pathway would be an important mediator of Tat neurotoxicity and PAM neuroprotective function against Tat neurotoxicity. To address this possibility, we took advantage of SB239063, a potent and selective p38 MAPK inhibitor, was used and its effects on Tat-induced behavioral impairments and neuropathologies were determined using the same experimental scheme as FIG. 1A except for i.p. injection of SB239063 in place of s.c. injection of PAM in these eight groups of mice (FIG. 3A).

Figure 3B:
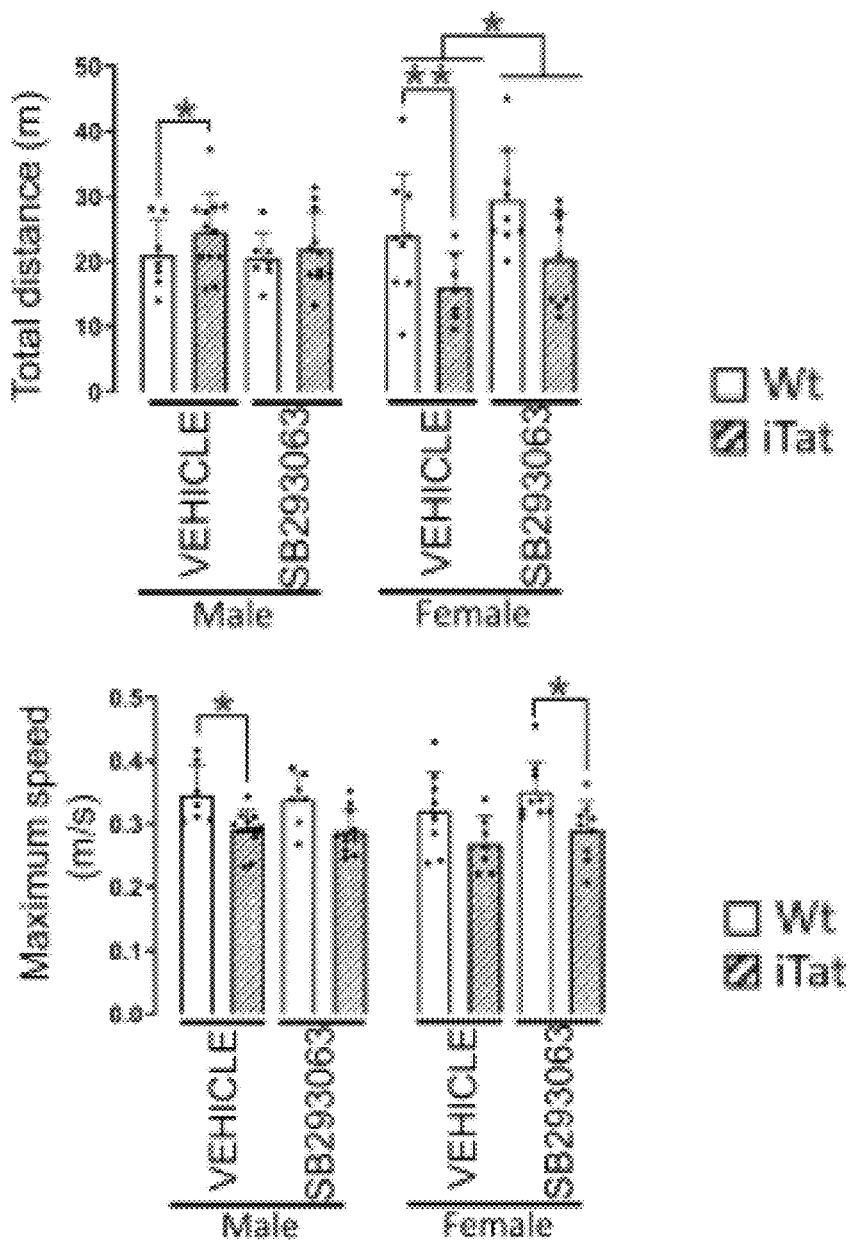

In OPT, iTat mice showed longer total travel distance than male Wt mice and shorter travel distance than female Wt mice and slower maximum speed than male and female Wt mice (FIG. 3B). SB239063 treatment led to no significant differences in travel distance and maximum speed between Wt and iTat mice, both male and female mice. Of note was that there was a difference of travel distance between SB239063-treated and vehicle-treated female mice, both Wt and iTat mice. In the MWZ training stage, male iTat mice showed longer escape latency than male Wt mice on all 5 days, while SB239063 treatment led to even longer escape latency than Wt mice, with differences on day 3 and 4 for male mice (upper and left panels, FIG. 3C). Female iTat mice had similar trends with difference on day 4 compared with female Wt mice (upper and right panels, FIG. 3C). Similar patterns of the results were obtained about the cumulative distance, with difference between vehicle-treated male iTat and male Wt mice on day 3 and difference between SB239063-treated male iTat and male Wt mice on day 2 and 3 and female iTat and Wt mice on day 4 (lower panels, FIG. 3C). In the MWZ probe test, in the vehicle treatment, iTat male mice had shorter time at target quadrant and distance to target quadrant than Wt male mice, while in the SB239063 treatment, male iTat mice had fewer platform entries, shorter distance to target quadrant and distance to platform than Wt male mice (Supplementary FIG. 3). Except for latency to platform in which SB239063-treated female iTat mice had longer latency to platform than vehicle-treated female iTat mice, all SB239063-treated female iTat mice had fewer platform entries, shorter time at target quadrant, distance to target quadrant, time at platform, and distance to platform than vehicle-treated female Wt and iTat mice and SB239063-treated female Wt mice.

Figure 3D:
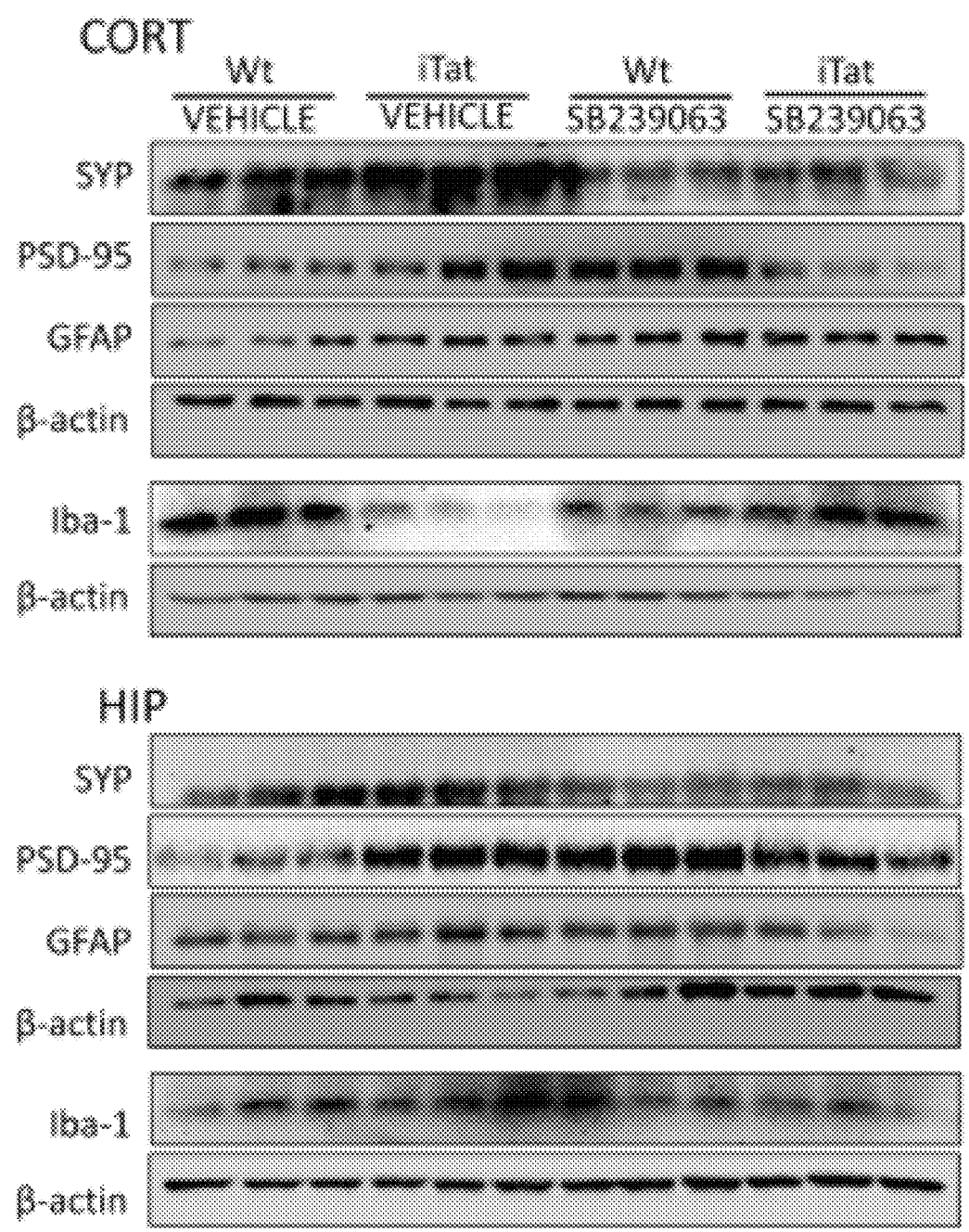
Figure 3E:
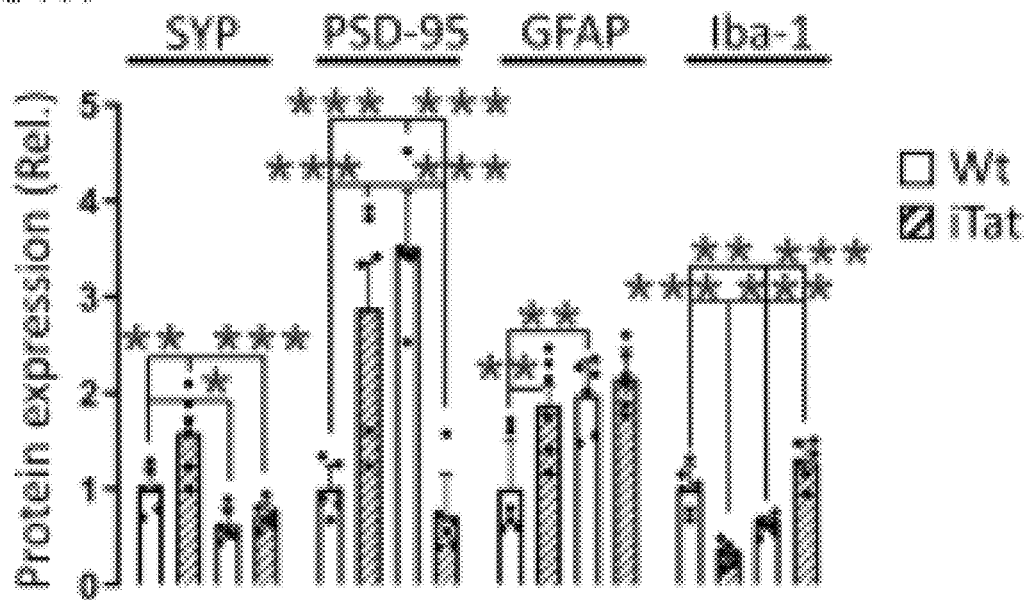
Figure 3E:
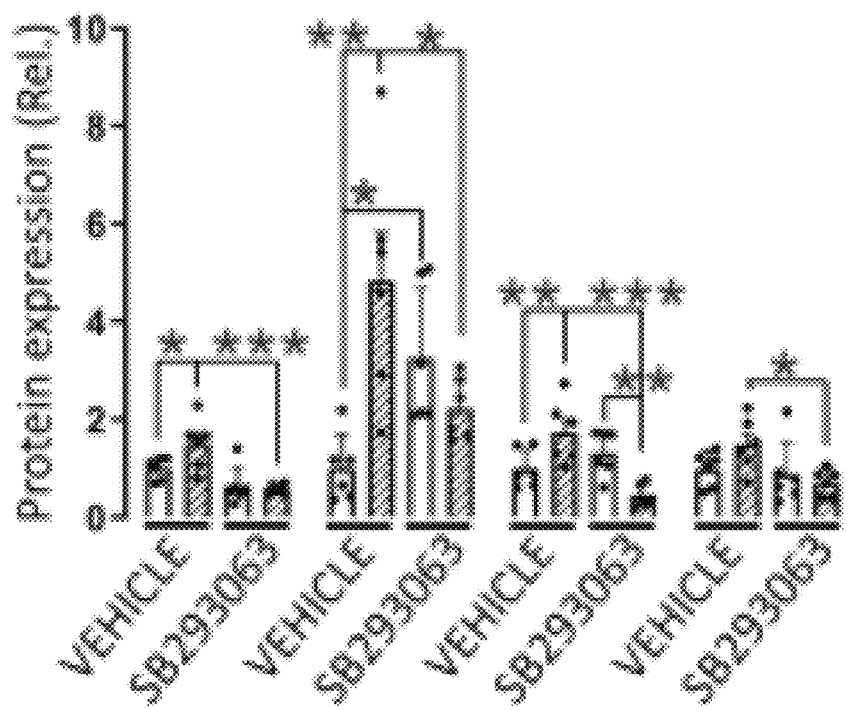
Figure 3F:
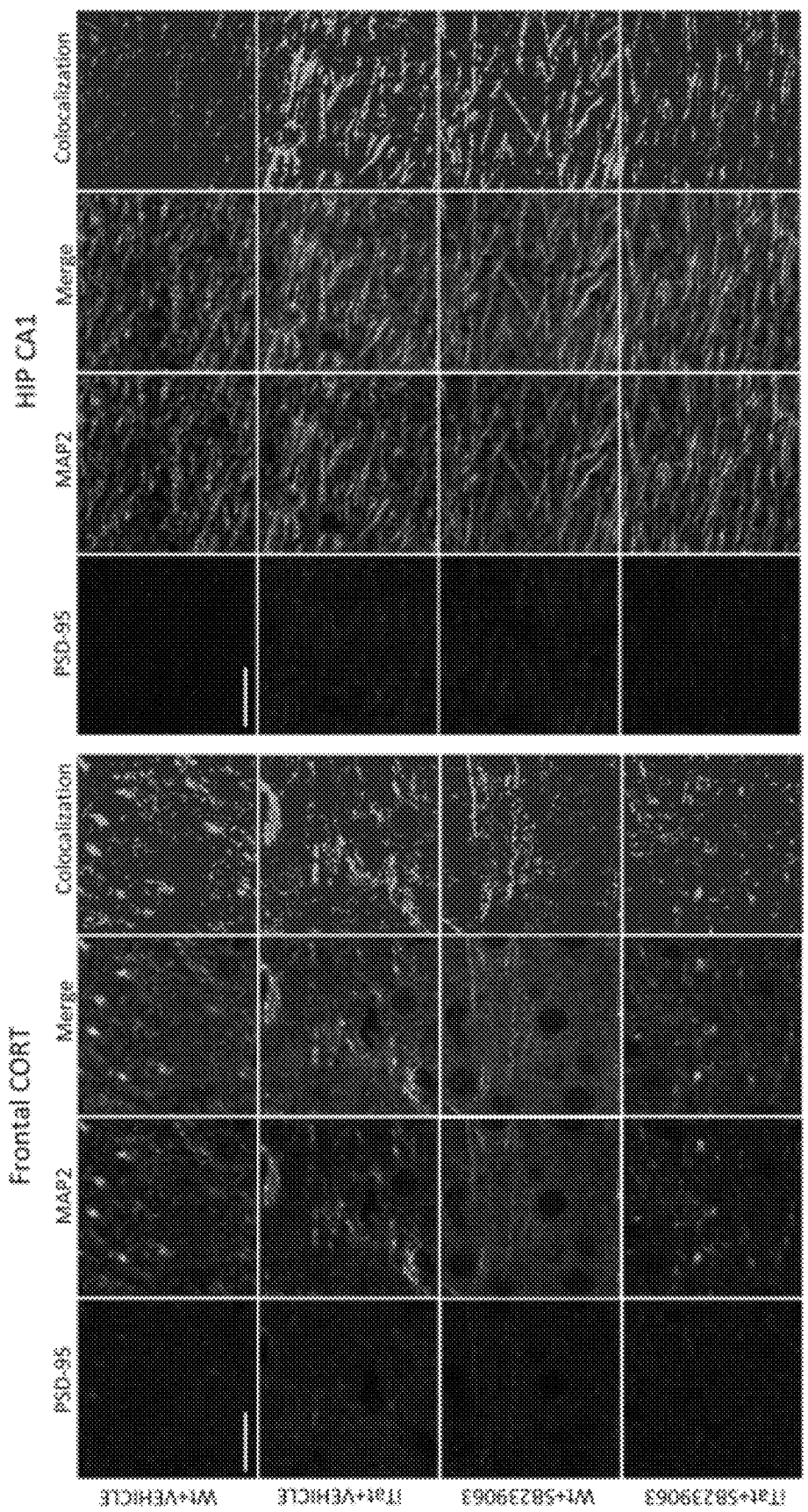
Figure 10A:
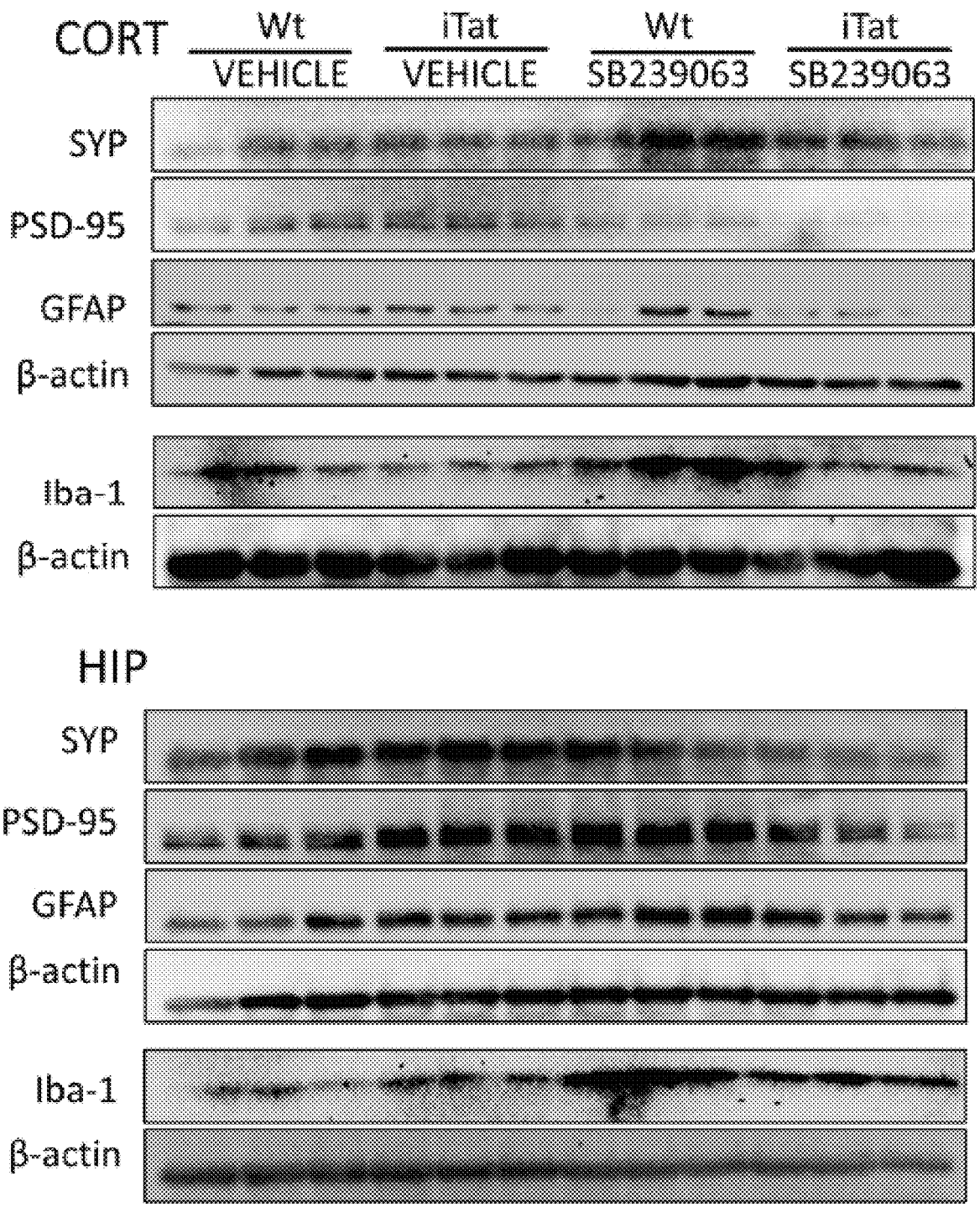
FIG. 10A-FIG. 10C show Western blotting and immunofluorescent staining of the brain tissues of female mice of FIG. 3 (n=6/group).
Figure 10B:
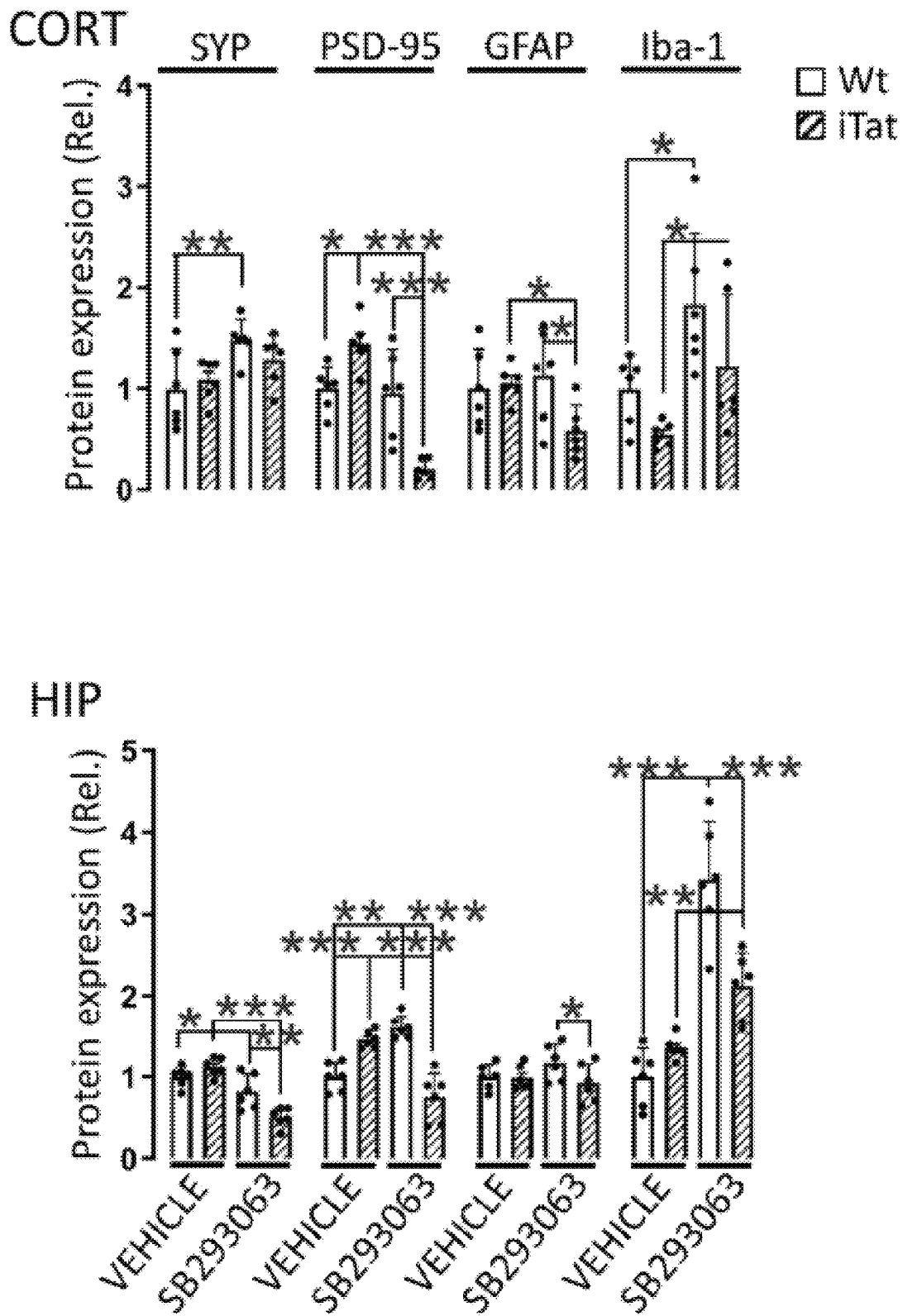
Figure 10C:
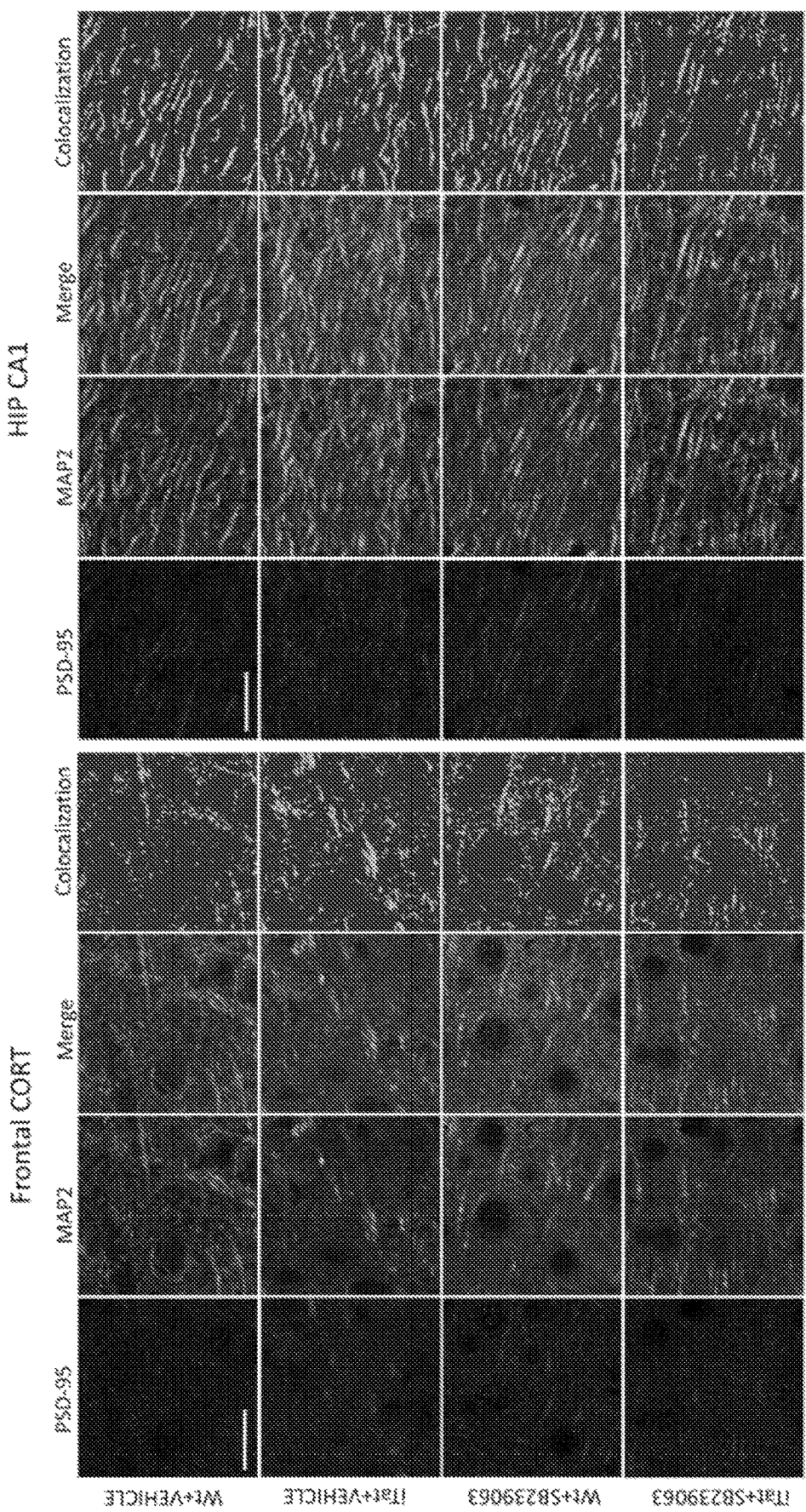

Similarly, CORT and HIP of both male and female mice were analyzed for protein expression, as they showed differential response to SB239063 treatment above (FIGS. 3D & E; FIGS. 10A & 10B). In CORT and HIP of both male and female mice, PSD-95 showed an identical pattern: vehicle-treated iTat mice had higher PSD-95 than vehicle-treated Wt mice, and SB239063-treated iTat mice had lower PSD-95 than SB239063-treated Wt mice (FIGS. 3D & E; FIGS. 10A & 10B). All changes in PSD-95 were further verified by immunofluorescent staining, also overlapped with MAP2 staining (FIG. 3F & FIG. 10O). In both CORT and HIP of male mice, vehicle-treated iTat mice had higher SYP and GFAP than vehicle-treated Wt mice, but SB239063-treated iTat mice showed no differences of SYN and GFAP (except HIP) from SB239063-treated Wt mice (FIGS. 3D & E). In both CORT and HIP of female mice, vehicle-treated iTat mice showed no differences of SYP, GFAP and Iba-1 from vehicle-treated Wt mice, but SB239063-treated iTat mice showed lower SYP, GFAP and Iba-1 with differences than SB239063-treated Wt mice (FIGS. 10A & 10B). There were other differences between individuals and groups, but with no consistent patterns.

Taken together, these results show that inhibition of p38 MAPK signaling pathway by SB239063 led to worsening learning and memory deficits in iTat mice and PSD-95 down-regulation and that SB239063 treatment showed no effects on the locomotor activity but showed sex-specific changes of protein expression of SYP and GFAP. These findings suggest strong interplays between p38 MAPK signaling pathway and PSD-95 in Tat neurotoxicity.

Example 4. Differential Response of Neurons, Microglia, Astrocytes and Neuron-Astrocyte Co-Cultures to Tat and PAM To ascertain the findings obtained from iTat mice above and to elucidate relative roles of each type of brain cells in the interaction among Tat neurotoxicity, PAM/α7 nAChR, and p38 MAPK signaling pathway, primary cortical neurons, microglia, and astrocytes were isolated from Wt and α7 nAChR knockout mice, and cultured in the presence of Tat-containing conditioned medium (Tat-CM) or its control conditioned medium (Ctrl-CM) and in the presence of PAM and PNU-282987 (P2), or its solvent control DMSO for 24 hours, and determined expression levels of PSD-95, Iba-1, GFAP and p-p38 and p38 in these cells by Western blotting. PNU-282987 (P2) was used as an α7 nAChR agonist in these in vitro experiments.

Figure 4A:
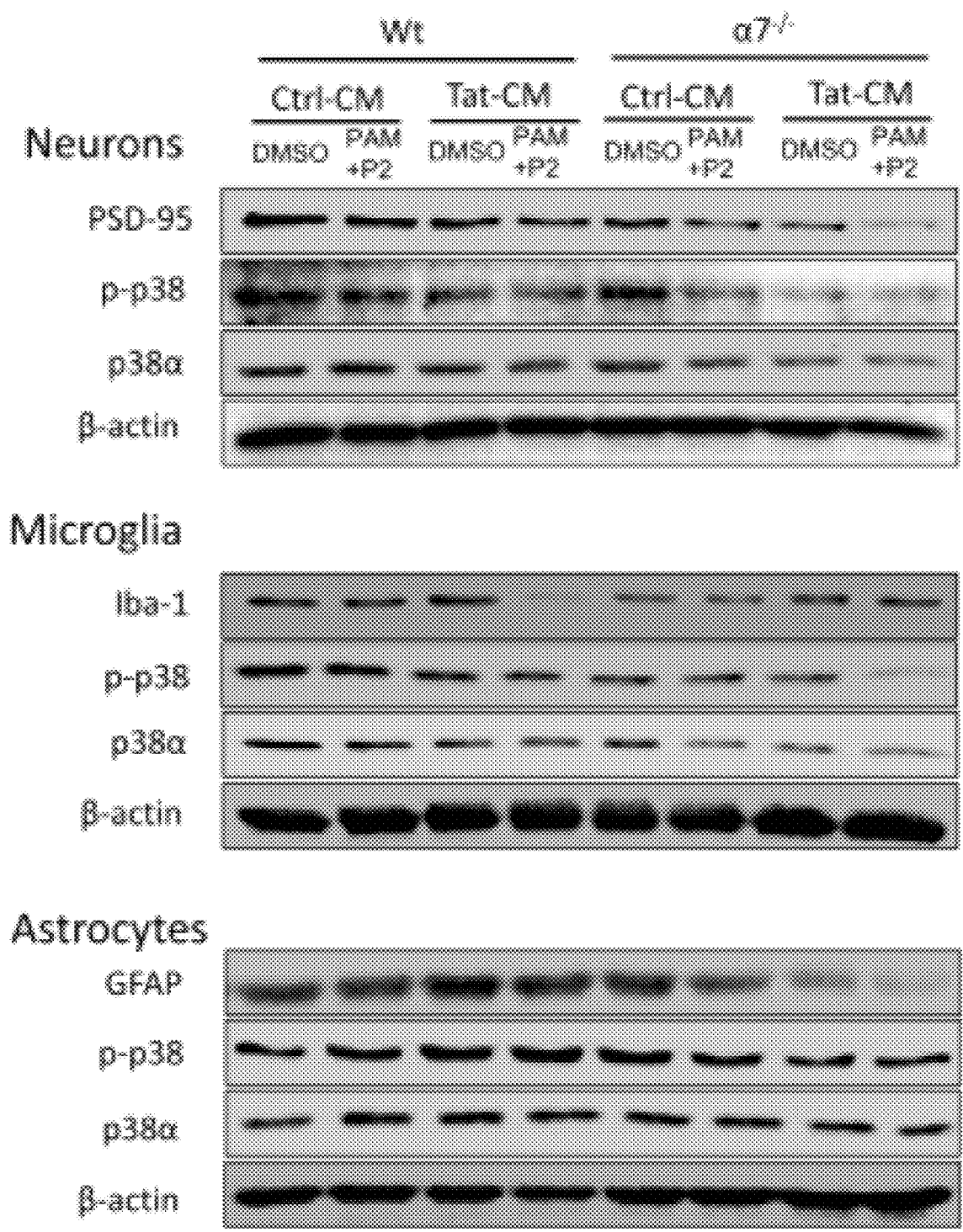
Figure 4B:
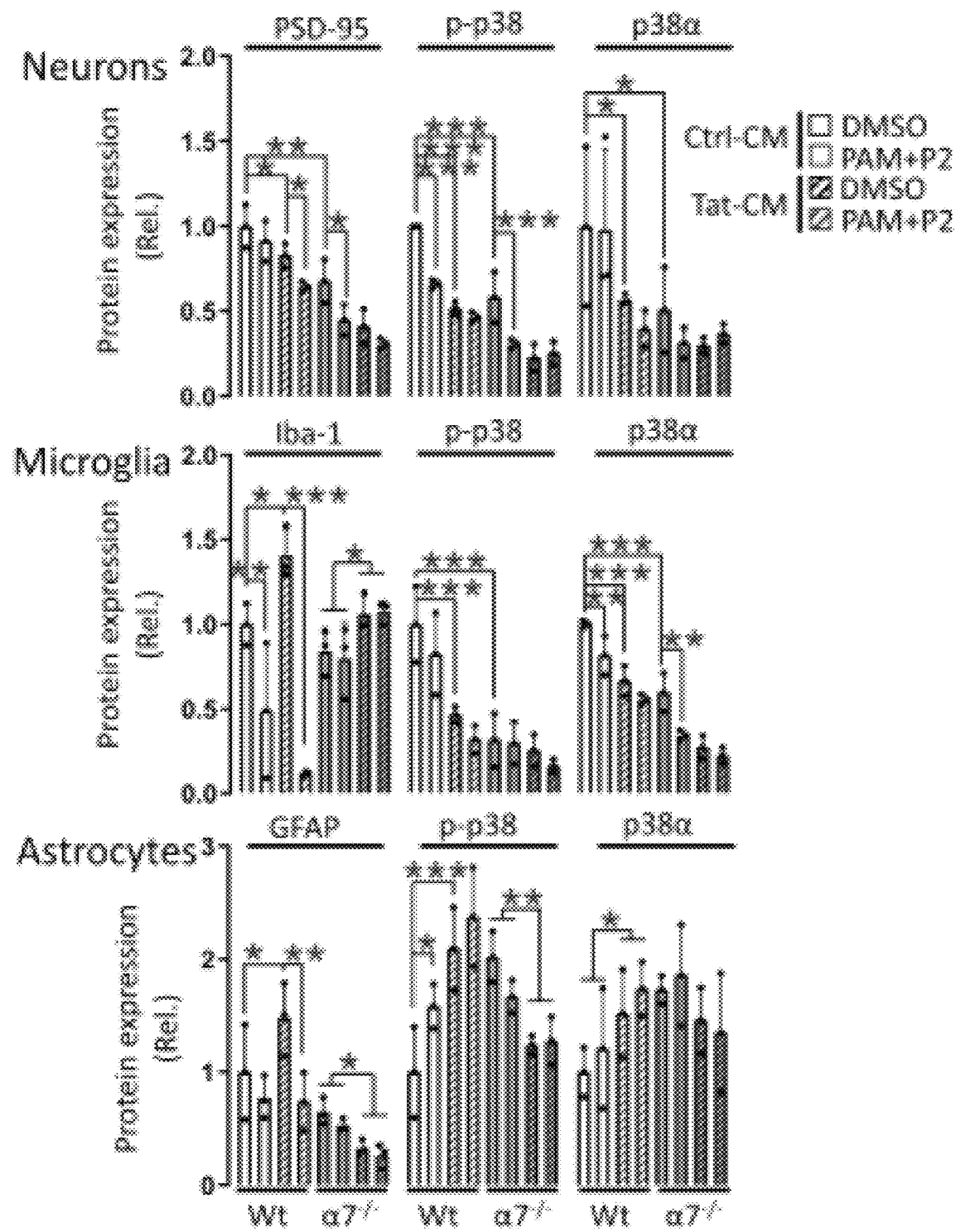
Figure 4C:
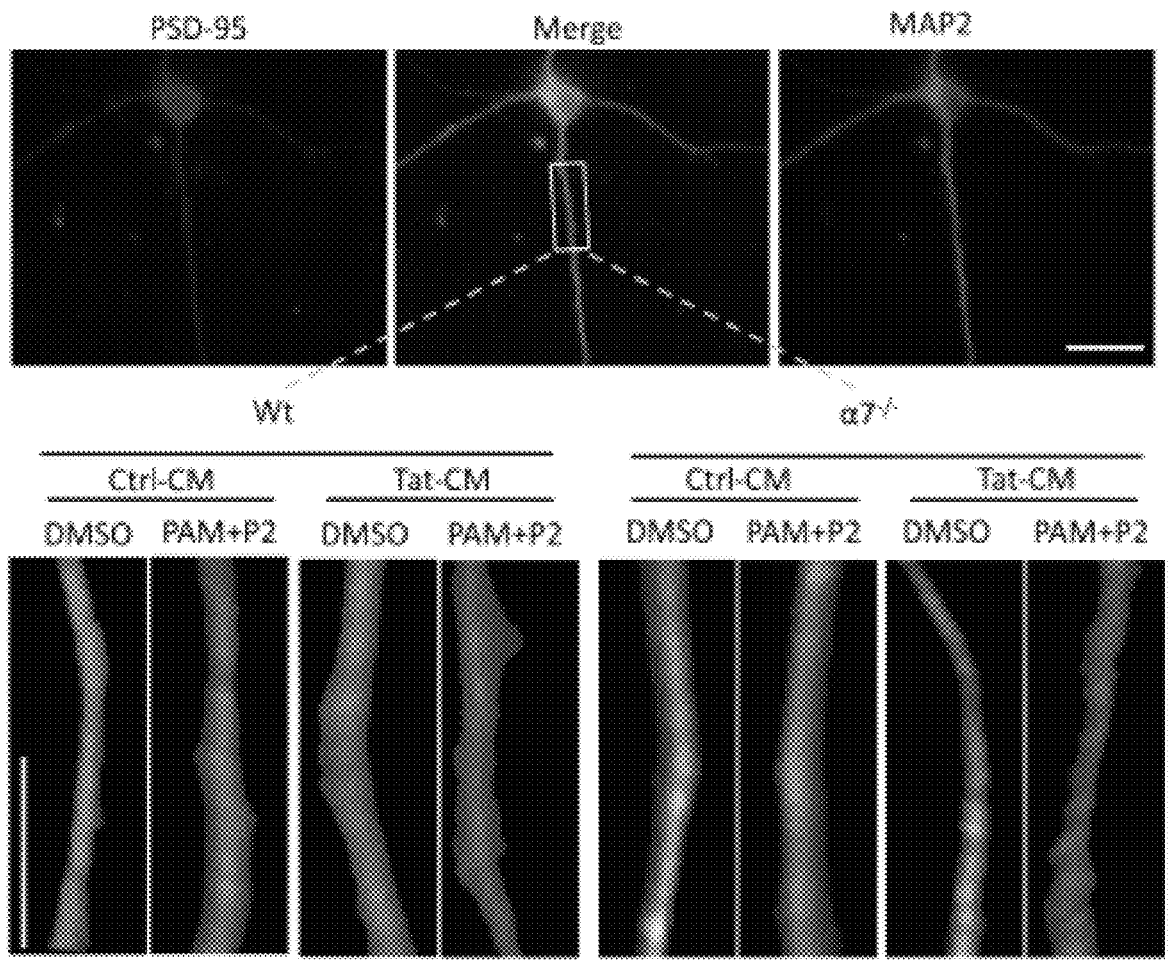
Figure 4D:
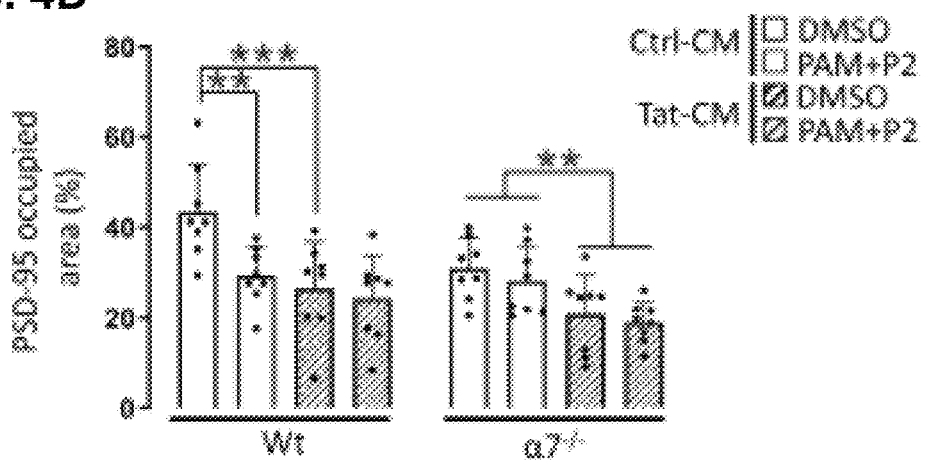
Figure 4F:
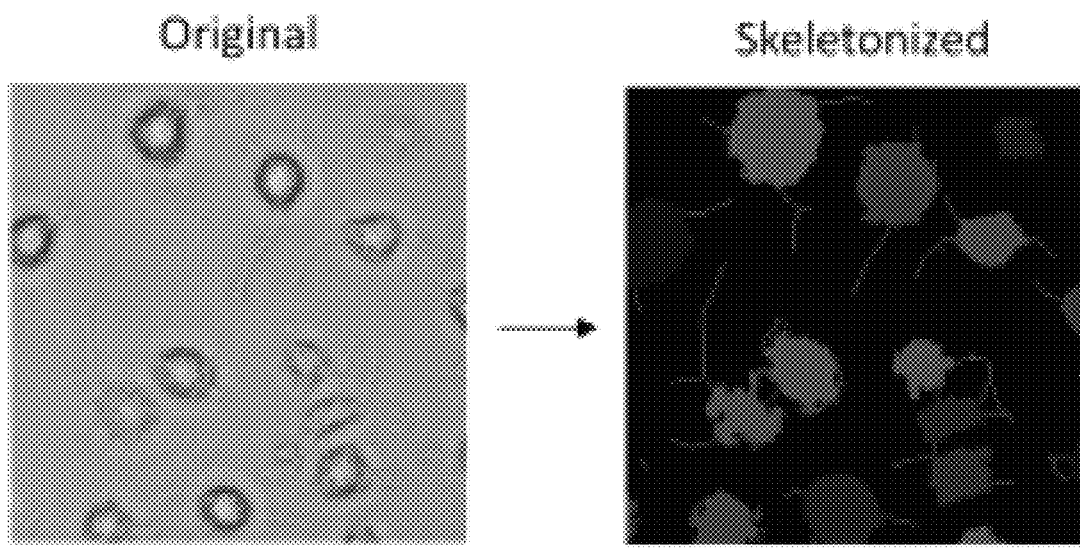
Figure 4G:
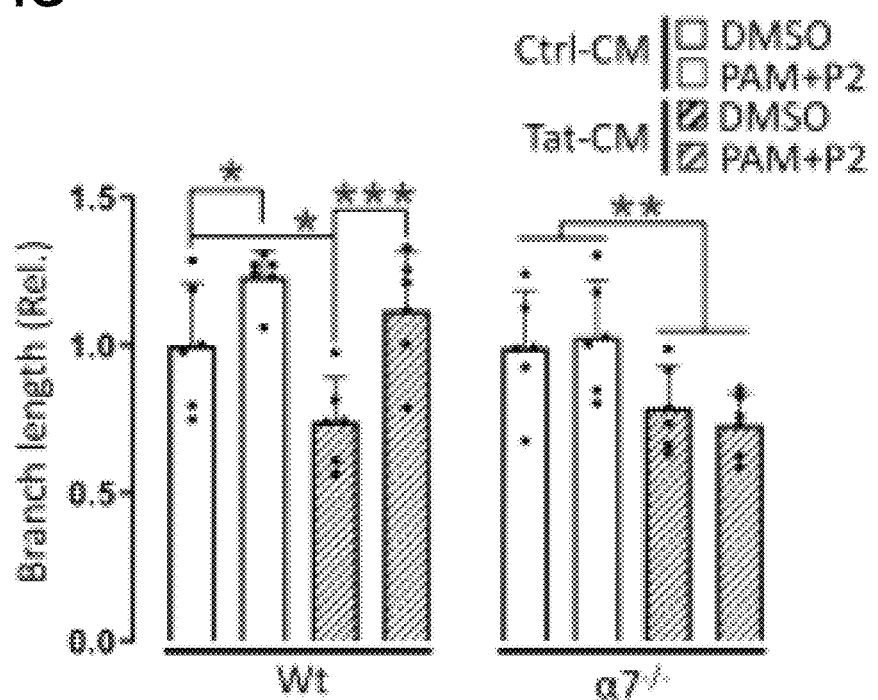

In primary cortical neurons of Wt mice, treatment of Tat, PAM+P2, or Tat plus PAM+P2 all showed lower PSD-95, p-p38 and p38, than the control treatment, while primary cortical neurons of α7⁻/⁻ mice showed similar effects, and treatments of these neurons with Tat, PAM+P2, or Tat plus PAM+P2 showed no further changes (upper panels, FIGS. 4A & B). In microglia of Wt mice, PAM+P2 or Tat plus PAM+P2 showed lower Iba-1, p-p38, and p38, while Tat alone increased Iba-1; In microglia of α7⁻/⁻ mice, only Tat (plus DMSO or PAM+P2) has higher Iba-1 than its control (plus DMSO or PAM+P2), and there were no differences of Iba-1 between DMSO and PAM+P2 (middle panels, FIGS. 4A & B), which were consistent with our findings in CORT (FIGS. 2D & E). Moreover, primary microglia of Wt and α7$^{-/-}$ mice under different treatments were visualized for their morphology (FIG. 4E), skeletonized (FIG. 4F), and calculated for the total length of the branches, indicative of microglia activation (FIG. 4G). In microglia of Wt mice, Tat had shorter of branches than its control, while PAM+P2 had longer branches in both Tat and its control treatments. In microglia of α7$^{-/-}$ mice, Tat had shorter branches than its control and there were no differences of the branch lengths between DMSO and PAM+P2. In astrocytes of Wt mice, Tat had higher GFAP, p-p38, and p38, while Tat plus PAM+P2 had lower GFAP, but maintained the higher level of p-p38 and p38; In astrocytes of α7$^{-/-}$ mice, only Tat (plus DMSO or PAM+P2) had lower GFAP and p-p38 than its control (plus DMSO or PAM+P2) and there were no differences of GFAP and p38 between DMSO and PAM+P2 (lower panels, FIGS. 4A & B), which were also consistent with the findings in CORT (FIGS. 2D & E).

In addition, immunofluorescence staining was performed on primary cortical neurons for PSD-95 (FIG. 4C) and quantified PSD-95 expression. Consistent with the findings from Western blotting, Tat or PAM+P2 had lower PSD-95 than its control in Wt neurons, and only Tat (DMSO and PAM+P2) had lower PSD-95 than its control (DMSO and PAM+P2) in α7$^{-/-}$ neurons and there were no differences of PSD-95 between DMSO and PAM+P2 (FIG. 4D).

Figure 5A:
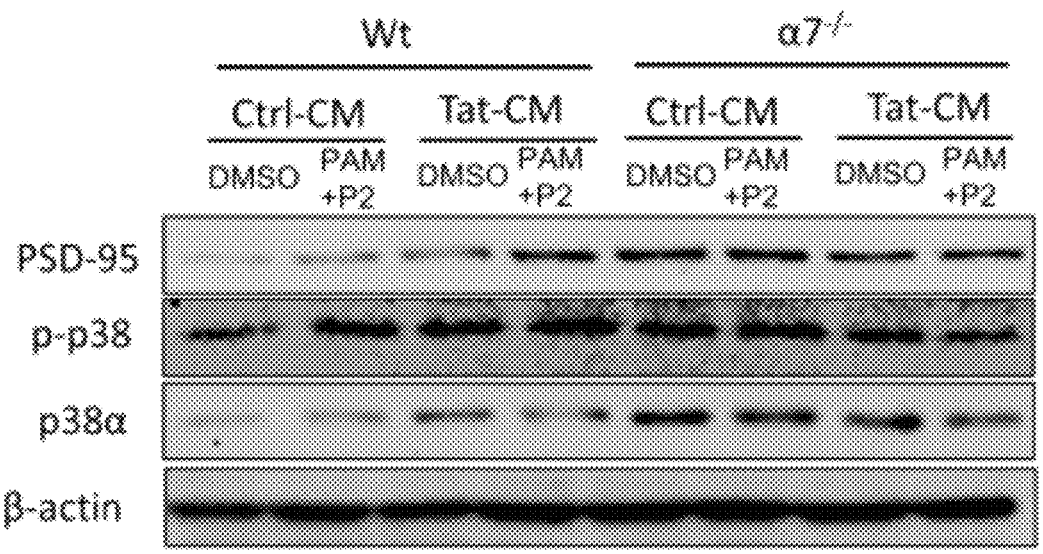
FIG. 5A-FIG. 5D show the response of neuron-astrocyte co-cultures to Tat and PAM. Primary cortical neurons-astrocytes were isolated from one-day old pups of Wt and α7$^{-/-}$ mice, treated with the conditioned medium from pcDNA3-transfected cells (Ctrl-CM) or pcDNA3-Tat-transfected cells (Tat-CM) and PNU-125096 (PAM, 1 μM) and an α7 agonist PNU-282987 (P2, 0.5 μM) for 24 hr, and harvested to determine expression of PSD-95, p-p38, and p38 and β-actin by Western blotting (FIG. 5A). Protein expression was quantitated (FIG. 5B). Primary neurons were also double immunostained for PSD-95 (red) and MAP2 (green) (FIG. 5C) and quantitated for PSD-95 (FIG. 5D). Multiple independent repeats were used for statistical analysis (n=3/group for Western blotting). p<0.05 was considered significant and marked as *; p<0.01 and p<0.001 were both considered highly significant and marked as  and *, respectively. Scale bars (FIG. 5C): 10 μm.
Figure 5B:
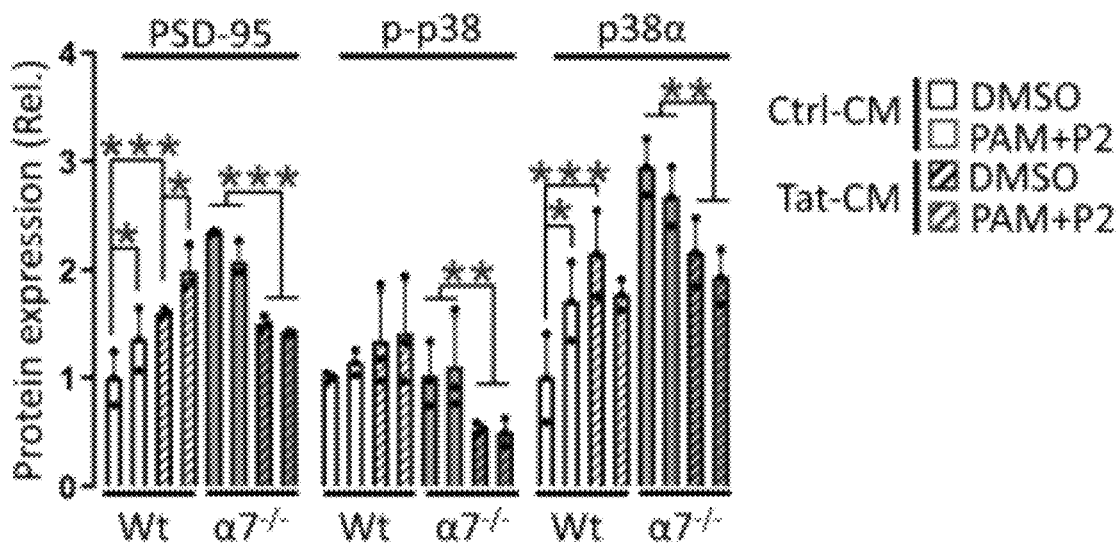
Figure 5C:
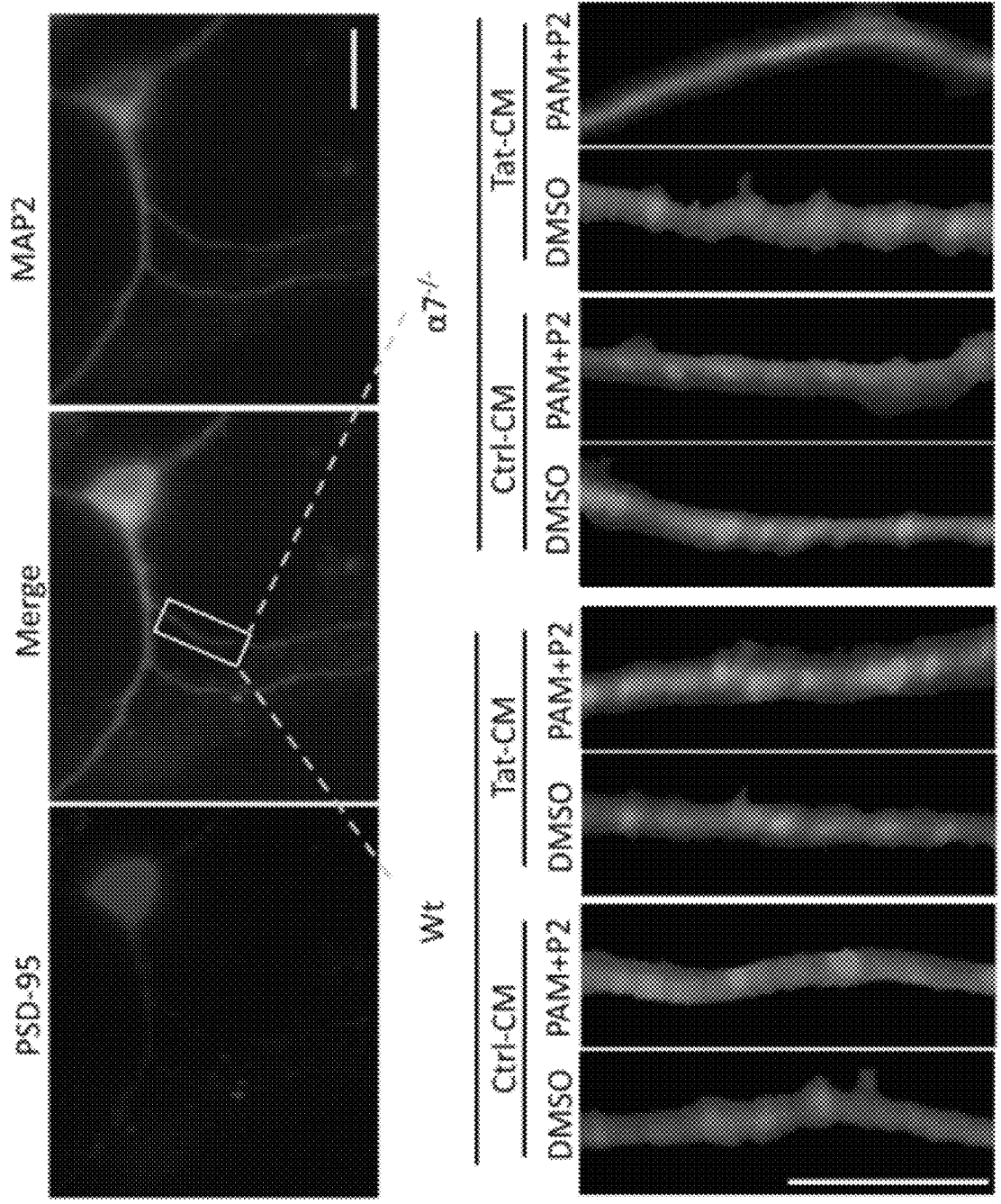
Figure 5D:
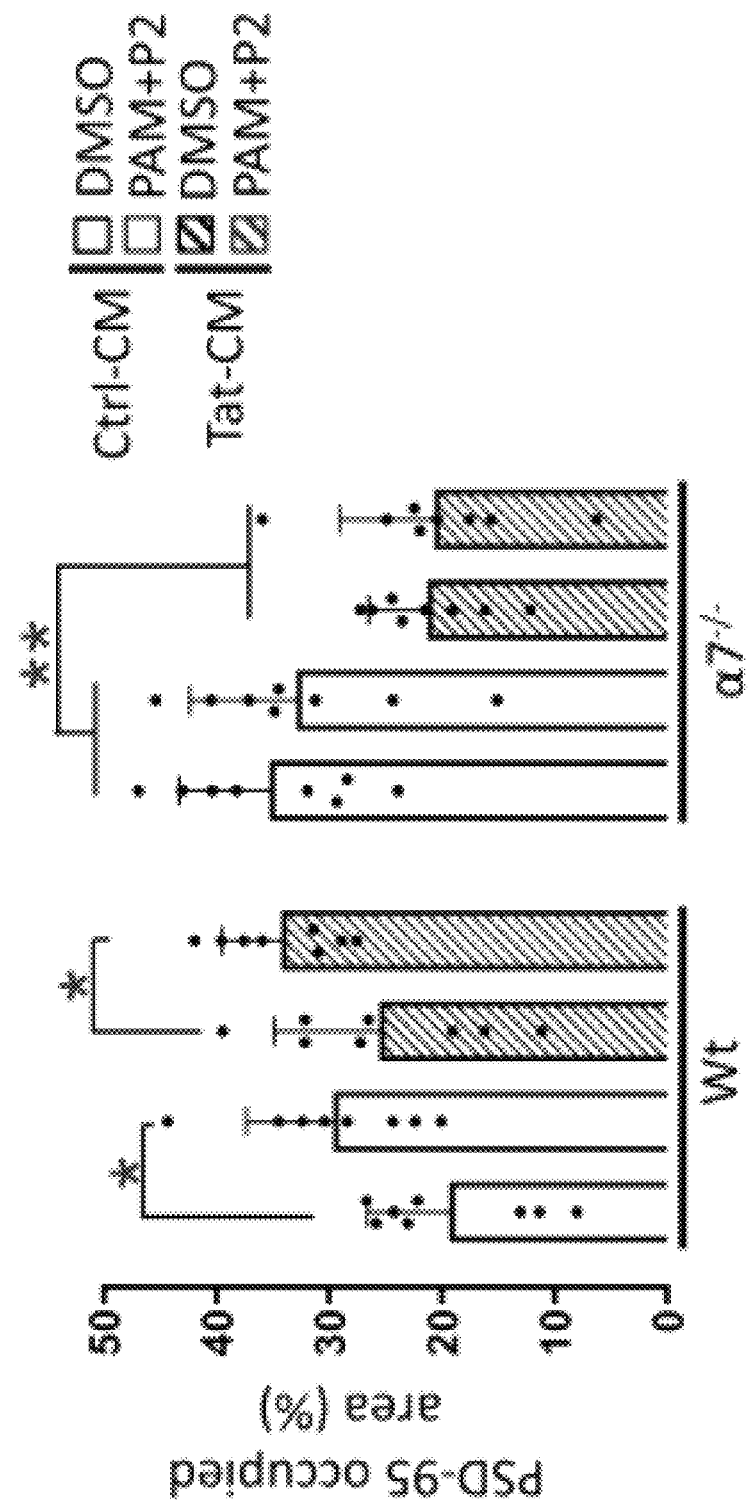

To determine whether neuron-astrocyte interaction would be important for the interaction among Tat neurotoxicity, PAM/α7 nAChR, and p38 MAPK signaling pathway, similar experiments were performed using primary cortical neurons-astrocyte co-cultures from Wt and α7 nAChR knockout mice. In the neuron-astrocyte co-cultures of Wt mice, PAM+P2, Tat, or Tat plus PAM+P2 all had higher PSD-95, p-p38, and p38, while in the neuron-astrocyte co-cultures of α7$^{-/-}$ mice, only Tat (plus DMSO or PAM+P2) has lower PSD-95, p-p38 and p38 than its control (plus DMSO or PAM+P2) and there were no differences of PSD-95, p-p38 and p38 between DMSO and PAM+P2 (FIGS. 5A & B). Similar results were obtained for PSD-95 in neuron-astrocyte co-cultures (FIGS. 5C & D).

Taken together, these results demonstrate that Tat treatment led to significant lower PSD-95 in neurons and higher PSD-95 in neuron-astrocyte co-cultures, higher Iba-1 in microglia, higher GFAP in astrocytes, while PAM treatment led to lower PSD-95 in neurons, higher PSD-95 in neuron-astrocyte co-cultures, lower Iba-1 in microglia, and lower GFAP in astrocytes, and α7 nAChR knockout plus Tat led to lower p-p38 and p38 with differences in neurons, microglia, astrocytes, and neuron-astrocyte co-cultures. PSD-95 staining and microglia morphology showed similar results. These findings are consistent with the in vivo findings in mouse CORT (FIGS. 1E & F; FIGS. 2D & E) and suggest that both microglia and astrocytes are important for the interaction among Tat neurotoxicity, PAM/α7 nAChR, and p38 MAPK signaling pathway.

Figure 6A:
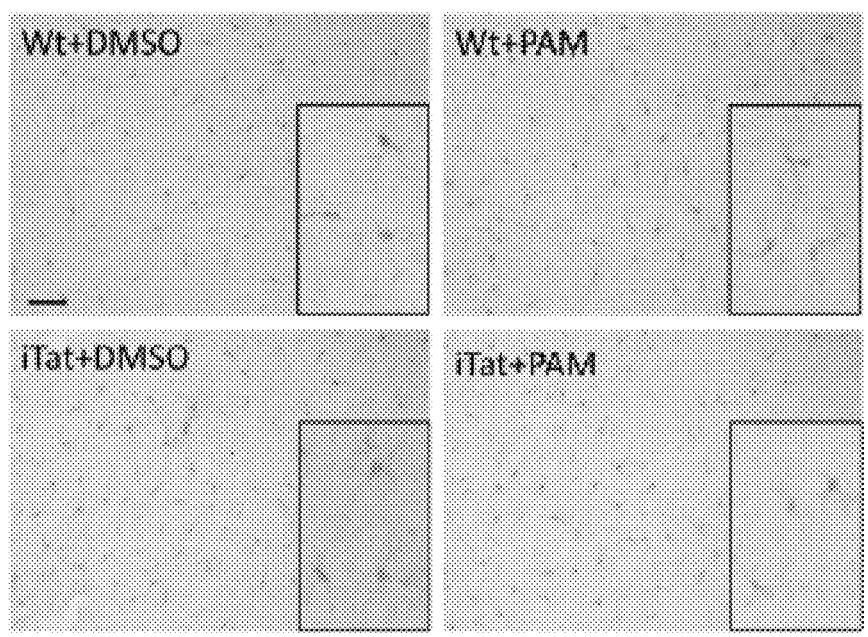
FIG. 6A-FIG. 6E show microglia activation by PAM in CORT of iTat mice and α7$^{-/-}$iTat mice. The brains from FIG. 1 were dissected, fixed, sectioned and stained for Iba-1 (FIG. 6A). Microglia morphologies were skeletonized (FIG. 6B), and the total length and endpoints of branches in three brain regions including prefrontal, parietal and occipital CORT were quantified and averaged from three sections of each mouse (n=6/group, 3 males, and 3 females) (FIG. 6C). Similarly, the brains from FIG. 2 were processed and stained for Iba-1 (FIG. 6D), skeletonized and quantitated (FIG. 6E). The Wt+DMSO group was used as a reference and set as 1. p<0.05 was considered significant and marked as *; p<0.01 and p<0.001 were both considered highly significant and marked as  and *, respectively. Scale bars (FIG. 6A): 200 μm.
Figure 6B:
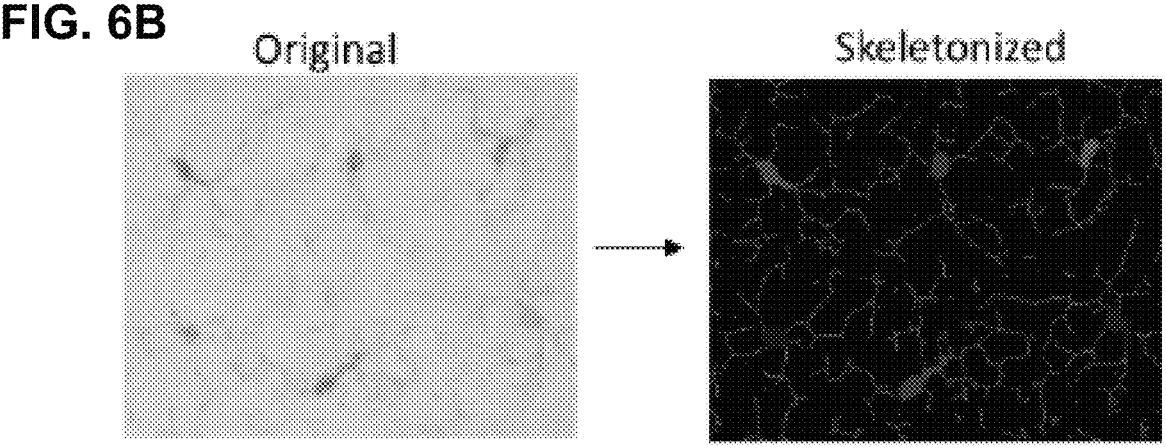
Figure 6C:
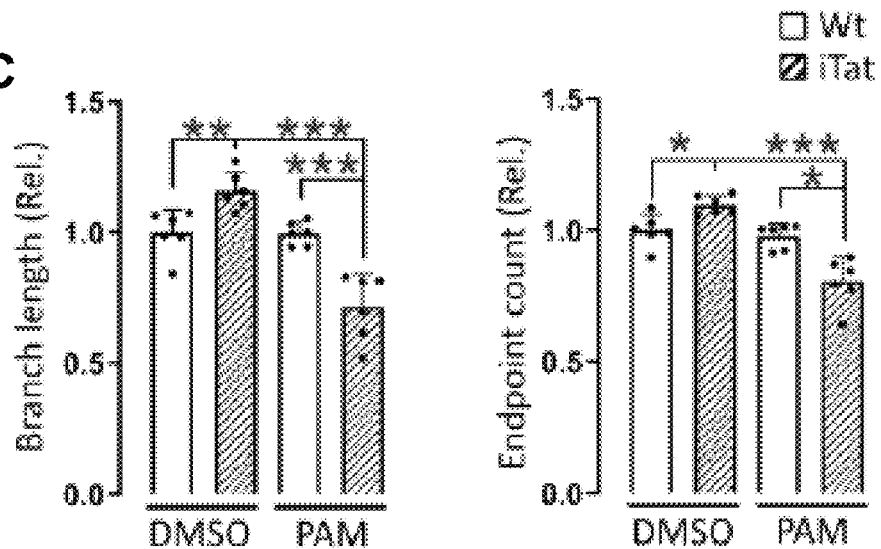
Figure 6D:
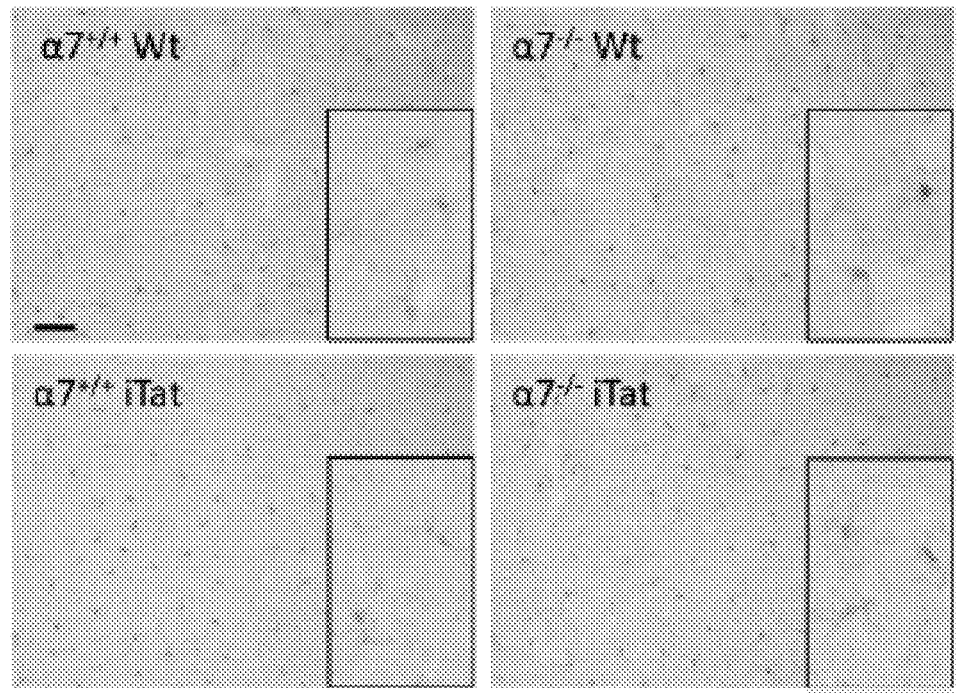
Figure 6E:
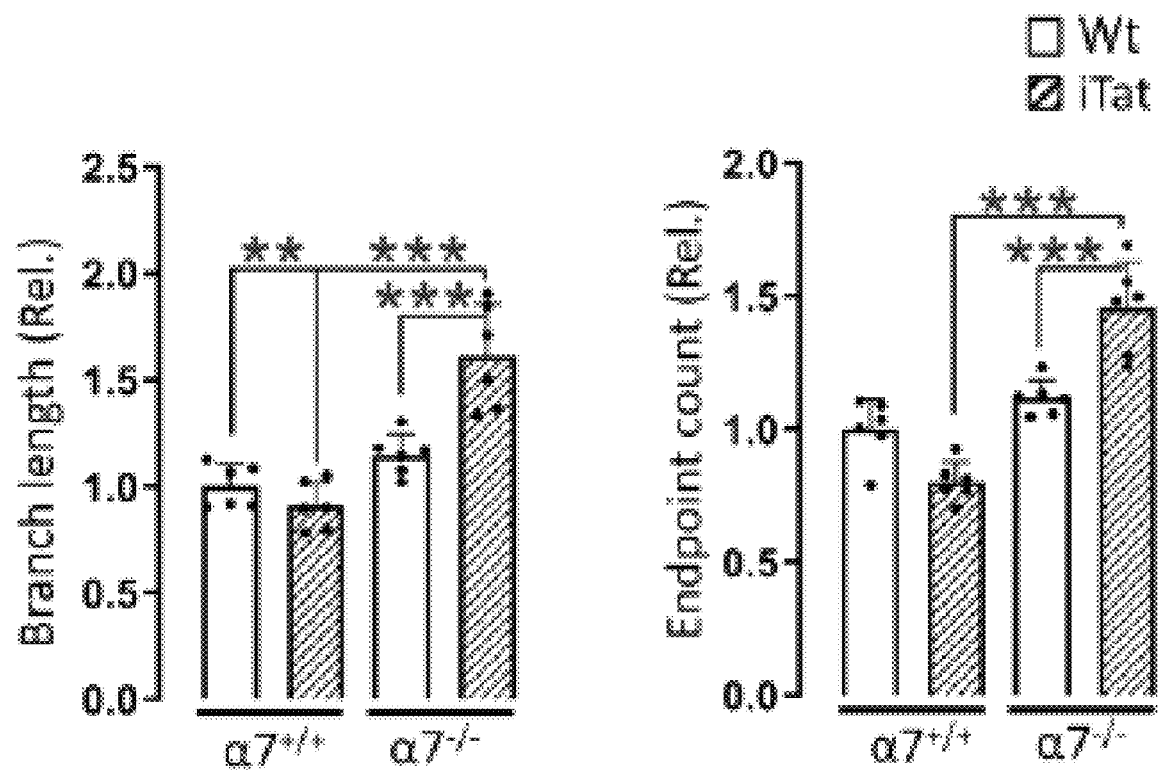

Example 5. Microglia Activation in Mouse Cortex in Response to Tat, PAM and α7 nAChR Knockout To further determine the relationship between microglia activation, Tat neurotoxicity, and PAM/α7 nAChR, immunohistochemistry staining was performed on microglia in CORT of Wt and iTat mice treated with and without PAM (FIG. 1). Microglia were visualized for their morphology (FIG. 6A), and skeletonized (FIG. 6B), and quantitated for the number of branches and endpoints (FIG. 6C). iTat mice had more branches and endpoints that its Wt control, PAM-treated iTat mice had fewer branches and endpoints than PAM-treated Wt mice and DMSO-treated iTat mice. Similar immunohistochemistry staining was also performed with CORT of α7$^{+/+}$Wt, α7$^{+/+}$iTat, α7$^{-/-}$Wt, and α7$^{-/-}$iTat mice in the presence of PAM (FIG. 2). α7$^{-/-}$iTat mice had more branches and endpoints than α7$^{-/-}$Wt mice and α7$^{-/-}$iTat mice (FIGS. 6D & E). These findings further confirmed that microglia activation was directly involved in Tat neurotoxicity and its interaction with PAM/α7 nAChR.

Discussion

Figure 11A:
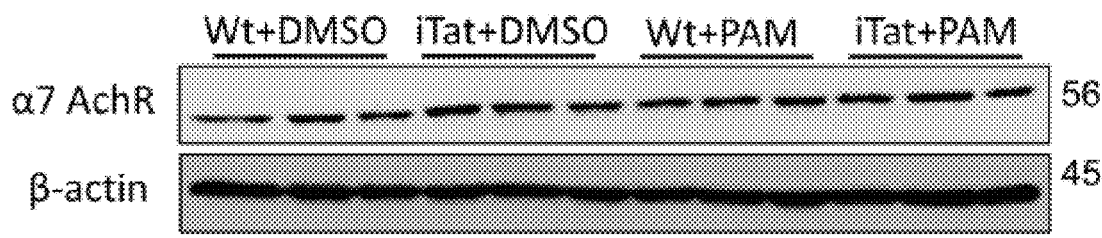
FIG. 11A-FIG. 11E show the α7 nAChR expression in the brain, cortical neurons, microglia, and astrocytes in response to Tat and PAM. Western blotting was performed in the same samples of FIG. 1D (FIG. 11A & FIG. 11B, mouse brain tissue, n=6/group, three males, and three females) and FIG. 4A (FIG. 11D & FIG. 11E, primary cells, and n=3/group) using an anti-α7 nAChR antibody. Immunofluorescent staining (FIG. 11C, scale bars 20 μm) of the brain tissues was also performed using an anti-α7 nAChR antibody. p<0.05 was considered significant and marked as *; p<0.01 and p<0.001 were both considered highly significant and marked as  and *, respectively.
Figure 11A:
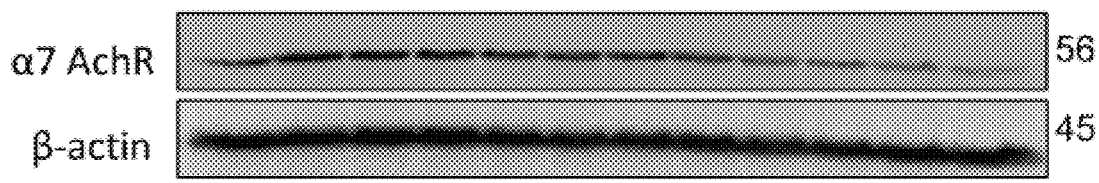
Figure 11B:
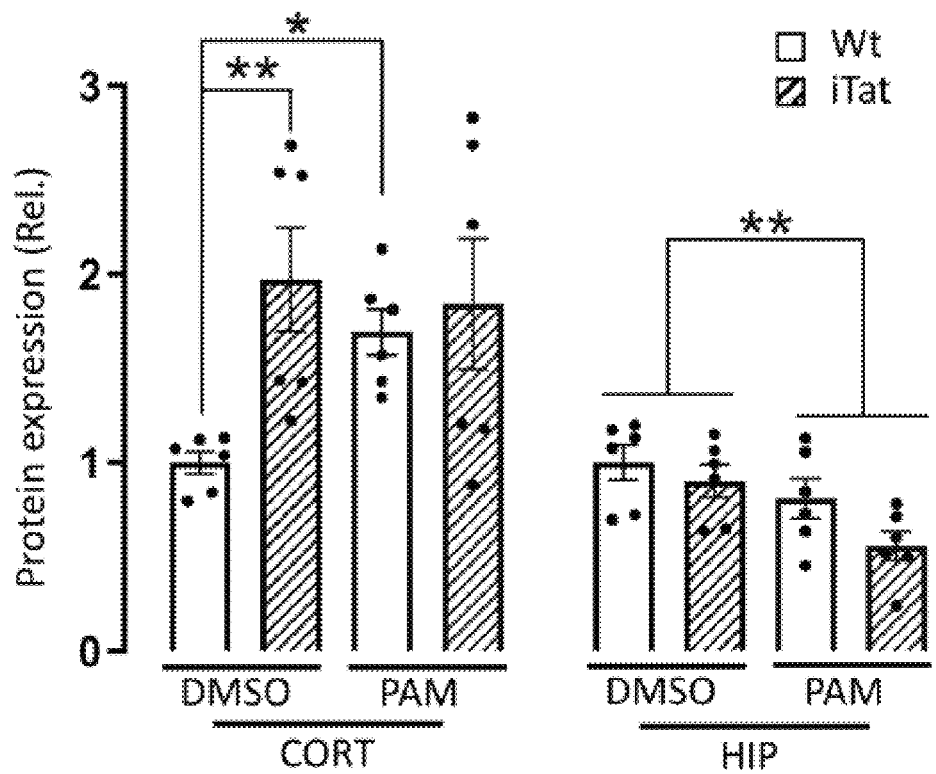
Figure 11C:
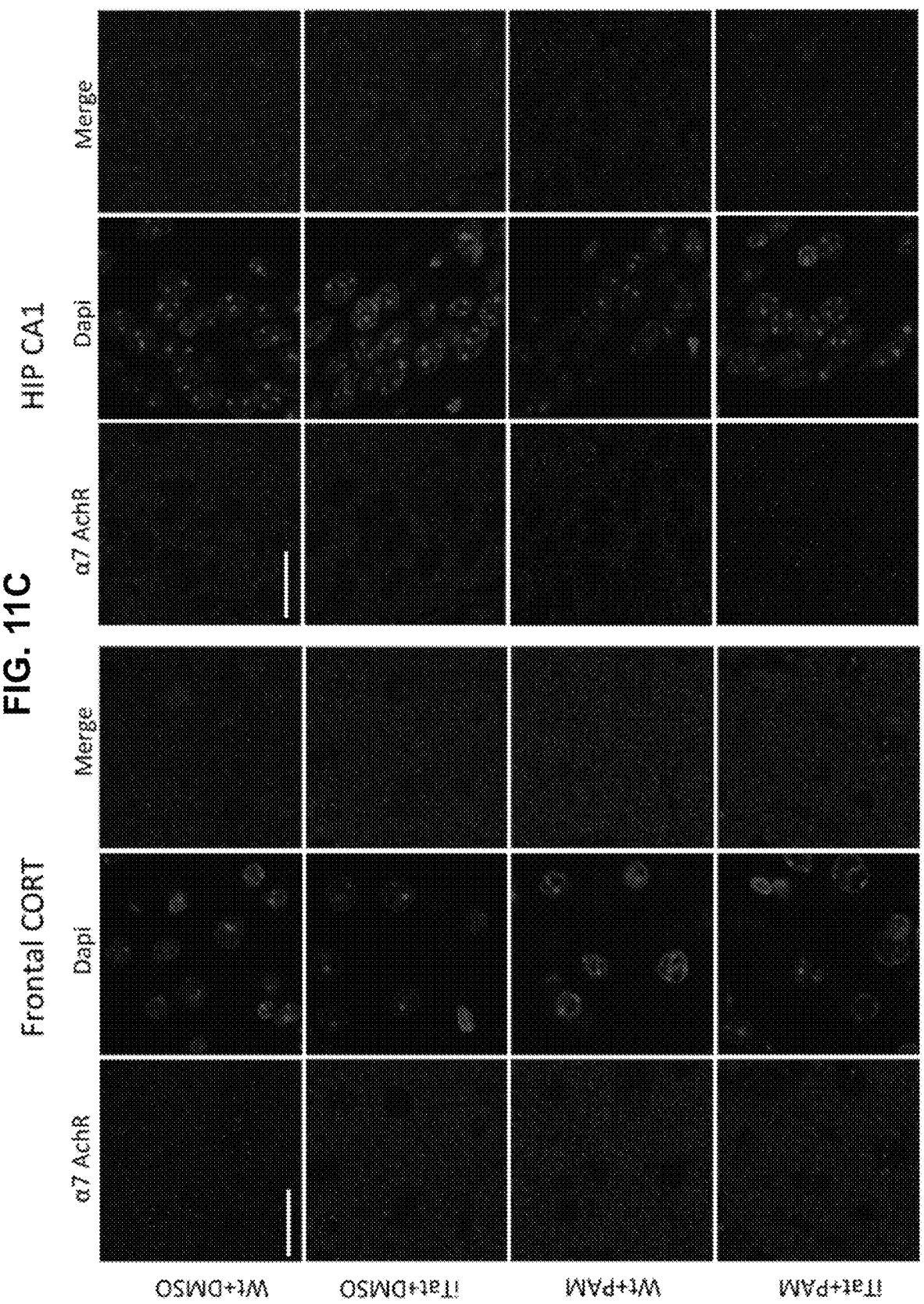
Figure 11D:
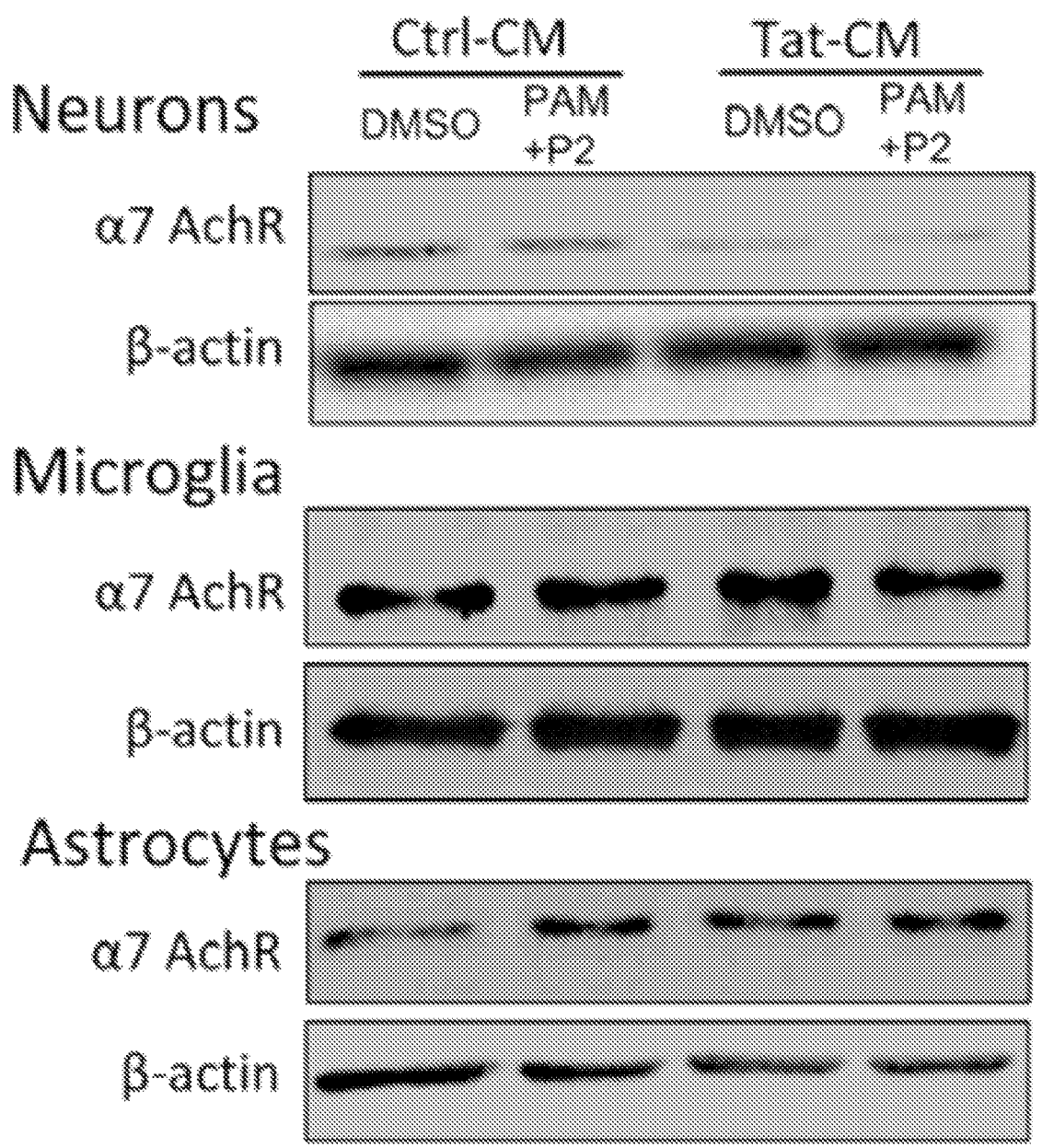
Figure 11E:
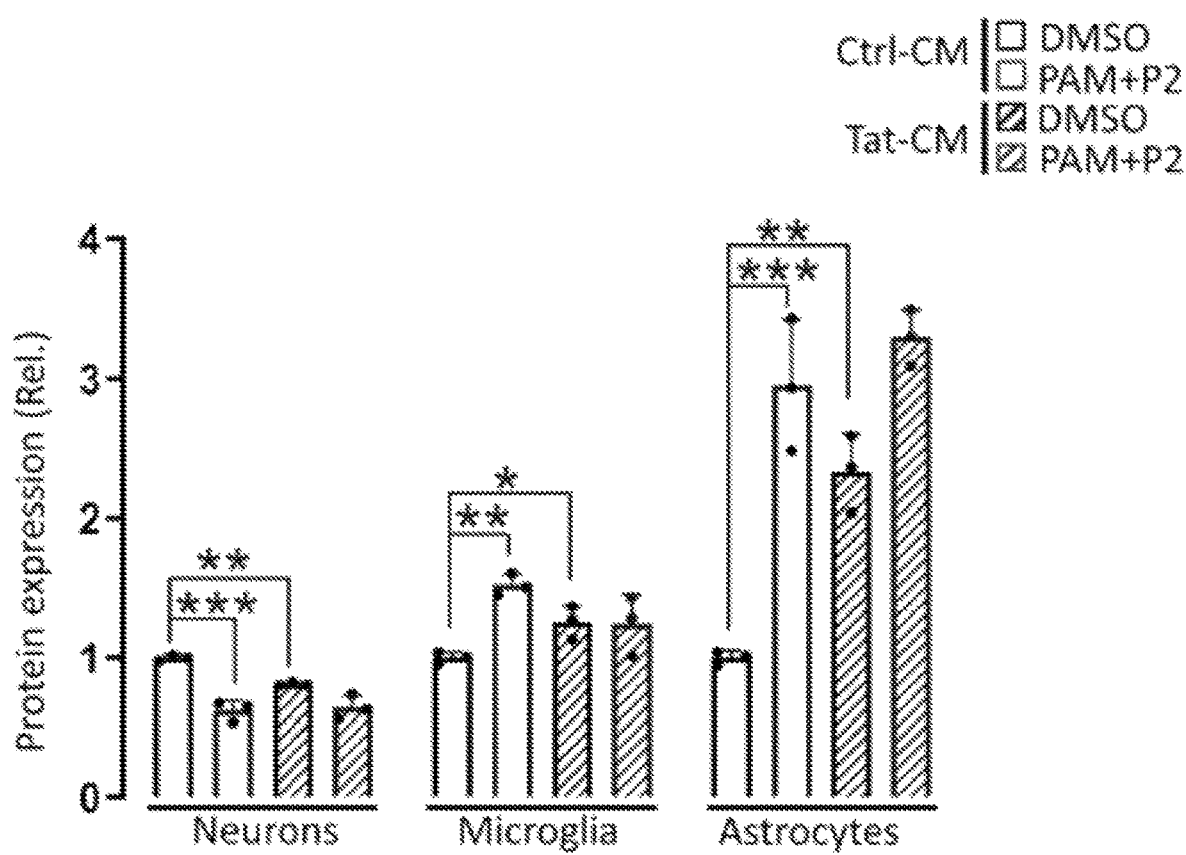

This study demonstrated for the first time that PAM treatment greatly improved locomotor activity, learning and memory of iTat mice and increased PSD-95 expression and decreased GFAP and Iba-1 expression in CORT of iTat mice. It also demonstrated that knockout of α7 nAChR abolished PAM protection against Tat-induced neurotoxicity. α7 nAChR expression was detected in both cortex and hippocampus of iTat mice, although its expression was increased in cortex by either Tat expression or PAM treatment but only decreased in hippocampus by both Tat expression and PAM treatment (FIG. 11A-11C). In addition, PAM/P2 treatment led to decreased α7 nAChR expression in neurons but increased α7 nAChR expression in microglia and astrocytes, while Tat led to increased α7 nAChR expression in microglia and astrocytes but decreased α7 nAChR expression on neurons (FIG. 11D & 11E). These results demonstrated that α7 nAChR expression was directly involved in PAM neuroprotective activity against Tat neurotoxicity, but changes of α7 nAChR expression in response to Tat and PAM treatment was brain region- and cell type-dependent. Thus, the changes of α7 nAChR expression in response to Tat and PAM treatment alone could not account for the PAM neuroprotective effects in this study. Furthermore, it is quite reasonable to assume that α7 nAChR is expressed in the brain of other rodent HAND models, even though no studies about α7 nAChR expression in these models are currently available.

In addition, this study showed that inhibition of p38 MAPK signaling pathway worsened Tat-induced learning and memory impairments and was associated with down-regulation of PSD-95 in both cortex and hippocampus. Inhibition of p38 MAPK signaling pathway has led to improved cognition, learning and memory in several neurological diseases.[78-83] Some beneficial effects were noted in the Wt mice when treated with p38 MAPK inhibitor SB239063. On the other hand, PSD-95 up-regulation and improved behaviors were noted with PAM-treated iTat mice while little p38 MAPK was altered in iTat mice in the absence of PAM treatment. These results together suggest p38 MAPK regulation of PSD-95 expression is involved in PAM-activated α7 nAChR-mediated protection against Tat neurotoxicity and that p38 MAPK activation is not involved in Tat neurotoxicity, at least at the level of Tat expression in the brain of these iTat mice. In vitro studies about the involvement of p38 MAPK on Tat neurotoxicity are not consistent. For instance, inhibition of p38 by SB203580 failed to block Tat-induced neurite losses and cell death in striatal neurons[84], but prevented Tat-induced apoptosis in cerebellar granule neurons[85]. Moreover, inhibition of p38 MAPK by a different inhibitor SB202190 decreased Tat-induced inflammation and oxidation in hippocampal slice cultures.[86] Several factors could contribute to these inconsistencies. First, the specificity of the inhibitors differs. SB203580 and SB202190 both have shown off-target effects.[87] SB 239063, the inhibitor used in this study is the second generation of p38 MAPK inhibitor and is much more selective and more popular for neurological disease studies[88]. Second, in vitro experimental systems differ. For example, different types of neuron cultures were used. Lastly and more plausibly, higher concentrations of Tat were often used in these in vitro experiments than that in the brain of the iTat mice, while Tat expression in the brain of iTat mice[89] is more relevant to that in the HIV infected brain in the era of anti-retroviral therapy.[90,91] Interestingly, it was noted that both female Wt and female iTat mice performed better in the OPT than male Wt and male iTat mice in response to SB239063, which was consistent with higher SYP in CORT of the female mice than male mice. These results suggest the unique roles of p38 MAPK signaling pathway in sex-dependent specific behavioral changes of iTat mice and that SYP expression in CORT is associated with the locomotor activity control.

Figure 12A:
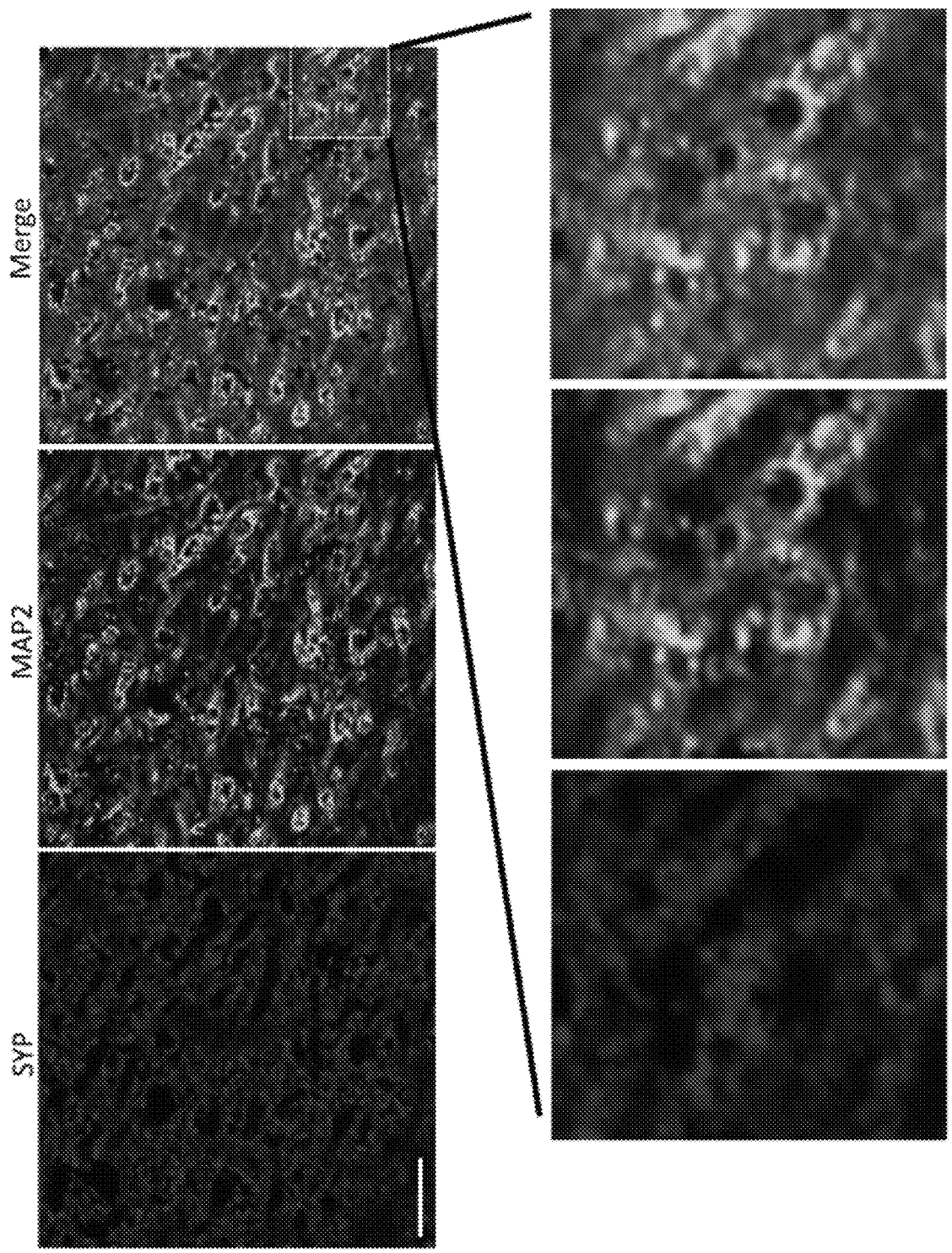
FIG. 12A-FIG. 12C show double immunofluorescent staining for SYP and MAP-2. SYP and MAP-2 were double stained in the mouse brain tissues (FIG. 12A). Immunofluorescent staining for SYP (α-SYP, Abcam, catalog #ab32127, and 1:500 dilution) was performed in the brain tissues (FIG. 12B & FIG. 12C) derived from the mice in FIG. 1-3. Scale bar: 20 μm (FIG. 12A-FIG. 12C).
Figure 12B:
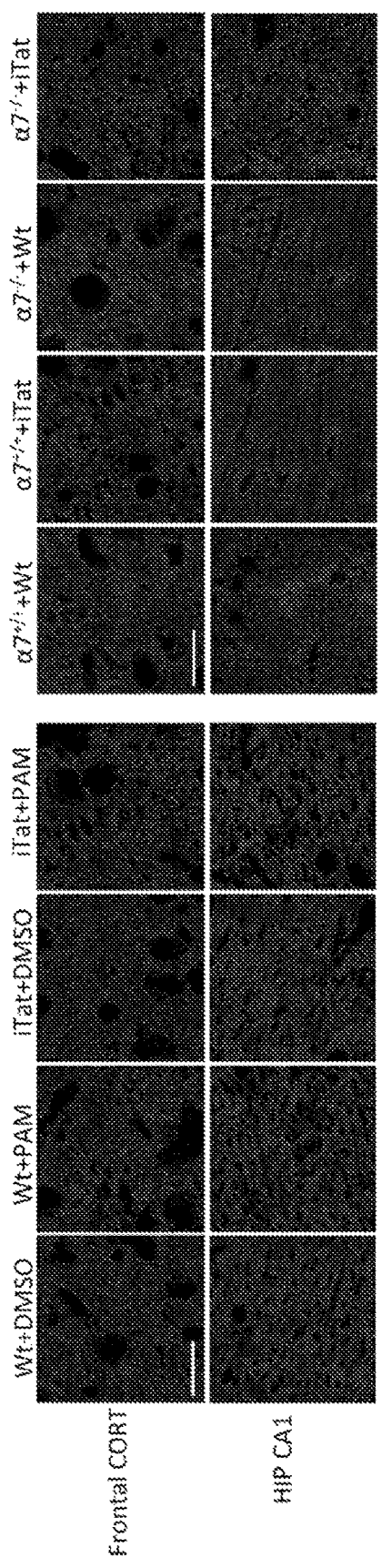
Figure 12C:
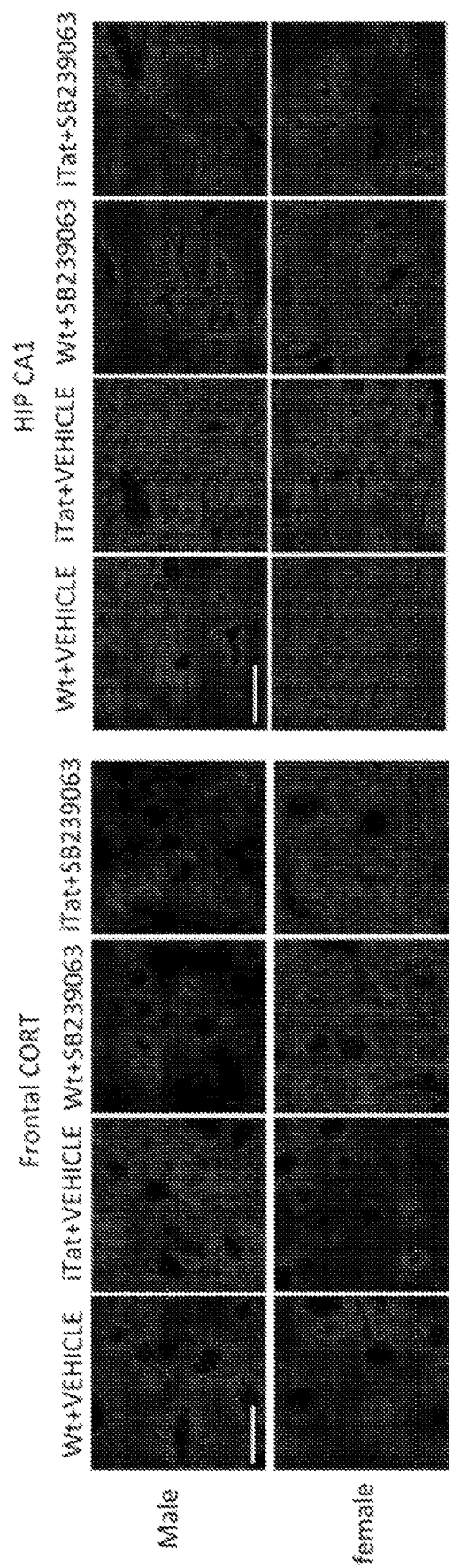

This study also determined neuropathological changes in response to PAM treatment and α7 nAChR knockout, by focusing on neuronal markers SYP and PSD-95, and microglia marker Iba-1 and astrocyte marker GFAP in two important brain regions CORT and HIP. SYP showed no significance changes in both CORT and HIP of iTat mice when treated with PAM in the presence and absence of α7 nAChR, which was further confirmed by immunofluorescent staining (FIG. 12). PSD-95 showed increases in both CORT and HIP of Wt and iTat mice and PAM treatment led to more increases, while α7 nAChR led to decreases of PSD-95 in both CORT and HIP of iTat mice in the presence of PAM. Similar results were obtained in our subsequent neuron-astrocyte co-cultures with and without α7 nAChR expression. Nevertheless, it has been shown that Tat induces PSD-95 down-regulation when Tat-expressing conditioned medium from astrocytes was used to treat neurons or using recombinant Tat protein in a transwell setting of astrocytes and neurons without direct contact.[37,92] These studies further support that astrocytes are the key regulator of Tat neurotoxicity and suggest that the cell-cell interaction between astrocytes and neurons is important for this regulatory role.

Figure 13A:
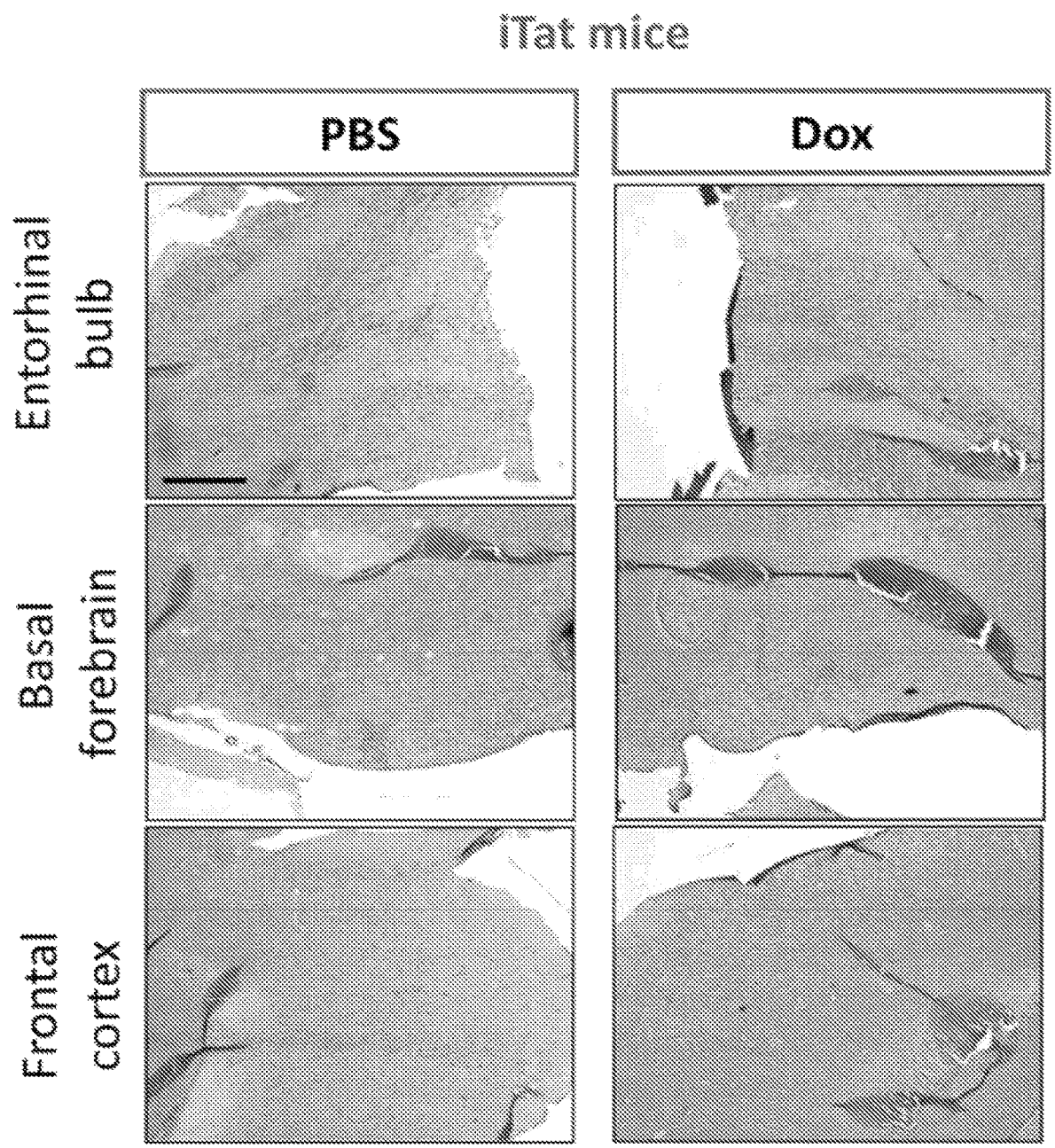
FIG. 13A-FIG. 13B show H&E staining of the brain tissues of iTat mice. iTat mice were given i.p. doxycycline (80 mg/kg/day) or PBS for seven days, anesthetized and sacrificed without perfusion. The brain was collected and sectioned using a cryostat (8 μm thickness). Nuclei and cytoplasm were stained by hematoxylin and eosin, respectively and then fixed.
Figure 13B:
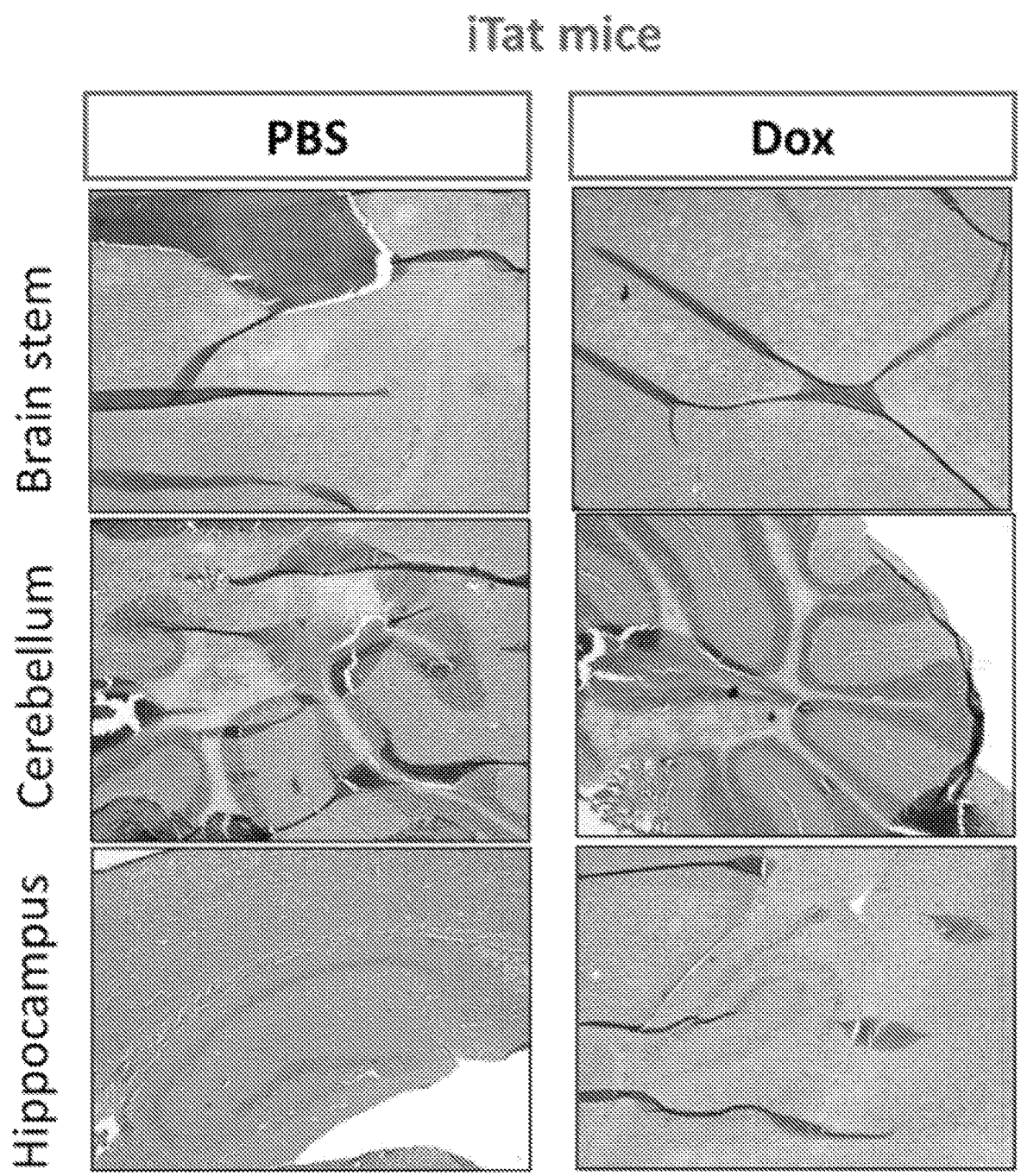
Figure 14A:
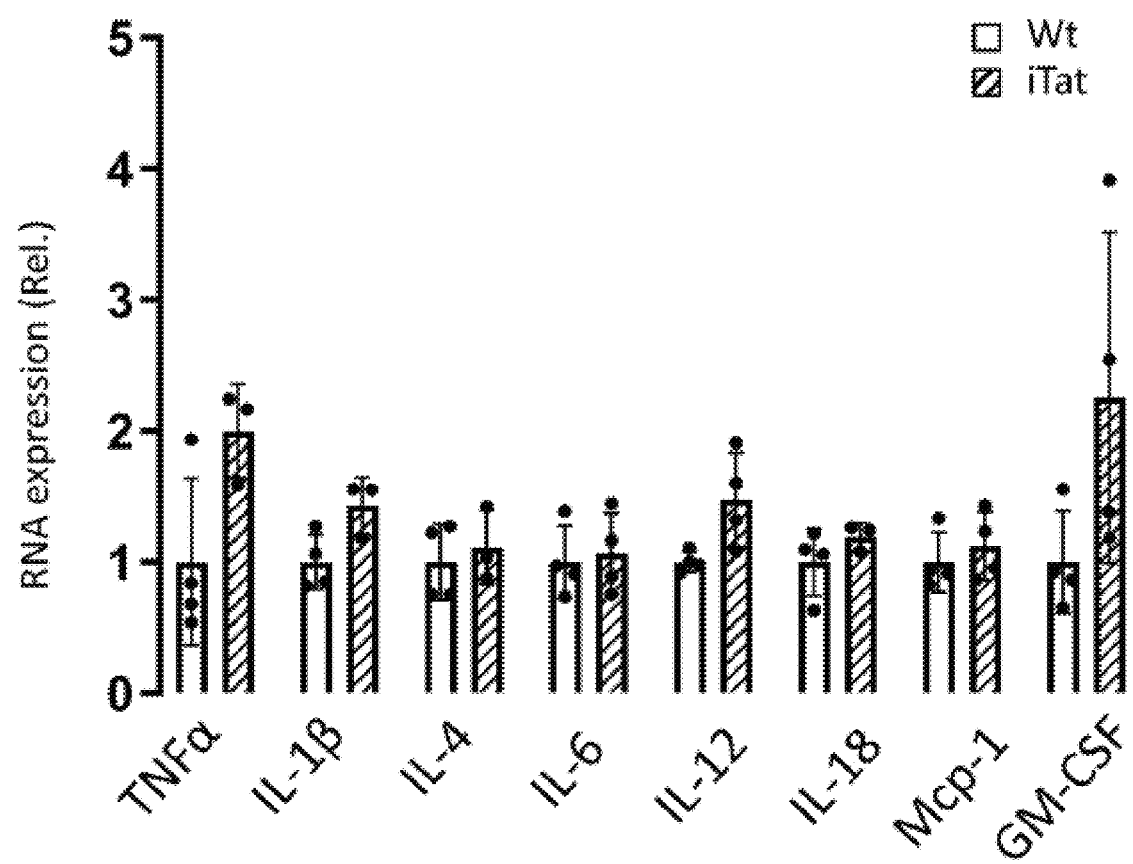
FIG. 14A-FIG. 14B show pro-inflammatory and anti-inflammatory cytokines RNA expression in iTat mice brain. Wt and iTat mice were given i.p. doxycycline (80 mg/kg/day) for seven days, the brain was collected for total RNA isolation using TRIzol. (Thermofisher, Catalog number: 15596026). cDNA was synthesized from 1 μg RNA using a Script II RT kit (Bio-Rad, Catalog number: 1708840) and used as a template for qPCR using a SYBR Green kit (Bio-Rad, Catalog number: 1725270). Bio-Rad CFX Manager Software was used to calculate gross-threshold (CT) values. The $2^{(-\Delta\Delta CT)}$ was calculated to represent the fold change of gene expression and normalized using β-actin as a reference. mRNA expression of TNFα, IL-1β, IL-4, IL-6, IL-18, Mcp-1, IL-12, GM-CSF, IL-10, IFN-γ, and IL-1β were further quantified (FIG. 14A & FIG. 14B). Amplification signals for IL-10, IFN-γ, and IL-12β were not detected until PCR cycles reached over 32. All the primers was as follows: TNF-α: forward: 5'-CAC CAC GC TCT TCT GTC TAC T-3' (SEQ ID NO:01), reverse: 5'-TTT GCT ACG ACG TGG GCT A-3' (SEQ ID NO:02); IL-1β: forward: 5'-GAA ATG CCA CCT TTT GAC AGT GA-3' (SEQ ID NO:03), reverse: 5'-AGT GAT ACT GCC TGC CTG AAG-3' (SEQ ID NO:04); IL-4: forward: 5'-GAG ACT CTT TCG GGC TTT TC-3' (SEQ ID NO:05), reverse: 5'-TGA TGC TCT TTA GGC TTT CCA-3' (SEQ ID NO:06); IL-6: forward: 5'-ACA AGT CCG GAG AGG AGA CT-3' (SEQ ID NO:07), reverse: 5'-TTC TGC AAG TGC ATC ATC GT-3' (SEQ ID NO:08); IL-12: forward: 5'-TAC TAG AGA GAC TTC TTC CAC AAC AAG AG-3' (SEQ ID NO:09), reverse: 5'-TCT GGT ACA TCT TCA AGT CCT CAT AGA-3' (SEQ ID NO:10); IL-18: forward: 5'-GAC AAC ACG CTT TAC TTT ATA CCT GA-3' (SEQ ID NO:11), reverse: 5'-GTG AAG TCG GCC AAA GTT GT-3' (SEQ ID NO:12); Mcp-1: forward: 5'-CAC TCA CCT GCT GCT ACT CAT-3' (SEQ ID NO:13), reverse: 5'-ATT CCT TCT TGG GGT CAG CA-3' (SEQ ID NO:14); GM-CSF: forward: 5'-TGC TTT TGT GCC TGC GTA ATG-3' (SEQ ID NO:15), reverse: 5'-TCC AAG CTG AGT CAG CGT TTT C-3' (SEQ ID NO:16); IL-10: forward: 5'-CCA GAA ATC AAG GAG CAT TT-3' (SEQ ID NO:17), reverse: 5'-CAC ACT GCA GGT GTT TTA GC-3' (SEQ ID NO:18); IFN-γ: forward: 5'-GGA TGC ATT CAT GAG TAT TGC-3' (SEQ ID NO:19), reverse: 5'-CCT TTT CCG CTT CCT GAG G-3' (SEQ ID NO:20); IL-12b: forward: 5'-GAC CAT CAC TGT CAA AGA GTT TCT AGA T-3' (SEQ ID NO:21), reverse: 5'-AGG AAA GTC TTG TTT TTG AAA TTT TTT AA-3' (SEQ ID NO:22); β-actin: forward: 5'-AGA GAA GTG GGG TGG CTT TT-3' (SEQ ID NO:23), reverse: 5'-AAA CTG GAA CGG TGA AGG TG-3' (SEQ ID NO:24).
Figure 14B:
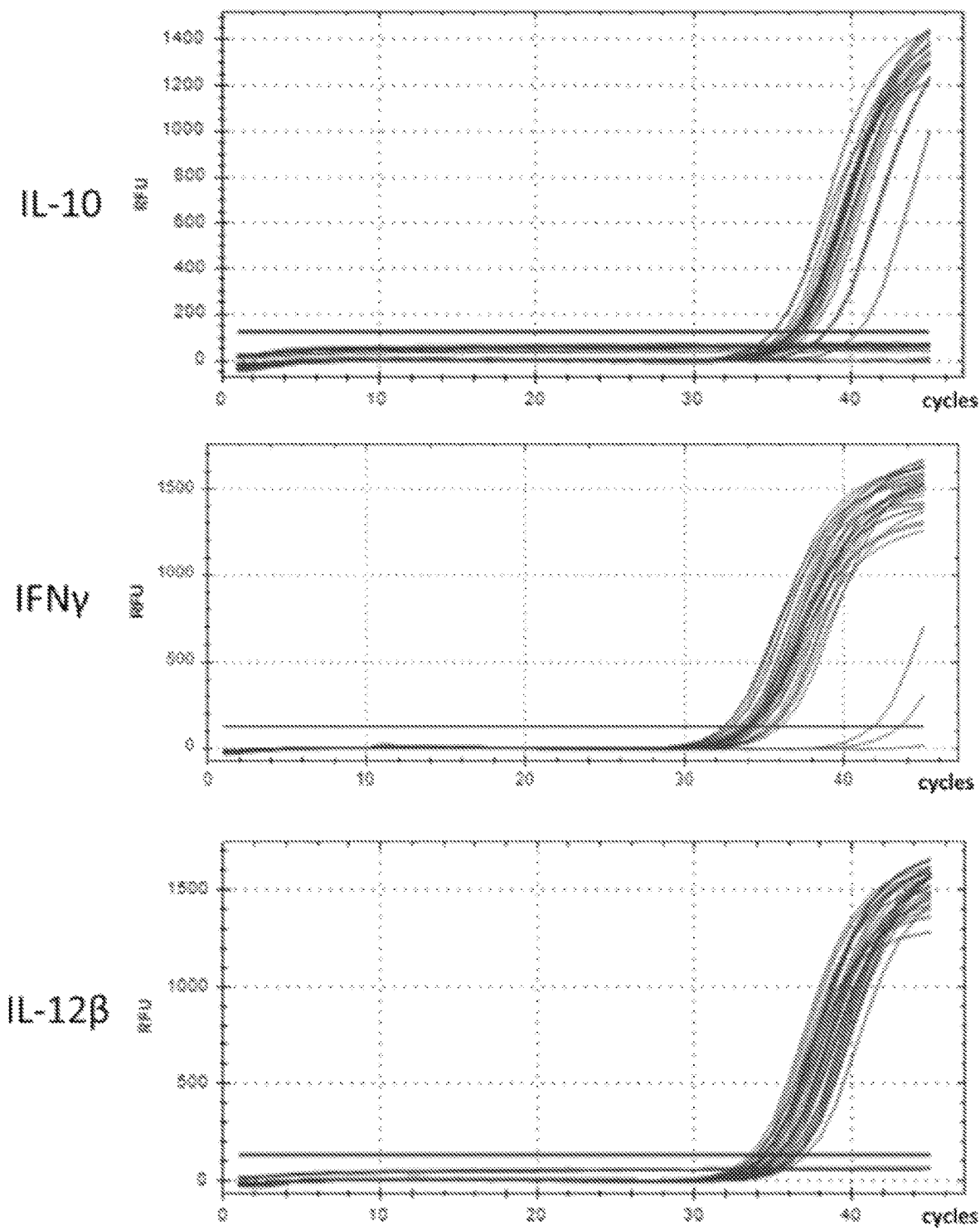

Besides SYP and PSD-95, significant changes of Iba-1 and GFAP were shown in response to Tat, PAM/α7 nAChR and p38 MAPK signaling pathway. Tat expression led to increases of GFAP expression and PAM treatment completely reversed the increases in CORT and in vitro. Similar response was obtained with Iba-1. α7 nAChR knockout further abrogated PAM effects on Tat-induced Iba-1 expression but not GFAP expression, suggesting distinct roles of α7 nAChR in astrocytes. α7 nAChR expressed in these non-excitable glia cells is usually associated with its anti-inflammatory role.[93] However, infiltrates of immune cells in Tat-expressing brain of the iTat mice were not detected (FIG. 13). Significant changes of pro-inflammatory cytokines/chemokines such as TNF-α were also not detected in the brain of iTat mice and in in vitro Tat-containing conditioned medium-treated primary microglia and astrocytes (FIG. 14), despite the fact that astrogliosis and microgliosis were clearly detected by the current study and previous studies.[32,38] Taken together, the results demonstrated that activation of microglia and astrocytes were important links among Tat neurotoxicity, PAM/α7 nAChR interaction, and p38 MAPK signaling pathway and suggest that α7 nAChR anti-inflammatory property is not primarily responsible for PAM neuroprotective effects against Tat neurotoxicity. Of note were differences of GFAP and Iba-1 expression in CORT and HIP and their differential response to PAM/α7 nAChR activation, which may likely result from the cell heterogeneity in different brain regions and different expression of α7 nAChR in these cells.

Importantly, the findings from the current study raised the possibility that PSD-95 is the convergent link involved in the interplays between Tat neurotoxicity and α7 nAChR activation. PSD95 participates in synapse formation, maturation and plasticity and glutamate-mediated neurotoxicityl[102], its loss leads to abnormal LTP, impairs learning and memory process[103-105], and is involved in several neurological and psychiatric diseases.[106-109] Tat binds to LRP[23] and induces LRP/PSD-95/NMDAR complex formation potentiates glutamate excitotoxicity and promotes neuronal apoptosis[110]. Therapeutic approaches have been proposed to disrupt PSD-95/NMDAR complex to ameliorate pathological changes.[111-113] Meanwhile, the results showed increased PSD-95 expression was closely associated with improved learning and memory and locomotor activity. It is possible that increased PSD-95 serves as a compensatory mechanism for its loss in formation of abnormal complexes and to enhance its synaptic function, as evidenced in studies in which increased PSD-95 correlates with its protective effects in AD and PD animal models.[114-116]

In conclusion, this study showed that PAM treatment led to significant protection against Tat-induced locomotor, learning, and memory impairments and astrocyte/microglia activation and neuronal injury. This study also showed that α7 nAChR activation followed by p38 MAPK-mediated PSD-95 expression contributed to PAM-induced neuroprotection against Tat neurotoxicity. These findings demonstrate for the first time that α7 nAChR and its PAM hold significant therapeutic promise for development of therapeutics for HAND.

REFERENCES

1. Munoz, A., Sabin, C. A. & Phillips, A. N. The incubation period of AIDS. *AIDS* 11 Suppl A, S69-76 (1997).
2. Survival after introduction of HAART in people with known duration of HIV-1 infection. The CASCADE Collaboration. Concerted Action on SeroConversion to AIDS and Death in Europe. *Lancet* 355, 1158-1159 (2000).
3. Egger, M., et al. Prognosis of HIV-1-infected patients starting highly active antiretroviral therapy: a collaborative analysis of prospective studies. *Lancet* 360, 119-129 (2002).
4. May, M., et al. Prognosis of HIV-1-infected patients up to 5 years after initiation of HAART: collaborative analysis of prospective studies. *AIDS* 21, 1185-1197 (2007).
5. May, M. T., et al. HIV treatment response and prognosis in Europe and North America in the first decade of highly active antiretroviral therapy: a collaborative analysis. *Lancet* 368, 451-458 (2006).
6. Cysique, L. A., Maruff, P. & Brew, B. J. Prevalence and pattern of neuropsychological impairment in human immunodeficiency virus-infected/acquired immunodeficiency syndrome (HIV/AIDS) patients across pre- and post-highly active antiretroviral therapy eras: a combined study of two cohorts. *J Neurovirol* 10, 350-357 (2004).
7. Masliah, E., DeTeresa, R. M., Mallory, M. E. & Hansen, L. A. Changes in pathological findings at autopsy in AIDS cases for the last 15 years. *AIDS* 14, 69-74 (2000).
8. Ellis, R., Langford, D. & Masliah, E. HIV and antiretroviral therapy in the brain: neuronal injury and repair. *Nat Rev Neurosci* 8, 33-44 (2007).
9. d'Arminio Monforte, A., et al. Changing incidence of central nervous system diseases in the EuroSIDA cohort. *Ann Neurol* 55, 320-328 (2004).

10. Sacktor, N., et al. HIV-associated neurologic disease incidence changes: Multicenter AIDS Cohort Study, 1990-1998. *Neurology* 56, 257-260 (2001).
11. Sacktor, N., et al. HIV-associated cognitive impairment before and after the advent of combination therapy. *J Neurovirol* 8, 136-142 (2002).
12. Giancola, M. L., et al. Neuroactive antiretroviral drugs do not influence neurocognitive performance in less advanced HIV-infected patients responding to highly active antiretroviral therapy. *J Acquir Immune Defic Syndr* 41, 332-337 (2006).
13. Dawes, S., et al. Variable patterns of neuropsychological performance in HIV-1 infection. *J Clin Exp Neuropsychol* 30, 613-626 (2008).
14. Langford, T. D., Letendre, S. L., Larrea, G. J. & Masliah, E. Changing patterns in the neuropathogenesis of HIV during the HAART era. *Brain Pathol* 13, 195-210 (2003).
15. Heaton, R. K., et al. The impact of HIV-associated neuropsychological impairment on everyday functioning. *J Int Neuropsychol Soc* 10, 317-331 (2004).
16. Letendre, S., et al. Validation of the CNS Penetration-Effectiveness rank for quantifying antiretroviral penetration into the central nervous system. *Arch Neurol* 65, 65-70 (2008).
17. Yilmaz, A., Price, R. W. & Gisslen, M. Antiretroviral drug treatment of CNS HIV-1 infection. *J Antimicrob Chemother* 67, 299-311 (2012).
18. Caniglia, E. C., et al. Antiretroviral penetration into the CNS and incidence of AIDS-defining neurologic conditions. *Neurology* 83, 134-141 (2014).
19. Heaton, R. K., et al. HIV-associated neurocognitive disorders persist in the era of potent antiretroviral therapy: CHARTER Study. *Neurology* 75, 2087-2096 (2010).
20. Bagasra, O., et al. Cellular reservoirs of HIV-1 in the central nervous system of infected individuals: identification by the combination of in situ polymerase chain reaction and immunohistochemistry. *AIDS* 10, 573-585 (1996).
21. Wallet, C., et al. Microglial Cells: The Main HIV-1 Reservoir in the Brain. *Front Cell Infect Microbiol* 9, 362 (2019).
22. Brack-Werner, R. Astrocytes: HIV cellular reservoirs and important participants in neuropathogenesis. *AIDS* 13, 1-22 (1999).
23. Liu, Y, et al. Uptake of HIV-1 tat protein mediated by low-density lipoprotein receptor-related protein disrupts the neuronal metabolic balance of the receptor ligands. *Nat Med* 6, 1380-1387 (2000).
24. Frankel, A. D. & Pabo, C. O. Cellular uptake of the tat protein from human immunodeficiency virus. *Cell* 55, 1189-1193 (1988).
25. Hudson, L., et al. Detection of the human immunodeficiency virus regulatory protein tat in CNS tissues. *J Neurovirol* 6, 145-155 (2000).
26. Johnson, T. P., et al. Induction of IL-17 and nonclassical T-cell activation by HIV-Tat protein. *Proc Natl Acad Sci USA* 110, 13588-13593 (2013).
27. Henderson, L. J., et al. Presence of Tat and transactivation response element in spinal fluid despite antiretroviral therapy. *AIDS* 33 Suppl 2, S145-S157 (2019).
28. Zhou, B. Y., Liu, Y, Kim, B., Xiao, Y. & He, J. J. Astrocyte activation and dysfunction and neuron death by HIV-1 Tat expression in astrocytes. *Mol Cell Neurosci* 27, 296-305 (2004).
29. Zhou, B. Y. & He, J. J. Proliferation inhibition of astrocytes, neurons, and non-glial cells by intracellularly expressed human immunodeficiency virus type 1 (HIV-1) Tat protein. *Neurosci Lett* 359, 155-158 (2004).
30. Zou, W., et al. Protection against human immunodeficiency virus type 1 Tat neurotoxicity by *Ginkgo biloba* extract EGb 761 involving glial fibrillary acidic protein. *Am J Pathol* 171, 1923-1935 (2007).
31. Fan, Y, Zou, W., Green, L. A., Kim, B. O. & He, J. J. Activation of Egr-1 expression in astrocytes by HIV-1 Tat: new insights into astrocyte-mediated Tat neurotoxicity. *J Neuroimmune Pharmacol* 6, 121-129 (2011).
32. Zou, W., et al. Involvement of p300 in constitutive and HIV-1 Tat-activated expression of glial fibrillary acidic protein in astrocytes. *Glia* 58, 1640-1648 (2010).
33. Fields, J., et al. HIV-1 Tat alters neuronal autophagy by modulating autophagosome fusion to the lysosome: implications for HIV-associated neurocognitive disorders. *J Neurosci* 35, 1921-1938 (2015).
34. Fan, Y, Gao, X., Chen, J., Liu, Y. & He, J. J. HIV Tat Impairs Neurogenesis through Functioning As a Notch Ligand and Activation of Notch Signaling Pathway. *J Neurosci* 36, 11362-11373 (2016).
35. Fan, Y. & He, J. J. HIV-1 Tat Promotes Lysosomal Exocytosis in Astrocytes and Contributes to Astrocyte-mediated Tat Neurotoxicity. *J Biol Chem* 291, 22830-22840 (2016).
36. Fan, Y. & He, J. J. HIV-1 Tat Induces Unfolded Protein Response and Endoplasmic Reticulum Stress in Astrocytes and Causes Neurotoxicity through Glial Fibrillary Acidic Protein (GFAP) Activation and Aggregation. *J Biol Chem* 291, 22819-22829 (2016).
37. Rahimian, P. & He, J. J. HIV-1 Tat-shortened neurite outgrowth through regulation of microRNA-132 and its target gene expression. *J Neuroinflammation* 13, 247 (2016).
38. Kim, B. O., et al. Neuropathologies in transgenic mice expressing human immunodeficiency virus type 1 Tat protein under the regulation of the astrocyte-specific glial fibrillary acidic protein promoter and doxycycline. *Am J Pathol* 162, 1693-1707 (2003).
39. Raybuck, J. D., Hargus, N. J. & Thayer, S. A. A GluN2B-Selective NMDAR Antagonist Reverses Synapse Loss and Cognitive Impairment Produced by the HIV-1 Protein Tat. *J Neurosci* 37, 7837-7847 (2017).
40. Kesby, J. P., Markou, A. & Semenova, S. The effects of HIV-1 regulatory TAT protein expression on brain reward function, response to psychostimulants and delay-dependent memory in mice. *Neuropharmacology* 109, 205-215 (2016).
41. Nookala, A. R., et al. Methamphetamine augment HIV-1 Tat mediated memory deficits by altering the expression of synaptic proteins and neurotrophic factors. *Brain Behav Immun* 71, 37-51 (2018).
42. Carey, A. N., Sypek, E. I., Singh, H. D., Kaufman, M. J. & McLaughlin, J. P. Expression of HIV-Tat protein is associated with learning and memory deficits in the mouse. *Behav Brain Res* 229, 48-56 (2012).
43. Li, S. T., et al. HIV-1 Tat inhibits long-term potentiation and attenuates spatial learning [corrected]. *Ann Neurol* 55, 362-371 (2004).
44. Moran, L. M., Fitting, S., Booze, R. M., Webb, K. M. & Mactutus, C. F. Neonatal intrahippocampal HIV-1 protein Tat(1-86) injection: neurobehavioral alterations in the absence of increased inflammatory cytokine activation. *Int J Dev Neurosci* 38, 195-203 (2014).
45. Hahn, Y. K., et al. Effects of chronic HIV-1 Tat exposure in the CNS: heightened vulnerability of males versus females to changes in cell numbers, synaptic integrity, and behavior. *Brain Struct Funct* 220, 605-623 (2015).
46. Fu, X., Lawson, M. A., Kelley, K. W. & Dantzer, R. HIV-1 Tat activates indoleamine 2,3 dioxygenase in murine organotypic hippocampal slice cultures in a p38 mitogen-activated protein kinase-dependent manner. *J Neuroinflammation* 8, 88 (2011).
47. Gotti, C., Zoli, M. & Clementi, F. Brain nicotinic acetylcholine receptors: native subtypes and their relevance. *Trends Pharmacol Sci* 27, 482-491 (2006).
48. Albuquerque, E. X., Pereira, E. F., Alkondon, M. & Rogers, S. W. Mammalian nicotinic acetylcholine receptors: from structure to function. *Physiol Rev* 89, 73-120 (2009).
49. Hoskin, J. L., Al-Hasan, Y. & Sabbagh, M. N. Nicotinic Acetylcholine Receptor Agonists for the Treatment of Alzheimer's Dementia: An Update. *Nicotine Tob Res* 21, 370-376 (2019).
50. Bouzat, C., Lasala, M., Nielsen, B. E., Corradi, J. & Esandi, M. D. C. Molecular function of alpha7 nicotinic receptors as drug targets. *J Physiol* 596, 1847-1861 (2018).
51. King, J. R., Nordman, J. C., Bridges, S. P., Lin, M. K. & Kabbani, N. Identification and Characterization of a G Protein-binding Cluster in alpha7 Nicotinic Acetylcholine Receptors. *J Biol Chem* 290, 20060-20070 (2015).
52. Dajas-Bailador, F. A., Soliakov, L. & Wonnacott, S. Nicotine activates the extracellular signal-regulated kinase 1/2 via the alpha7 nicotinic acetylcholine receptor and protein kinase A, in SH-SY5Y cells and hippocampal neurones. *J Neurochem* 80, 520-530 (2002).
53. Dineley, K. T., et al. Beta-amyloid activates the mitogen-activated protein kinase cascade via hippocampal alpha7 nicotinic acetylcholine receptors: In vitro and in vivo mechanisms related to Alzheimer's disease. *J Neurosci* 21, 4125-4133 (2001).
54. El Kouhen, R., Hu, M., Anderson, D. J., Li, J. & Gopalakrishnan, M. Pharmacology of alpha7 nicotinic acetylcholine receptor mediated extracellular signal-regulated kinase signalling in PC12 cells. *Br J Pharmacol* 156, 638-648 (2009).
55. King, J. R. & Kabbani, N. Alpha 7 nicotinic receptor coupling to heterotrimeric G proteins modulates RhoA activation, cytoskeletal motility, and structural growth. *J Neurochem* 138, 532-545 (2016).
56. Egea, J., et al. Anti-inflammatory role of microglial alpha7 nAChRs and its role in neuroprotection. *Biochem Pharmacol* 97, 463-472 (2015).
57. Kim, H., et al. The proximal tubular alpha7 nicotinic acetylcholine receptor attenuates ischemic acute kidney injury through Akt/PKC signaling-mediated HO-1 induction. *Exp Mol Med* 50, 40 (2018).
58. Larsen, H. M., Hansen, S. K., Mikkelsen, J. D., Hyttel, P. & Stummann, T. C. Alpha7 nicotinic acetylcholine receptors and neural network synaptic transmission in human induced pluripotent stem cell-derived neurons. *Stem Cell Res* 41, 101642 (2019).
59. Buckingham, S. D., Jones, A. K., Brown, L. A. & Sattelle, D. B. Nicotinic acetylcholine receptor signalling: roles in Alzheimer's disease and amyloid neuroprotection. *Pharmacol Rev* 61, 39-61 (2009).
60. Xu, S., et al. Activation of alpha7-nAChRs protects SH-SY5Y cells from 1-methyl-4-phenylpyridinium-induced apoptotic cell death via ERK/p53 signaling pathway. *J Cell Physiol* 234, 18480-18491 (2019).
61. Tregellas, J. R. & Wylie, K. P. Alpha7 Nicotinic Receptors as Therapeutic Targets in Schizophrenia. *Nicotine Tob Res* 21, 349-356 (2019).
62. Rahman, S., Engleman, E. A. & Bell, R. L. Nicotinic receptor modulation to treat alcohol and drug dependence. *Front Neurosci* 8, 426 (2014).
63. Xiao, C., Zhou, C. Y., Jiang, J. H. & Yin, C. Neural circuits and nicotinic acetylcholine receptors mediate the cholinergic regulation of midbrain dopaminergic neurons and nicotine dependence. *Acta Pharmacol Sin* 41, 1-9 (2020).
64. Mineur, Y. S., Mose, T. N., Blakeman, S. & Picciotto, M. R. Hippocampal alpha7 nicotinic ACh receptors contribute to modulation of depression-like behaviour in C57BL/6J mice. *Br J Pharmacol* 175, 1903-1914 (2018).
65. Liu, Q., et al. alpha7 Nicotinic acetylcholine receptor-mediated anti-inflammatory effect in a chronic migraine rat model via the attenuation of glial cell activation. *J Pain Res* 11, 1129-1140 (2018).
66. Koukouli, F., et al. Nicotine reverses hypofrontality in animal models of addiction and schizophrenia. *Nat Med* 23, 347-354 (2017).
67. Jones, C. K., Byun, N. & Bubser, M. Muscarinic and nicotinic acetylcholine receptor agonists and allosteric modulators for the treatment of schizophrenia. *Neuropsychopharmacology* 37, 16-42 (2012).
68. Sun, F., Johnson, S. R., Jin, K. & Uteshev, V. V. Boosting Endogenous Resistance of Brain to Ischemia. *Mol Neurobiol* 54, 2045-2059 (2017).
69. Dash, P. K., et al. Activation of Alpha 7 Cholinergic Nicotinic Receptors Reduce Blood-Brain Barrier Permeability following Experimental Traumatic Brain Injury. *J Neurosci* 36, 2809-2818 (2016).
70. Capo-Velez, C. M., et al. The alpha7-nicotinic receptor contributes to gp120-induced neurotoxicity: implications in HIV-associated neurocognitive disorders. *Sci Rep* 8, 1829 (2018).
71. Liu, L., et al. Alpha7 nicotinic acetylcholine receptor is required for amyloid pathology in brain endothelial cells induced by Glycoprotein 120, methamphetamine and nicotine. *Sci Rep* 7, 40467 (2017).
72. Zhang, B., et al. Alpha7 nicotinic acetylcholine receptor is required for blood-brain barrier injury-related CNS disorders caused by *Cryptococcus neoformans* and HIV-1 associated comorbidity factors. *BMC Infect Dis* 15, 352 (2015).
73. Uteshev, V. V. Allosteric Modulation of Nicotinic Acetylcholine Receptors: The Concept and Therapeutic Trends. *Curr Pharm Des* 22, 1986-1997 (2016).
74. Uteshev, V. V. The therapeutic promise of positive allosteric modulation of nicotinic receptors. *Eur J Pharmacol* 727, 181-185 (2014).
75. Yang, J. S., Seo, S. W, Jang, S., Jung, G. Y. & Kim, S. Rational engineering of enzyme allosteric regulation through sequence evolution analysis. *PLoS Comput Biol* 8, e1002612 (2012).
76. McLean, S. L., et al. PNU-120596, a positive allosteric modulator of alpha7 nicotinic acetylcholine receptors, reverses a sub-chronic phencyclidine-induced cognitive deficit in the attentional set-shifting task in female rats. *J Psychopharmacol* 26, 1265-1270 (2012).
77. Gibbs, K. L., et al. Inhibiting p38 MAPK alpha rescues axonal retrograde transport defects in a mouse model of ALS. *Cell Death Dis* 9, 596 (2018).
78. Mannangatti, P., NarasimhaNaidu, K., Damaj, M. I., Ramamoorthy, S. & Jayanthi, L. D. A Role for p38 Mitogen-activated Protein Kinase-mediated Threonine 30-dependent Norepinephrine Transporter Regulation in Cocaine Sensitization and Conditioned Place Preference. *J Biol Chem* 290, 10814-10827 (2015).
79. Maphis, N., et al. Selective suppression of the alpha isoform of p38 MAPK rescues late-stage tau pathology. *Alzheimers Res Ther* 8, 54 (2016).
80. Robson, M. J., et al. p38alpha MAPK signaling drives pharmacologically reversible brain and gastrointestinal phenotypes in the SERT Ala56 mouse. *Proc Natl Acad Sci USA* 115, E10245-E10254 (2018).
81. Ye, Q., Zeng, C., Luo, C. & Wu, Y. Ferrostatin-1 mitigates cognitive impairment of epileptic rats by inhibiting P38 MAPK activation. *Epilepsy Behav* 103, 106670 (2020).
82. Barone, F. C., et al. SB 239063, a second-generation p38 mitogen-activated protein kinase inhibitor, reduces brain injury and neurological deficits in cerebral focal ischemia. *J Pharmacol Exp Ther* 296, 312-321 (2001).
83. Bruchas, M. R., et al. Stress-induced p38 mitogen-activated protein kinase activation mediates kappa-opioid-dependent dysphoria. *J Neurosci* 27, 11614-11623 (2007).
84. Singh, I. N., et al. Differential involvement of p38 and JNK MAP kinases in HIV-1 Tat and gp120-induced apoptosis and neurite degeneration in striatal neurons. *Neuroscience* 135, 781-790 (2005).
85. Sui, Z., et al. Inhibition of mixed lineage kinase 3 prevents HIV-1 Tat-mediated neurotoxicity and monocyte activation. *J Immunol* 177, 702-711 (2006).
86. Fu, X., Lawson, M. A., Kelley, K. W. & Dantzer, R. HIV-1 Tat activates indoleamine 2,3 dioxygenase in murine organotypic hippocampal slice cultures in a p38 mitogen-activated protein kinase-dependent manner. *J Neuroinflammation* 8, 88 (2011).
87. Shanware, N. P., Williams, L. M., Bowler, M. J. & Tibbetts, R. S. Non-specific in vivo inhibition of CK1 by the pyridinyl imidazole p38 inhibitors SB 203580 and SB 202190. *BMB Rep* 42, 142-147 (2009).
88. Barone, F. C., et al. SB 239063, a second-generation p38 mitogen-activated protein kinase inhibitor, reduces brain injury and neurological deficits in cerebral focal ischemia. *J Pharmacol Exp Ther* 296, 312-321 (2001).
89. Langford, D., et al. Doxycycline-inducible and astrocyte-specific HIV-1 Tat transgenic mice (iTat) as an HIV/neuroAIDS model. *J Neurovirol* 24, 168-179 (2018).
90. Johnson, T. P., et al. Induction of IL-17 and nonclassical T-cell activation by HIV-Tat protein. *Proc Natl Acad Sci USA* 110, 13588-13593 (2013).
91. Henderson, L. J., et al. Presence of Tat and transactivation response element in spinal fluid despite antiretroviral therapy. *AIDS* 33 Suppl 2, S145-S157 (2019).
92. Natarajaseenivasan, K., et al. Astrocytic metabolic switch is a novel etiology for Cocaine and HIV-1 Tat-mediated neurotoxicity. *Cell Death Dis* 9, 415 (2018).
93. Foucault-Fruchard, L. & Antier, D. Therapeutic potential of alpha7 nicotinic receptor agonists to regulate neuroinflammation in neurodegenerative diseases. *Neural Regen Res* 12, 1418-1421 (2017).
94. Singh, I. N., et al. Differential involvement of p38 and JNK MAP kinases in HIV-1 Tat and gp120-induced apoptosis and neurite degeneration in striatal neurons. *Neuroscience* 135, 781-790 (2005).
95. Wen, A. Y., Sakamoto, K. M. & Miller, L. S. The role of the transcription factor CREB in immune function. *J Immunol* 185, 6413-6419 (2010).
96. Xiang, T., et al. Nicotine enhances invasion and metastasis of human colorectal cancer cells through the nicotinic acetylcholine receptor downstream p38 MAPK signaling pathway. *Oncol Rep* 35, 205-210 (2016).
97. Kim, N., Kukkonen, S., Martinez-Viedma Mdel, P., Gupta, S. & Aldovini, A. Tat engagement of p38 MAP kinase and IRF7 pathways leads to activation of interferon-stimulated genes in antigen-presenting cells. *Blood* 121, 4090-4100 (2013).
98. Coulthard, L. R., White, D. E., Jones, D. L., McDermott, M. F. & Burchill, S. A. p38(MAPK): stress responses from molecular mechanisms to therapeutics. *Trends Mol Med* 15, 369-379 (2009).
99. Gajanayaka, N., et al. HIV and HIV-Tat inhibit LPS-induced IL-27 production in human macrophages by distinct intracellular signaling pathways. *J Leukoc Biol* 102, 925-939 (2017).
100. Asomugha, C. O., Linn, D. M. & Linn, C. L. ACh receptors link two signaling pathways to neuroprotection against glutamate-induced excitotoxicity in isolated RGCs. *J Neurochem* 112, 214-226 (2010).
101. Medders, K. E. & Kaul, M. Mitogen-activated protein kinase p38 in HIV infection and associated brain injury. *J Neuroimmune Pharmacol* 6, 202-215 (2011).
102. Han, K. & Kim, E. Synaptic adhesion molecules and PSD-95. *Prog Neurobiol* 84, 263-283 (2008).
103. Fernandez, E., et al. Arc Requires PSD95 for Assembly into Postsynaptic Complexes Involved with Neural Dysfunction and Intelligence. *Cell Rep* 21, 679-691 (2017).
104. Cao, J., et al. The PSD95-nNOS interface: a target for inhibition of excitotoxic p38 stress-activated protein kinase activation and cell death. *J Cell Biol* 168, 117-126 (2005).
105. Brenman, J. E., et al. Interaction of nitric oxide synthase with the postsynaptic density protein PSD-95 and alpha1-syntrophin mediated by PDZ domains. *Cell* 84, 757-767 (1996).
106. Sultana, R., Banks, W. A. & Butterfield, D. A. Decreased levels of PSD95 and two associated proteins and increased levels of BCl2 and caspase 3 in hippocampus from subjects with amnestic mild cognitive impairment: Insights into their potential roles for loss of synapses and memory, accumulation of Abeta, and neurodegeneration in a prodromal stage of Alzheimer's disease. *J Neurosci Res* 88, 469-477 (2010).
107. Calabrese, F., Riva, M. A. & Molteni, R. Synaptic alterations associated with depression and schizophrenia: potential as a therapeutic target. *Expert Opin Ther Targets* 20, 1195-1207 (2016).
108. Selkoe, D. J. Alzheimer's disease is a synaptic failure. *Science* 298, 789-791 (2002).
109. Gong, Y. & Lippa, C. F. Review: disruption of the postsynaptic density in Alzheimer's disease and other neurodegenerative dementias. *Am J Alzheimers Dis Other Demen* 25, 547-555 (2010).
110. Eugenin, E. A., et al. HIV-tat induces formation of an LRP-PSD-95-NMDAR-nNOS complex that promotes apoptosis in neurons and astrocytes. *Proc Natl Acad Sci USA* 104, 3438-3443 (2007).
111. Li, L. P., et al. PSD95 and nNOS interaction as a novel molecular target to modulate conditioned fear: relevance to PTSD. *Transl Psychiatry* 8, 155 (2018).
112. Cui, H., et al. PDZ protein interactions underlying NMDA receptor-mediated excitotoxicity and neuroprotection by PSD-95 inhibitors. *J Neurosci* 27, 9901-9915 (2007).

113. Khan, Z. & Lafon, M. PDZ domain-mediated protein interactions: therapeutic targets in neurological disorders. *Curr Med Chem* 21, 2632-2641 (2014).

114. Chen, Y., et al. Hsp90 chaperone inhibitor 17-AAG attenuates Abeta-induced synaptic toxicity and memory impairment. *J Neurosci* 34, 2464-2470 (2014).

115. Bustos, F. J., et al. Epigenetic editing of the Dlg4/PSD95 gene improves cognition in aged and Alzheimer's disease mice. *Brain* 140, 3252-3268 (2017).

116. Tripathi, P., Singh, A., Bala, L., Patel, D. K. & Singh, M. P. Ibuprofen Protects from Cypermethrin-Induced Changes in the Striatal Dendritic Length and Spine Density. *Mol Neurobiol* 55, 2333-2339 (2018).

---

The invention claimed is:

1. A method of treating HIV-associated neurological disorders (HAND) in a subject, wherein the method comprises administering an effective dose of a positive allosteric modulator (PAM) of α7 nicotinic acetylcholine receptor, and an integrase inhibitor, wherein the PAM is PNU-120596 (1-(5-chloro-2,4-dimethoxy-phenyl)-3-(5-methyl-isoxazol-3-yl)-urea).

2. The method of claim 1, wherein the effective dose of the PAM of α7 nicotinic acetylcholine receptor comprises about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per day.

3. The method of claim 1, wherein the effective dose of the PAM of α7 nicotinic acetylcholine receptor comprises about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 6.0 mg/kg, about 7.0 mg/kg, about 8.0 mg/kg, about 9.0 mg/kg, about 10 mg/kg about 15 mg/kg, about 20 mg/kg, about 25 mg/kg, about 30 mg/kg, about 35 mg/kg, about 40 mg/kg, about 45 mg/kg, or about 50 mg/kg per day.

4. The method of claim 1, wherein the effective dose of the PAM of α7 nicotinic acetylcholine receptor results in a serum concentration in the subject of about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 2.0 µM, about 3.0 µM, about 4.0 µM, about 5.0 µM, about 6.0 µM, about 7.0 µM, about 8.0 µM, about 9.0 µM, or about 10 µM.

5. The method of claim 1 further comprising administering one or more of a nucleotide reverse transcriptase inhibitor (NRTI), a non-nucleotide reverse transcriptase inhibitor (NNRTI), and a protease inhibitor (PI).

6. The method of claim 5, wherein the nucleotide reverse transcriptase inhibitor (NRTI) is selected from one or more of abacavir, emtricitabine, lamivudine, tenofovir disoproxil fumarate, or zidovudine.

7. The method of claim 5, wherein the non-nucleotide reverse transcriptase inhibitor (NNRTI) is selected from one or more of doravirine, efavirenz, etravirine, nevirapine, or rilpivirine.

8. The method of claim 5, wherein the protease inhibitor (PI) is selected from one or more of atazanavir, darunavir, fosamprenavir, ritonavir, saquinavir, or tipranavir.

9. The method of claim 1, wherein the integrase inhibitor is selected from one or more of dolutegravir, or raltegravir.

10. The method of claim 1, wherein the method results in improved mood, psychiatric benefits, improved locomotor functions, improved learning, and/or improved memory deficits in the subject.

* * * * *

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonulceotide

<400> SEQUENCE: 1
caccacgctc ttctgtctac t                                              21

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonulceotide

<400> SEQUENCE: 2
tttgctacga cgtgggcta                                                 19

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonulceotide

<400> SEQUENCE: 3
gaaatgccac cttttgacag tga                                            23

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonulceotide

<400> SEQUENCE: 4
agtgatactg cctgcctgaa g                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 5
gagactcttt cgggcttttc                                                20

<210> SEQ ID NO 6
<211> LENGTH: 21
<212> TYPE: DNA
<213> ORGANISM: Artificial Sequence
```

```
<220> FEATURE:
<223> OTHER INFORMATION: Synthetic oligonulceotide

<400> SEQUENCE: 6
tgatgctctt taggctttcc a                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 7
acaagtccgg agaggagact                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 8
ttctgcaagt gcatcatcgt                                                20

<210> SEQ ID NO 9
<211> LENGTH: 29
<212> TYPE: DNA
<213> ORGANISM: Artificial Sequence
<220> FEATURE:
<223> OTHER INFORMATION: Synthetic oligonulceotide

<400> SEQUENCE: 9
tactagagag acttcttcca caacaagag                                      29

<210> SEQ ID NO 10
<211> LENGTH: 27
<212> TYPE: DNA
<213> ORGANISM: Artificial Sequence
<220> FEATURE:
<223> OTHER INFORMATION: Synthetic oligonulceotide

<400> SEQUENCE: 10
tctggtacat cttcaagtcc tcataga                                        27

<210> SEQ ID NO 11
<211> LENGTH: 26
<212> TYPE: DNA
<213> ORGANISM: Artificial Sequence
<220> FEATURE:
<223> OTHER INFORMATION: Synthetic oligonulceotide

<400> SEQUENCE: 11
gacaacacgc tttactttat acctga                                         26

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 12
gtgaagtcgg ccaaagttgt                                                20
```

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonulceotide

<400> SEQUENCE: 13
cactcacctg ctgctactca t                                              21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 14
attccttctt ggggtcagca                                                20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonulceotide

<400> SEQUENCE: 15
tgcttttgtg cctgcgtaat g                                              21

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonulceotide

<400> SEQUENCE: 16
tccaagctga gtcagcgttt tc                                             22

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 17
ccagaaatca aggagcattt                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 18
cacactgcag gtgttttagc                                                20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonulceotide

```
<400> SEQUENCE: 19
ggatgcattc atgagtattg c                                              21

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonulceotide

<400> SEQUENCE: 20
ccttttccgc ttcctgagg                                                 19

<210> SEQ ID NO 21
<211> LENGTH: 28
<212> TYPE: DNA
<213> ORGANISM: Artificial Sequence
<220> FEATURE:
<223> OTHER INFORMATION: Synthetic oligonulceotide

<400> SEQUENCE: 21
gaccatcact gtcaaagagt ttctagat                                       28

<210> SEQ ID NO 22
<211> LENGTH: 29
<212> TYPE: DNA
<213> ORGANISM: Artificial Sequence
<220> FEATURE:
<223> OTHER INFORMATION: Synthetic oligonulceotide

<400> SEQUENCE: 22
aggaaagtct tgtttttgaa attttttaa                                      29

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 23
agagaagtgg ggtggctttt                                                20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 24
aaactggaac ggtgaaggtg                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 25
ttcctggtcc tgctgtgtta                                                20

<210> SEQ ID NO 26
```

```
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 26
atcagatgtt gctggcatga                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonulceotide

<400> SEQUENCE: 27
ttcctggtcc tgctgtgtta                                               20

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonulceotide

<400> SEQUENCE: 28
ccctttatag attcgccctt g                                             21
```